US006340568B2

(12) United States Patent
Hefti

(10) Patent No.: US 6,340,568 B2
(45) Date of Patent: Jan. 22, 2002

(54) METHOD FOR DETECTING AND CLASSIFYING NUCLEIC ACID HYBRIDIZATION

(75) Inventor: John Hefti, San Francisco, CA (US)

(73) Assignee: Signature BioScience, Inc., Hayward, CA (US)

(*) Notice: Subject to any disclaimer, the term of this patent is extended or adjusted under 35 U.S.C. 154(b) by 0 days.

(21) Appl. No.: 09/839,860

(22) Filed: Apr. 19, 2001

Related U.S. Application Data

(63) Continuation of application No. 09/365,581, filed on Aug. 2, 1999, which is a continuation-in-part of application No. 09/243,194, filed on Feb. 1, 1999.
(60) Provisional application No. 60/073,445, filed on Feb. 2, 1998, and provisional application No. 60/134,740, filed on May 18, 1999.

(51) Int. Cl.$^7$ .................................. C12Q 1/68

(52) U.S. Cl. ........................................ 435/6

(58) Field of Search ............................ 435/6

(56) References Cited

U.S. PATENT DOCUMENTS

| | | |
|---|---|---|
| 4,683,202 A | 7/1987 | Mullis |
| 4,765,179 A | 8/1988 | Fuller et al. |
| 4,822,566 A | 4/1989 | Newman |
| 5,025,222 A | 6/1991 | Scott |
| 5,156,810 A | 10/1992 | Ribi |
| 5,164,319 A | 11/1992 | Hafeman et al. |
| 5,424,186 A | 6/1995 | Fodor et al. |
| 5,532,128 A | 7/1996 | Eggers et al. |
| 5,632,957 A | 5/1997 | Heller et al. |
| 5,653,939 A | 8/1997 | Hollis et al. |
| 5,656,428 A | 8/1997 | McAllister et al. |
| 5,827,482 A | 10/1998 | Shieh et al. |
| 5,841,914 A | 11/1998 | Shieh et al. |
| 5,846,708 A | 12/1998 | Hollis et al. |
| 5,846,842 A | 12/1998 | Herron et al. |
| 5,846,843 A | 12/1998 | Simon |
| 5,849,486 A | 12/1998 | Heller et al. |
| 5,858,659 A | 1/1999 | Sapolsky et al. |
| 5,858,666 A | 1/1999 | Weiss |
| 5,874,219 A | 2/1999 | Rava et al. |
| 5,966,017 A | 10/1999 | Scott |
| 6,048,692 A | 4/2000 | Maracas et al. |

FOREIGN PATENT DOCUMENTS

| | | |
|---|---|---|
| EP | 0519250 | 12/1992 |
| WO | WO 93 08464 | 4/1993 |
| WO | WO 97/41425 | 4/1996 |
| WO | WO 96/36871 | 11/1996 |
| WO | WO 98/09168 | 3/1998 |
| WO | WO 98 31839 | 7/1998 |
| WO | WO 98/35232 | 8/1998 |
| WO | WO 99/18242 | 4/1999 |
| WO | WO 99 39190 | 8/1999 |
| WO | WO 00 45170 | 8/2000 |

OTHER PUBLICATIONS

Arno et al., "Dielectric Measurements of Lysozyme and Tri–N–Acetyl–D–Glucosamine Association at Radio and Microwave Frequencies", Biosensors & Bioelectrics, 12(9–10):953–958 (1997).

Hianik, "Biosensors Based on Solid Supported Lipid Bilayers and their Physical Properties", Nato Asi Ser., Ser. 2, (1997), 38 (Biosensors for Direct Monitoring of Environmental Pollutant in Field), 317–333.

Smith et al., "Dielectric Relaxation Spectroscopy and Some Applications in the Pharmaceutical Sciences", Journal of Pharmaceutical Sciences, 84(9):1029–1044 (1995).

Hollis et al., "A Swept Frequency Magnitude Method for the Dielectric Characterization of Chemical and Biological Systems", IEEE Transactions on Microwave Theory and Techniques, vol. MTT–28, No. 7, Jul. 1980, pp. 791–801.

O'Donnell–Maloney et al., "The development of Microfabricated Arrays for DNA Sequencing and Analysis" TIBTECH, Oct. 1996, 14:401–407.

Solinas–Toldo et al., "Matrix–Based Comparative Genomic Hybridization: Biochips to Screen for Genomic Imbalances", Genes, Chromosomes & Cancer (1997) 20:399–407.

Tang et al., "Molecular Diagnostics of Infectious Diseases", Clinical Chemistry (1997) 43(11):2021–2038.

Chee et al., "Accessing Genetic Information with High––Density DNA Arrays", Science, (1996) 274:610–614.

Yershov et al., "DNA Analysis and Diagnostics on Oligonucleotide Microchips", Proc. Natl. Acad. Sci. USA, (1996) 93:4913–4918.

Blanchard et al, "Sequences to Array: Probing the Genome's Secrets", Nature Biotechnology, (1996) 14:1649.

Barinaga, Will, DNA Chip, Speed Genome Initiative? Research News (1991) p. 1489.

Drmanac et al. "Processing of cDNA and Genomic Kilobase–Size Clones for Massive Screening, Mapping and Sequencing by Hybridization" BioTechniques, (1994) 17(2):328–336.

Lockhart et al., "Expression Monitoring by Hybridization to High–Density Oligonucleotide Arrays", Nature Biotechnology, (1996) 14:1675–1680.

Schena et al., "Quantitative Monitoring of Gene Expression Patterns with a Complementary DNA Microarray", Science (1995)270:467–470.

DeRisi et al., "Use of a cDNA Microarray to Analyse Gene Expression Patterns in Human Cancer", Nature Genetics, (1996) 14:457–460.

(List continued on next page.)

Primary Examiner—Kenneth R. Horlick
Assistant Examiner—Teresa Strzelecka

(57) ABSTRACT

The present invention provides a variety of methods for conducting analyses of nucleic acids using a detection system which is sensitive to the unique dielectric properties of different hybridization complexes and which can distinguish between different hybridization complexes directly without the use of labels. Methods using the system to perform sequence checking, expression analysis, de novo sequencing and a variety of other nucleic acid analyses are provided.

18 Claims, 26 Drawing Sheets

OTHER PUBLICATIONS

Hacia et al., "Applications of DNA Chips for Genomic Analysis", Molecular Psychiatry, (1998) 3:483–492.

Lipshutz et al., "Using Oligonucleotide Probe Arrays to Access Genetic Diversity", BioTechniques, (1995) 19(3):442–447.

Ramsey, DNA Chips: State–of–the–art, Nature Biotechnology, (1998) 16:40–44.

Southern, "DNA Chips: Analysing Sequence by Hybridization to Oligonucleotides on a Large Scale" TIG, (1996) 12(3):110–115

Wallraff et al., "DNA Sequencing on a Chip", Chemtech, (1997), pp. 22–32.

Marshall et al., "DNA Chips: An Array pf Possibilities", Nature Biotechnology, (1998) 16:27–31.

Schena, "Genome Analysis with Gene Expression Microarrays", BioEssays, (1996) 18(5):427–431.

Sidransky, "Nucleic Acid–Based Methods for the Detection of Cancer", Science, (1997) 278:1054–1058.

Segovia, "Getting Closer to Efficient Gene Discovery, in Silico", Nature Biotechnology, (1998), 16:25.

Nanogen Technology and Products (Product information from the wed site) updated Mar. 3, 1999 (copyright 1996), pp. 1–6.

Overview of Hyseq's Technology, Technology Platforms, pp. 1–3.

GeneChip Application Areas, Affymetrix, Inc. (1998), p. 1.

Constantine et al., "Use of Gene Chip High–Density Oligonucleotide Arrays for Gene Expression Monitoring", Life Science News I, (1998 Amersham Pharmacia Biotech) 3 pages.

Gilles et al., "Single Nucleotide Polymorphic Discrimination by an Electronic Dot Blot Assay on Semiconductor Microchips", Nature Biotechnology, (1999) 17:365–370.

Southern et al., "Molecular Interactions on Microarrays", Nature Genetics Supplement (1999) 21:5–9.

Duggan et al., "Expression Profiling Using cDNA Microassays", Nature Genetics Supplement, (1999) 21:10–14.

Cheung et al., "Making and Reading Microarrays", Nature Genetics Supplement, (1999), 21:15–19.

Lipshutz et al., High Density Synthetic Oligonucleotide Arrays:, Nature Genetics Supplement, (1999) 21:20–24.

Bowtell, "Options Available—From Start to Finish—for Obtaining Expression Data by Microarray", Nature Genetics Supplement, (1999), 21:25–32.

Brown et al., "Exploring the New World of the Genome with DNA Microarrays", Nature Genetics Supplement, (1999) 21:33–37.

Hacia, "Resequencing and Mutational Analysis Using Oligonucleotide Microarrays", Nature Genetics Supplement, (1999), 21:42–47.

Debouck et al., "DNA Microarrays in Drug Discovery and Development", Nature Genetics Supplement, (1999) 21:48–50.

METHOD FOR DETECTING AND CLASSIFYING NUCLEIC ACID HYBRIDIZATION

CROSS-REFERENCES TO RELATED APPLICATIONS

This application is a continuation of U.S. application Ser. No. 09/365,581, filed Aug. 2, 1999, which is a continuation-in-part of U.S. application Ser. No. 09/243,194, filed Feb. 1, 1999, which claims the benefit of U.S. Provisional Application No. 60/073,445, filed Feb. 2, 1998. This application also claims the benefit of U.S. Provisional Application No. 60/134,740, filed May 18, 1999. This application is also related to U.S. Application Ser. No. 09/365,978, filed Aug. 2, 1999. Each of these applications is incorporated herein by reference in its entirety for all purposes.

FIELD OF INVENTION

The present invention relates to novel methods for analyzing the sequences of nucleic acid molecules using spectroscopic methods. In particular, the present invention relates to methods for gene expression analysis, sequence checking, mutation detection, and sequencing of nucleic acids. As such, the methods of the present invention broadly relate to molecular genetics and medical diagnostics.

BACKGROUND OF THE INVENTION

Knowledge of genetic information in the form of the nucleotide sequence of genes is critical to an understanding of various biological phenomenon such as cell development and differentiation, organism growth and reproduction, the underlying causes of disease, etc. For example, proteins serve a variety of structural and catalytic functions. These properties of proteins, however, are a function of the amino acid sequence of the protein, which in turn is encoded by nucleic acid sequences. Nucleic acids can also play a more direct role in cellular processes by functioning in the control and regulation of gene expression.

A variety of hybridization techniques have been developed to conduct various types of nucleic acid analyses to gain insight into how genetic information functions in these different types of biological processes. Typically, hybridization techniques involve the binding of certain target nucleic acids by nucleic acid probes under controlled conditions such that hybridization only occurs between complementary sequences. Using such hybridization techniques, it is possible to conduct gene expression studies, sequence checking studies and determine the sequence of nucleic acids of unknown sequence, as well as a variety of other types of analysis.

Gene expression studies are important because differential expression of genes has been shown to be associated with cell development, cell differentiation, disease states and adaptation to various environmental stimuli. For example, many diseases have been characterized by differences in the expression levels of various genes either through change in copy number of the genetic DNA or through alterations in levels of transcription. In certain diseases, infection is frequently characterized by elevated expression of genes from a particular virus.

Sequence checking refers to methods in which samples containing nucleic acid targets are analyzed to detect the presence of a sequence of interest. This type of analysis has utility in diverse applications, including research, clinical diagnostics, quality control, etc. One particular type of sequence checking which is particularly important is the identification of polymorphisms, which are variations in the genetic code. Often polymorphisms take the form of a change in a single nucleotide and are called single nucleotide polymorphisms (SNPs). In other instances, the polymorphism may exist as a stretch of repeating sequences that vary in length among different individuals. In those instances in which these variations exist in a significant percentage of the population, they can readily be used as markers linked to genes involved in mono- and polygenic traits. Thus, analysis of polymorphisms can play an important role in locating, identifying and characterizing genes which are responsible for specific traits. In particular, polymorphisms can be used to identify genes responsible for certain diseases. Similarly, diagnostic tests can also be developed to detect polymorphisms known to be associated with certain diseases or disorders.

Hybridization techniques can also successfully be used in sequencing nucleic acids of unknown sequence. Such methods typically are considerably faster than conventional sequencing techniques.

Chips to which nucleic acid probes are attached can be used to conduct nucleic acid analyses. Probes can be attached at specific locations on the chip; these locations are often referred to as elements or sites. In some applications, the chip may include many elements arranged in the form of an array. Genetic methods utilizing arrays on chips have the advantage of allowing for parallel processing that can dramatically increase the rate at which analyzes can be conducted as compared to conventional methods which often require laborious electrophoretic separations. However, the current nucleic acid methods using chips typically require complex labeling procedures in order to identify which nucleic acid probes have hybridized with a target molecule. Moreover, the methods frequently involve complicated stringency washes in order to minimize binding between probes and targets which are not fully complementary.

The present invention provides new methods for conducting various types of nucleic acid analysis in which hybridization of probe and target sequences can be detected directly, thereby allowing the analyses to be simplified relative to existing methodologies.

SUMMARY OF THE INVENTION

The present invention provides various methods of analyzing nucleic acids utilizing a system which is sensitive to the dielectric properties of molecules and binding complexes, such as hybridization complexes formed between a nucleic acid probe and a nucleic acid target. The methods include diagnostic methods which involve detecting the presence of one or more target nucleic acids in a sample, quantitative methods, kinetic methods, and a variety of other types of analysis such as sequence checking, expression analysis and de novo sequencing. The methods can detect binding between nucleic acids without the use of labels. Certain methods involve the use of arrays which allows for rapid throughput. Other methods involve the use of spectral profiles which makes it possible to distinguish between different types of hybridization complexes.

Some methods provided by the present invention involve contacting a nucleic acid probe that is electromagnetically coupled to a portion of a signal path with a sample containing a target nucleic acid. The portion of the signal path to which the nucleic acid probe is coupled typically is a continuous transmission line. A response signal is detected for a hybridization complex formed between the nucleic acid probe and the nucleic acid target. Detection may involve propagating a test signal along the signal path and then detecting a response signal formed through modulation of the test signal by the hybridization complex.

Certain diagnostic methods utilize this general approach and include using a nucleic acid probe which is complementary to a target of known sequence. A sample potentially containing the target of known sequence is contacted with the complementary probe. In some methods, the target and probe are allowed to hybridize and then the targets and probes are washed under stringent conditions. In other methods, the stringency wash is unnecessary. Detection of a response signal is indicative of the sample containing the target of known sequence. Such methods can be used in detecting a single nucleotide polymorphism (SNP). The nucleic acid target containing a polymorphic site includes a first or a second base at the polymorphic site. The nucleic acid probe is selected to be complementary to either a nucleic acid target wherein the polymorphic site includes the first base or is complementary to a nucleic acid target wherein the polymorphic site includes the second base. With knowledge of the sequence of the nucleic acid probe, detection of a response signal makes it possible to identify whether the target contains the first or second base at the polymorphic site.

In other aspects, the present invention provides a variety of methods which utilize spectral profiles to analyze nucleic acid hybridization complexes. A profile is a spectrum for a particular hybridization complex. It can include certain signals which are characteristic of the particular complex, thus making it possible to utilize signatures as a diagnostic tool and as a way to distinguish between different types of binding. Thus, certain methods include acquiring a spectrum for a hybridization complex formed between a nucleic acid probe and a nucleic acid target, wherein the nucleic acid probe is electromagnetically coupled to a signal path. A test signal is propagated along the signal path and a response signal for the hybridization complex formed between the probe and target detected. As the test signal is propagated down the signal path, the test signal is varied with time (for example, by varying the wavelength or frequency of the test signal). Certain spectra include plots of a signal parameter (e.g., transmitted power) as a function of frequency, for example.

Methods utilizing profiles can be used for diagnostic purposes. These methods involve obtaining a spectrum as just described wherein the nucleic acid probe is contacted with a sample containing a target nucleic acid prior to propagation of the test signal. The resulting spectrum is then analyzed for the presence of a known signal which is characteristic for a known hybridization complex between a particular probe and a particular target. The presence of the known signal in the spectrum is indicative of the particular target nucleic acid being present in the sample.

Related methods utilize profiles to distinguish between complementary hybridization complexes and mismatch complexes. In these methods, the spectrum that is obtained using a known probe is examined for the presence of a complementary signal and/or a mismatch signal. The presence of the complementary signal is indicative of complementary binding between the nucleic acid probe and the nucleic acid target; likewise, the presence of a mismatch signal is indicative of a hybridization complex between the probe and target which includes a mismatch.

In still other related methods, profiles are used to identify whether a SNP is of the wild type form or a variant form. The target includes a polymorphic site which can include a first or second base. The nucleic acid probe sequence is selected so that if the target includes the first base at the polymorphic site the target forms a complementary hybridization complex. If, however, the target includes the second base at the polymorphic site, then a mismatch hybridization complex is formed. Hence, the presence of a complementary signal in the test spectrum is indicative of the target including the first base at the polymorphic site; whereas, the presence of a mismatch signal in the spectrum in the test spectrum is indicative of the target including the second base at the polymorphic site. Similar approaches can be used when there are more than two allelic forms.

Certain methods include the use of arrays. An array includes multiple elements, each element including a continuous transmission line and a nucleic acid probe (or plurality of probes) that are electromagnetically coupled to the continuous transmission line located within the element. The elements are contacted with a sample containing a nucleic acid target. A response signal is then detected for those elements in which a hybridization complex is formed.

Utilizing this general approach, arrays can be used to rapidly detect the presence of multiple targets in a sample. For instance, in a sample potentially containing a first target of known sequence and a second target of known sequence, nucleic acid probes are selected such that a first set of probes is complementary to the first target and a second set of probes is complementary to a second target. The first and second set of probes are typically located at a first and second element, respectively. Detection of a response signal from the first element is indicative of the sample including the first target; similarly, a response signal from the second element is indicative of the sample including the second target. Through appropriate selection of the sequence of probes in the various elements, these methods can be used to distinguish between SNPs, to determine which genes are expressed in a particular cell, (i.e., to conduct an expression analysis) and to determine the sequence of a nucleic acid.

The present invention also provides methods for obtaining quantitative information on nucleic acid hybridization events. In general, such methods typically include contacting a nucleic acid probe electromagnetically coupled to a portion of a signal path with a sample that includes a nucleic acid target, whereby a hybridization complex is formed between the probe and target. Changes in a signal or set of signals that are characteristic of the hybridization complex are then monitored. In certain methods, changes in signal amplitude or frequency are measured at different time points to obtain multiple measured values. The multiple values can be utilized, for example, to calculate kinetic parameters.

DESCRIPTION OF THE SPECIFIC EMBODIMENTS

I. Definition of Terms

Figure 1A:
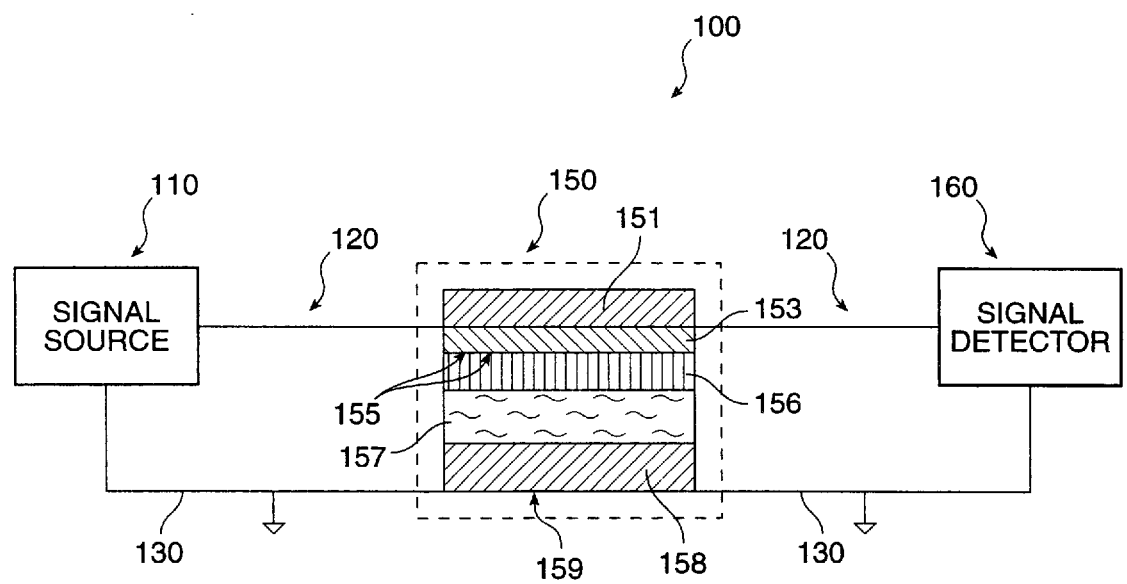
FIG. 1A illustrates one embodiment of the bio-assay system in accordance with the present invention.

The terms "binding partners" or "ligand/antiligand" or "ligand/antiligand complex" refer to molecules that specifically recognize (e.g., bind) other molecules to form a binding complex such as antibody-antigen, lectin-carbohydrate, nucleic acid-nucleic acid, biotin-avidin, etc. Biological binding partners need not be limited to pairs of single molecules. Thus, for example, a single ligand may be bound by the coordinated action of two or more "antiligands".

"Ligand" or "analyte" refers to any molecule being detected. It is detected through its interaction with an antiligand, which specifically or non-specifically binds the ligand, or by the ligand's characteristic dielectric properties. The ligand is generally defined as any molecule for which there exists another molecule (i.e., an antiligand) which specifically or non-specifically binds to the ligand, owing to recognition of some portion of the ligand. The antiligand, for example, can be a nucleic acid probe and the ligand a nucleic acid target which is complementary to the probe.

"Antiligand" generally refers to a molecule which specifically or nonspecifically binds another molecule (i.e., a ligand). The antiligand is also detected through its interaction with a ligand to which it specifically binds or by its own characteristic dielectric properties. As used herein, the antiligand is usually immobilized on the surface, either alone or as a member of a binding pair that is immobilized on the surface. In some embodiments, the antiligand may consist of the molecules on the signal path or conductive surface. Alternatively, once an antiligand has bound to a ligand, the resulting antiligand/ligand complex can be considered an antiligand for the purposes of subsequent binding. In the instance of nucleic acid analyses, the antiligand typically is a nucleic acid probe of known sequence which hybridizes with a nucleic acid target of unknown sequence.

The term "signal path" refers to a transmission medium along the bio-electrical interface which is capable of supporting an electromagnetic signal of any useful frequency including a DC static field. A non-exhaustive list of signal paths include conductive and dielectric waveguide structures, multiple-conductor transmission mediums such as transverse electromagnetic (TEM) transmission lines, transmission lines with three or more conductive elements which support TE, TM or TEM mode propagation such as quadrupolar and octupolar lines, coupled waveguides, resonant cavity structures which may or may not be coupled, other non-modal structures like wires, printed circuits, and other distributed circuit and lumped impedance conductive structures, and the like. The signal path may structurally comprise the signal plane, the ground plane, or a combination of both structures. Typically, the signal path is formed along a direction which is non-orthogonal to the surface of the molecular binding region. In embodiments in which the signal path consists of a conductive layer or region, the conductive region extends continuously over that range. In embodiments in which the signal path is non-metallic, i.e., a dielectric waveguide, the signal path is defined as the path having the least amount of signal loss or as having a conductivity of greater than 3 mhos/m.

A "transmission line" is a conductive element that can support the propagation of an electromagnetic signal at some predefined frequency.

The terms "molecular binding region" or "MBR" refers to a layer having of at least one molecular structure (for example, an analyte, antiligand, or a ligand/antiligand pair, etc.) coupled to the signal path along the bio-electrical interface. The molecular binding region may consist of one or more ligands, antiligands, ligand/antiligand complexes, linkers, matrices of polymers and other materials, or other molecular structures described herein. Further, the molecular binding region may be extremely diverse and may include one or more components including matrix layers and/or insulating layers, which may have one or more linking groups. The MBR is coupled to the signal path either via a direct or indirect physical connection or via electromagnetic coupling when the ligand is physically separated from the signal path. The MBR may be of a derivatized surface such as by thiol linkers biotinylated metals and the like, all in accordance with standard practice in the art.

A "binding event" generally refers to an interaction or association between a minimum of two molecular structures, such as a ligand and an antiligand. The interaction may occur when the two molecular structures are in direct or indirect physical contact or when the two structures are physically separated but electromagnetically coupled therebetween. Examples of binding events of interest in a medical context include, but are not limited to, ligand/receptor, antigen/antibody, enzyme/substrate, DNA/DNA, DNA/RNA, RNA/RNA, nucleic acid mismatches, complementary nucleic acids and nucleic acid/proteins. Alternatively, the term "binding event" may refer to a single molecule or molecular structure described herein, such as a ligand, or an antiligand/ligand complex, which is bound to the signal path. In this case the signal path is the second molecular structure.

The term "ligand/antiligand complex" refers to a complex in which the ligand is bound to the antiligand. For example, a "ligand/antiligand complex" can include a nucleic acid probe hybridized to a target nucleic acid. The binding may be specific or non-specific, and the bonds are typically covalent bonds, hydrogen bonds, immunological binding, Van der Waals forces, or other types of binding.

"Coupling" refers to the transfer of energy between two structures either through a direct or indirect physical connection or through any form of signal coupling, such as electrostatic or electromagnetic coupling. Thus, "electromagnetic coupling" refers to energy transfer through electromagnetic interactions.

The term "test signal" refers to a signal propagating at any useful frequency defined within the electromagnetic spectrum. For examples, the test signal frequency is at or above 1 MHz, such as 5 MHz 10 MHz, 20 MHz, 45 MHz, 100 MHz, 500 MHz, 1 GHz, 5 GHz, 10 GHz, 30 GHz, 50 GHz, 100 GHz, 500 GHz, 1000 GHz and frequencies ranging therebetween.

A "solution" includes a material in which a ligand resides. A non-exhaustive list of solutions includes materials in solid, liquid or gaseous states. Solid solutions may be comprised of naturally-occurring or synthetic molecules including carbohydrates, proteins, oligonucleotides, or alternatively, any organic polymeric material, such as nylon, rayon, dacryon, polypropylene, teflon, neoprene, delrin or the like. Liquid solutions include those containing an aqueous, organic or other primary components, gels, gases, and emulsions. Exemplary solutions include celluloses, dextran derivatives, aqueous solution of d-PBS, Tris buffers, deionized water, blood, physiological buffer, cerebrospinal fluid, urine, saliva, water, organic solvents. The solution is used herein to refer to the material in which the ligand and/or antiligand are applied to the binding surface. The solution contains the sample to be analyzed.

A "linking group" or "linker" means chemical structures which are used to attach any two components on the bio-assay device. The linking groups thus have a first binding portion that binds to one component, such as the conductive surface, and have a second binding portion that binds to another component such as the matrix or the antiligand.

The term "bio-assay device" refers to a structure in which the molecular binding region is formed. The bio-assay device may consist of a surface, recessed area, or a hermetically sealed enclosure, all of which may be any particular size or shape.

The term "bio-assay system" means the bio-assay device as described above, in connection with the components necessary to electromagnetically probe and detect the bio-assay device. These components include, but are not limited to, the signal path(s), substrate(s), electronic devices such as signal generators, oscilloscopes, and vector analyzers necessary to probe to and detect signals from the bio-assay device, microchips and microprocessors which can probe and detect electromagnetic signals and analyze data, and the like.

"Resonant" or "resonance" refers generally to a rapidly changing dielectric response as a function of frequency.

A "bio-electrical interface" refers to an interface structure between a signal path for supporting the propagation of a test signal and a molecular binding region.

A "matrix" or "binding matrix" refers to a layer of material on the bioassay chip that is used as a spacer or to enhance surface area available for binding or to optimize orientation of molecules for enhanced binding, or to enhance any other property of binding so as to optimize the bio-assay device. The matrix layer may be comprised or carbohydrates such as dextran, poly amino acids, cross-linked and non-cross linked proteins, and the like.

The term "specifically binds" means a binding reaction which is determinative of the cognate ligand of interest in a heterogenous population of molecules.

A "nucleic acid" is a deoxyribonucleotide or ribonucleotide polymer in either single- or double-stranded form, and unless otherwise limited, encompasses known analogs of natural nucleotides that can function in a similar manner as naturally occurring nucleotides.

A "polynucleotide" refers to a single or double-stranded polymer of deoxyribonucleotide or ribonucleotide bases.

A "probe" or "nucleic acid probe" is an nucleic acid capable of binding to a target nucleic acid of complementary sequence through one or more types of chemical bonds, usually through complementary base pairing, usually through hydrogen bond formation, thus forming a duplex structure. A probe may include natural bases (i.e., A, G, C, or T) or modified bases (e.g., 7-deazaguanosine, inosine, etc.). A probe can be an oligonucleotide which is a single-stranded DNA. Oligonucleotide probes can be synthesized or produced from naturally occurring polynucleotides. In addition, the bases in a probe can be joined by a linkage other than a phosphodiester bond, so long as it does not interfere with hybridization. Thus, probes may be peptide nucleic acids in which the constituent bases are joined by peptide bonds rather than phosphodiester linkages (see, for example, Nielsen et al., Science 254, 1497–1500 (1991)). Some probes may have leading and/or trailing sequences of noncomplementarity flanking a region of complementarity.

A "perfectly matched probe" has a sequence perfectly complementary to a particular target sequence. Such a probe is typically perfectly complementary to a portion (subsequence) of the target sequence.

The term "mismatch probe" refer to probes whose sequence is not perfectly complementary to a particular target sequence and, in some instances, deliberately selected not to be perfectly complementary. Although the mismatch (s) may be located anywhere in the mismatch probe, terminal mismatches are less desirable as a terminal mismatch is less likely to prevent hybridization of the target sequence. Thus, probes are often designed to have the mismatch located at or near the center of the probe such that the mismatch is most likely to destabilize the duplex with the target sequence under the test hybridization conditions.

"Hybridization" refers to binding between a nucleic acid probe and a target sequence via complementary base pairing; the resulting complex is referred to as a "hybridization complex". A hybridization complex may be either a complementary complex or a mismatch complex.

A "complementary complex" is a hybridization complex in which there are no mismatches between the probe and target sequences that comprise the complex.

A "mismatch complex" is a hybridization complex in which there are one or more mismatches between the probe and target sequences that comprise the complex.

"Substantially complementary" means that the sequence of the target is not exactly complementary to the sequence of the probe; however, there is sufficient complementarity that a mismatch complex can form.

"Specific hybridization" refers to the binding, duplexing, or hybridizing of one nucleic acid molecule only to a particular nucleotide sequence under stringent conditions when that sequence is present in a complex mixture (e.g., total cellular) DNA or RNA.

"Stringent conditions" are conditions under which a probe will hybridize to its target subsequence, but to no other sequences. Stringent conditions are sequence-dependent and are different in different circumstances. A variety of factors may significantly affect the stringency of hybridization, including, among others, base composition, size of the complementary strands, the presence of organic solvents and the extent of base mismatching; the combination of parameters is more important than the absolute measure of any one. For a discussion of general factors influencing hybridization, see for example, WO 93/02216 and Watson et al., Recombinant DNA, $2^{nd}$ Edition, Scientific American Books, NY 1992, each of which is incorporated herein by reference in its entirety. An extensive guide to hybridization of nucleic acids is found in Ausubel et al., Current Protocols in Molecular Biology, Greene Publishing Associates, Inc. and John Wiley and Sons, Inc. (supplemented through 1998), which is also incorporated herein by reference in its entirety.

Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide or tetraalkyl ammonium salts. For example, conditions of 5×SSPE (750 M NaCl, 50 mM NaPhosphate, 5 mM EDTA, pH 7.4) and a temperature of 25–30° C. are typically suitable for allele-specific probe hybridizations. Stringency can be determined empirically by gradually increasing the stringency of the conditions (e.g., increasing salt, raising temperature, etc.) until the desired level of specificity is obtained.

A "polymorphism" refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as a the "reference form" or the "wild type form" and other allelic forms are designated as "alternative alleles" or "variant alleles." The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A "single nucleotide polymorphism" occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

A "sample" refers to essentially any source from which nucleic acids can be obtained. A sample may be acquired from essentially any organism, including animals and plants, as well as cell cultures, recombinant cells and cell components. Samples can be from a biological tissue, fluid or specimen and may be obtained from a diseased of healthy organism. Samples may include, but are not limited to, sputum, amniotic fluid, blood, blood cells (e.g., white cells), tissue or fine needle biopsy samples, urine, peritoneal fluid, pleural fluid, or cells therefrom. Samples may also include sections of tissues such as frozen sections taken for histological purposes. Typically, samples are taken from a human. However, samples can be obtained from other mammals also, including without limitation, dogs, cats, sheep, cattle, and pigs. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used.

The terms "isolated," "purified," "biologically pure," or "substantially pure" mean an object species is the predominant species present (i.e., on a molar basis it is more abundant than any other individual species in the composition), and preferably a substantially purified fraction in a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

II. Introduction

A. General

The present invention generally provides a variety of methods and apparatus for analyzing binding events between a ligand and antiligand. More specifically, the present invention provides methods for analyzing nucleic acids, especially hybridization reactions between a nucleic acid probe and a target nucleic acid, to obtain different types of genetic information. In general, the methods involve coupling a nucleic acid probe to a signal path such as a transmission line and then contacting the probe with a solution containing a target nucleic acid molecule under conditions which allow for hybridization of complementary target molecules with the nucleic acid probe. A signal is launched down the signal path followed by detection of a response signal resulting from the hybridization complex which can be used to analyze binding between the nucleic acid probe and the target. The methods of the present system can be used in a variety of nucleic. acid analyses including, but not limited to, gene expression analysis, sequence checking, single nucleotide polymorphism (SNP) analysis and de novo sequencing.

The methods of the present invention are amenable to conducting such analyses on chips which contain multiple element arrays. In certain methods, each element of the array includes a transmission line and circuitry for addressing the element. Multiple nucleic acid probes are typically attached to the transmission line in each element of the array. Similar to the case described above, a signal is launched down a plurality of transmission lines, each running to a different element of the array. The transmitted and/or reflected signal as modulated by the probe/target complex at the element is utilized to characterize the nature of binding. Using the detection system of the present invention, it is possible to distinguish between perfectly complementary binding and binding involving mismatches.

Some methods involve determining a profile or fingerprint of a particular hybridization complex. These profiles are useful in distinguishing between complementary and mismatch complexes and detecting the presence of particular targets in a sample, for example.

B. The Bio-Assay System

The present invention makes use of the finding that a vast number of molecules can be distinguished based upon the unique dielectric properties which most molecules exhibit. These distinguishing dielectric properties can be observed by coupling a signal to the bound molecular structure. The unique dielectric properties of the bound molecular structure modulate the signal, giving it a unique signal response. The unique signal response can then be used to detect and identify the ligands and other molecules which make up the molecular binding region. Although the following description of the system is often described with reference to ligands and antiligands because of its broad applicability, it should be understood that the ligands and antiligands can specifically include nucleic acids such as probes and targets. Similarly, although reference is broadly made to binding events, such events can include hybridization between nucleic acids.

FIG. 1A illustrates a bio-assay system 100 in accordance with the present invention. The system 100 is illustrated in a two conductor, signal-plane ground-plane, circuit topology which may be realized in a multitude of architectures including lumped or distributed element circuits in microstrip, stripline, coplanar waveguide, slotline or coaxial systems. Moreover, those of skill in the art of electronics will readily appreciate that the system may be easily modified to a single conductor waveguide system, or a three or more conductor system.

As illustrated, the system 100 includes a signal source 110, transmission lines 120, a source/detector ground plane 130, a bio-assay device 150, and a signal detector 160. The illustrated embodiment shows two transmission lines 120 coupled to the bio-assay device 150, although in alternative embodiments a single transmission line may be coupled to the bio-assay device, or, further alternatively, three or more transmission lines may be coupled to the bio-assay device 150. Transmission lines 120 are formed from a material which can support the propagation of a signal over the desired frequency of operation. Transmission lines 120 are realized as a conductive layer, such as gold, deposited on a substrate, such as alumina, diamond, sapphire, polyimide, or glass using conventional photolithography or semiconductor processing techniques.

The system 100 further includes a bio-assay device 150 coupled to the transmission lines 120. The bio-assay device 150 contains a supporting substrate 151 onto which an interface transmission line is disposed. The interface transmission line 153 forms an interface for supporting the propagation of a test signal. The supporting substrate 151 may consist of any insulating material such as glass, alumina, diamond, sapphire, silicon, gallium arsenide or other insulating materials used in semiconductor processing.

A molecular binding region (MBR) 156 is coupled to one or more areas of the interface transmission line 153. As those of skill in the art of electronics will appreciate, coupling may occur either through a direct connection between the interface transmission line 153 and MBR 156 as illustrated, or alternatively through signal coupling, further described below.

The MBR 156 is primarily composed of one or more ligands, although other molecules and structures may also be included, as described herein. The MBR 156 may consist of only one bound ligand tier, for instance in the case of primary binding, or it may consist of two, three, four, five or more bound ligand tiers, in the instances where there are secondary or higher-order binding events occurring. Multiple ligand tiers may occur at different binding surfaces 155 over the same interface transmission line 153.

In the illustrated embodiment, dielectric substrate 158 is located between solution 157 and a bio-assay device ground plane 159. In the illustrated embodiment, dielectric layer 158 and bio-assay device ground plane 159 are located within the bio-assay device 150, although in alternative embodiments, one or both may be located externally. Furthermore, the MBR 156 and solution 157 arrangement may be switched and moved towards the bio-assay device ground plane alternatively, or in addition to the proximity of these layers to the interface transmission line 153.

The system 100 includes a signal source 110 which launches the test signal onto the transmission line 120 and towards the bio-assay device 150. A signal detector 160 is positioned along the transmission path to detect the resulting signal (either reflected or transmitted or both). When the signal propagates along the interface transmission line 153 of the bio-assay device 150, the dielectric properties of the MBR 156 modulates the test signal. The modulated signal can then be recovered and used to detect and identify the molecular binding events occurring within the bio-assay device, further described below.

In an alternative embodiment of the invention, detection and identification of a ligand, antiligand/ligand complex (e.g., a hybridization complex between a probe and a complementary target) or other molecular structure described herein is possible when it is physically separated from the interface transmission line 153. In this embodiment, the ligand is not physically connected to the transmission line 153 but is electrically or electromagnetically coupled to the interface transmission line 153. The coupling between the interface transmission line 153 and the suspended ligand will alter the response of the test signal propagating along the interface transmission line 153, thereby providing a means for detecting and/or identifying it. The maximum separation between the interface transmission line 153 and suspended ligand is determined by such factors as the effective dielectric constant of the medium between the interface transmission line 153 and the ligand, the total coupling area, the sensitivity of the signal detector, concentration of the ligands in solution, and the desired detection time. Separation distances are typically on the order of $10^{-1}$ m, $10^{-2}$ m $10^{-3}$ m, $10^{-4}$ m, $10^{-5}$ m, $10^{-6}$ m, $10^{-7}$ m, $10^{-8}$ m, $10^{-9}$ m, $10^{-10}$ m or range anywhere therebetween.

Figure 1B:
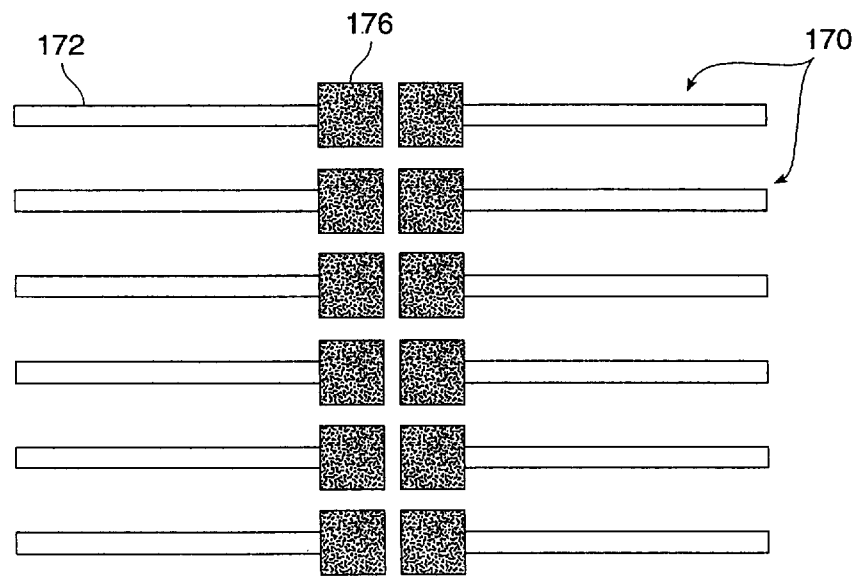
FIG. 1B illustrates a second embodiment of the bio-assay system in accordance with the present invention.

FIG. 1B illustrates a second embodiment of the bio-assay system comprising an array of resonant microstrip circuits 170. Each resonant circuit 170 consists of a transmission line 172 terminating in an open-circuited stub 176. Those skilled in the art of circuit design will appreciate that other resonant structures may be employed in lumped element or distributed circuit topologies, or combinations thereof.

Figure 1C:
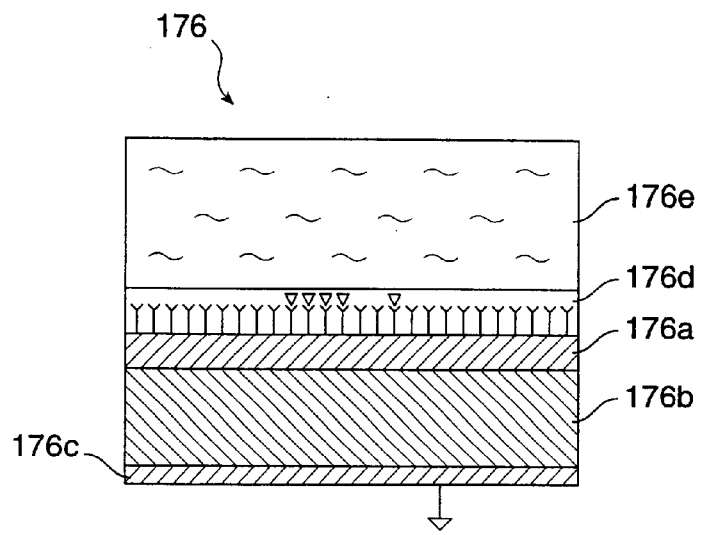
FIG. 1C illustrates a cross-section view of the bio-assay system shown in FIG. 1B.

FIG. 1C illustrates a cross-section view of one resonant circuit 170. The open-circuited stub 176 forms the bio-electrical interface of the resonant circuit 170 and closely parallels the bio-electrical interface shown in FIG. 1A. In particular, the open-circuited stub 176 consists of an interface transmission line 176a deposited on a dielectric layer 176b, and is positioned above ground plane 176c.

In this embodiment, the MBR 176d is coupled via a direct connection to transmission line 176a. The MBR 176d can bind along the interface transmission line in a specific or non-specific manner. As above, the subject molecular structure may be suspended from, but electrically coupled or electromagnetically coupled, to the interface transmission line 176a to provide binding event detection and identification information.

The dimensions of the interface transmission line 176a are influenced by considerations such as the desired measurement time (a larger area resulting in faster detection time), the desired resonant frequency fres, certain impedance matching conditions to achieve higher efficiency or cause discontinuities to highlight binding events, and the process by which the entire array is formed. For instance, if conventional . microwave photolithography is used, the binding surface area may range from $10^{-1}$ m$^2$ to $10^{-6}$ m$^2$ using a relatively thick dielectric layer such as alumina, diamond, sapphire, duriod or other conventional substrate materials. Alternatively, if semiconductor processing is used, the binding surface area may range from $10^{-6}$ m$^2$ to $10^{-12}$ m$^2$ using a relatively thin dielectric layer of silicon or gallium arsenide.

Using conventional microwave design techniques or CAD tools such as Microwave Spice™, EEsof Touchstone™ and Libra™, the length and impedance of the transmission line 172, the dimensions of the interface transmission line 176a, and the thickness and dielectric constant of the dielectric layer 176b can be selected such that the resonant structure exhibits a resonant signal response at a desired resonant frequency point $f_{res}$. The desired resonant frequency $f_{res}$ point is typically the frequency range over which the molecules of interest exhibit a dramatic change in their dielectric properties, the measurement of which will enable their detection. Alternatively, the resonant frequency point $f_{res}$ can be defined as the center of the desired test frequency range to allow for the widest range of signal detection. In the illustrated embodiment, the resonant frequency $f_{res}$ includes 10 MHz, 20 MHz, 45 MHz, 100 MHz, 500 MHz, 1 GHz, 5 GHz, 10 GHz, 30 GHz, 50 GHz, 100 GHz, 500 GHz, 1,000 GHz or frequencies ranging therebetween.

During measurement, the solution 176e is applied over one or more of the open-circuited stubs 172. A MBR 176d is formed when one or molecules within the solution bind to the interface transmission line 176a. In this instance, the MBR 176d and the solution electrically behave as a parasitic circuit, further described below, which causes the resonant frequency point $f_{res}$ to shift above or below its original resonant frequency point. This shift in frequency can be detected, and is used to indicate the occurrence of a molecular binding event. The signal response may also be interrogated over a wide spectrum to ascertain the identity of the bound molecular structure, as described below. Each resonant circuit 170 may be fabricated to bind different molecular structures and each resonant circuit 170 be made addressable, thereby permitting simultaneous detection and identification of a large numbers of molecular structures within the same solution. In an alternative embodiment, each resonant circuit 170 may be designed to exhibit a distinct resonant frequency, in which case all of the resonant circuits 170 may be interrogated over a continuous frequency spectrum to determine molecular binding.

The bio-electrical interface region consists of a signal path designed to support the propagation of an electromagnetic signal at the desired test frequency. Many configurations are possible, one example being a sputtered gold transmission line operable between D.C. and 110 GHz. In another embodiment, the signal path consists of a dielectric medium, such as the MBR itself. In this embodiment, the signal path blocks DC voltages and currents but otherwise supports the propagation of the desired test signal, occurring at frequencies, for instance 1 MHz, 5 MHz 10 MHz, 20 MHz, 45 MHz, 80 MHz, 100 MHz, 250 MHz, 500 MHz, 750 MHz, 1 GHz, 2.5 GHz, 5 GHz, 7.5 GHz, 10 GHz, 12 GHz, 18 GHz, 20 GHz, 22 GHz, 24 GHz, 26 GHz, 30 GHz, 33 GHz, 40 GHz, 44 GHz, 50 GHz, 80 GHz, 96 GHz, 100 GHz, 500 GHz, 1000 GHz, or frequencies ranging therebetween. Accordingly, the signal path is designed using high frequency circuit design techniques, known in the art. Such design techniques include impedance matching the signal path to the interconnecting structures, minimizing the insertion loss of the signal path, and minimizing the Voltage Standing Wave Ratio (VSWR) of the signal path. In the preferred embodiment of the present invention, the signal path and MBR are oriented in a non-orthogonal orientation.

The present invention is not limited to the detection of a molecule of an anticipated size or structure attached to the signal path. The MBR may consist of 1, 2, 3, 4, 5, 10, 20, 30, 50, 100, 1000, or more molecular lengths attached or separated from but coupled to the signal path. Further, the MBR may consist of a multiple layers of homogeneous molecules, a single but heterogeneous molecular layer or multiple heterogeneous molecular layers.

C. Transmission Line and MBR

The binding interactions of the system generally occurs within the bio-assay device, and in particular along the conductive layer (interface transmission line in FIGS. 1A–1C). The conductive layer is fabricated from materials having a morphology which is conducive to support the propagation of the high frequency test signal. The conductive surface is constructed from materials exhibiting appropriate conductivity over the desired test frequency range as well as possessing good molecular binding qualities as described above. Such materials include, but are not limited to gold, indium tin oxide (ITO), copper, silver, zinc, tin, antimony, gallium, cadmium, chromium, manganese, cobalt, iridium, platinum, mercury, titanium, aluminum, lead, iron, tungsten, nickel, tantalum, rhenium, osmium, thallium or alloys thereof. The conductive layer may also be formed from semiconducting materials which may be either crystalline or amorphous in structure, including chemically doped or pure carbon, silicon, germanium, gallium-arsenide, idium-gallium arsenide, or the like. The conductive material may also be formed from polymers especially those that are conductive such as polyacetylene, polythiophene and the like. The conductive layer may be thick or only several molecular layers in depth as the application requires. The conductive layer may be comprised of an evaporated thin metal layer or an epitaxial layer of gallium arsenide or other semiconductor materials rendered conductive through known semiconductor processing techniques. In addition, the conductive layer may be derivatized, the process by which is well known, e.g., see Kumar et al., "Patterned Self-Assembled Monolayer and Mesoscale Phenomena," Accounts of Chemical Research, 28:219–226 (1995).

The conductive layer is additionally fabricated from materials having a morphology which is conducive to molecular binding. Ligands may bind directly, indirectly through other molecular structures, or through both configurations to the conductive layer. The range of molecules that may bind to the conductive layer include, but are not limited to, proteins, nucleic acids, small molecules, saccharides, lipids, and any other molecule of interest. Binding may involve only a single species of molecules attached to the surface, a whole array of different species attached to the surface, or multiple binding events between species directly attached to the surface and ligands of interest in the solution.

In general terms, binding events in one embodiment may be described as primary binding and secondary binding. Additional layers of molecular binding may also occur. Primary binding refers to the attachment of an antiligand to the conductive surface, which can be done through the assistance of a linker molecule. Secondary binding refers to the binding of a ligand to the antiligand, which may be another molecule in the MBR or directly to the conductive surface itself. Typically, the binding involves a liquid phase ligand binding to an immobilized solid phase antiligand. For example, rimary binding can be the attachment of a nucleic acid probe to the conductive layer of the bioassay device and secondary binding can involve the binding of a complementary target molecule in a sample solution to the nucleic acid probe. Alternatively, secondary binding may be the direct attachment of a nucleic acid probe to the conductive surface, such as the amine terminus of a protein attaching directly to a gold conductive layer.

Figure 1D:
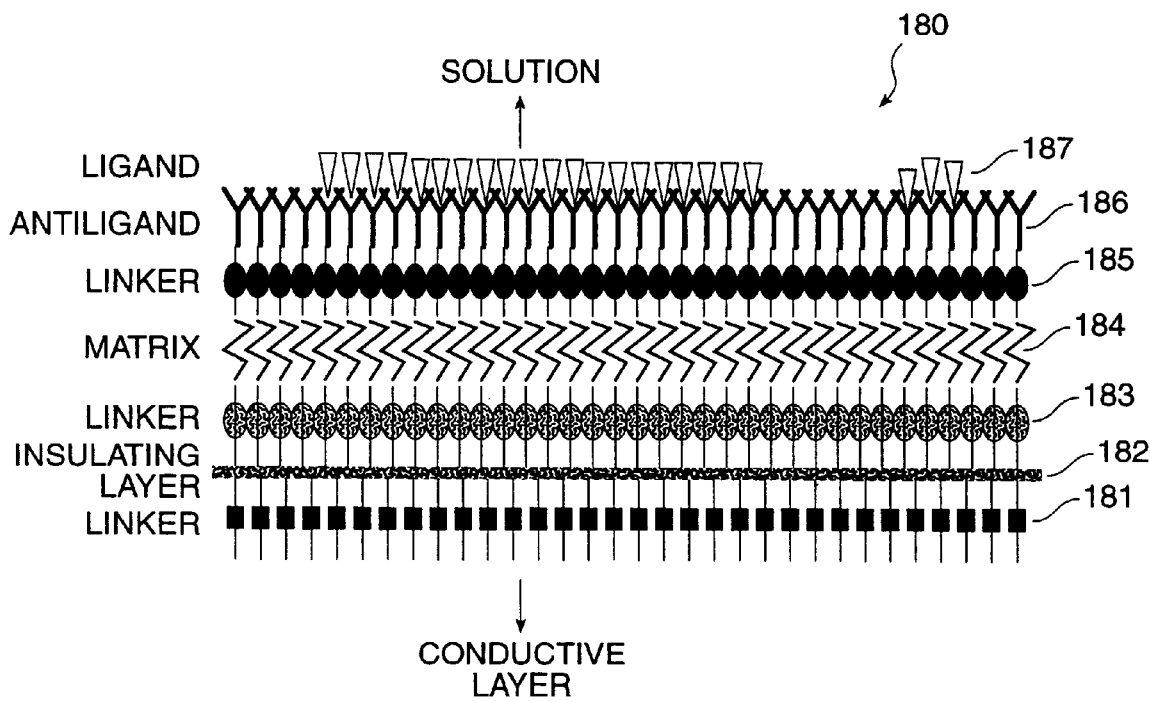
FIG. 1D illustrates one embodiment of a molecular binding region in accordance with the present invention.

The aforementioned binding results in the formation of a molecular binding region (MBR) 180 along one or more areas of the conductive layer, one embodiment of which is illustrated in FIG. 1D. In this embodiment, the MBR 180 optionally consists of a first linker 181, an insulator 182, a second linker 183, a matrix 184, a third linker 185, an antiligand layer 186, and a ligand layer 187.

First linker 181 provides attachment between insulating layer 182 and conductive layer (not shown). First linker 181 consists of molecule such as thiols, amines, amides, or metals such as chromium or titanium. Insulating layer 182 provides a barrier between the conductive layer and the MBR 180 and solution (not shown). Insulating layer 182 may provide a hermetic barrier to prevent structural deterioration of conductive layer due to exposure to the MBR and/or solution. Alternatively, or in addition, insulating layer 182 may consist of an electrically non-conductive material to prevent the flow of DC or low frequency energy from the conductive layer to the MBR and/or solution which could interfere with the measurement. The insulating layer may include polyimide, alumina, diamond, sapphire, non-conductive polymers, semiconductor insulating material such as silicon dioxide or gallium arsenide or other materials which provide hermetic and/or electrically insulating characteristics. The insulating layer may also consist of air, or another gaseous substance, in which case linker 181 may be deleted.

Second linker 183 provides attachment between the insulating layer 182 and matrix 184 and consists of the same or similar molecules as first linkers 181. Matrix layer 184 may consist of a polymer layer, but is also optionally a carbohydrate, protein, poly-amino acid layer or the like. The matrix is typically used as a spacer to enhance the surface area available for binding or to optimize orientation of molecules so as to enhance binding. For nucleic acids, typical matrix molecules include various organic polymers, carbohydrates, polypeptides and the like. Third linker 185 consists of molecules suitable for attaching the matrix layer to the antiligand 186 and may consist of the same or similar molecules as either first and/or second linkers 181 and 183.

Antiligand 186 is used to specifically or non-specifically bind the ligand 187 within solution and/or to measure physical properties of the solution, some examples of which are temperature, pH, ionic strength, and the like. Ligand 187 consists of a molecule or structure which specifically or nonspecifically binds to the antiligand 186. For instance, in the case in which the ligand 187 consists of a target nucleic acid, antiligand 186 will consist of a nucleic acid probe.

Generally, the MBR will be sufficient to interact measurably as described therein with an electromagnetic test signal along the associated signal path. Thus, essentially any MBR composition that exhibits varying dielectric properties can be analyzed. In most embodiments, the MBR will range in thickness between about 1–5 Å to 1 cm. For simple molecular binding events, the range will usually be between about 10 Å to 10,000 Å, typically between 100 Å and 5,000 Å, or 500 Å to 1,000 Å. In larger interactions (e.g., cellular) the MBR. will range between 1 $\mu$m and 100 $\mu$m, preferably 5 $\mu$m to 50 $\mu$m. With insulators, matrices and the like, the size will range significantly higher.

The embodiment of FIG. 1D is not intended to be exhaustive of all possible MBR configurations. Those of skill in the art will appreciate that a vast multiplicity of combinations making up the MBR can be designed, as dictated by the specific applications. For instance, in another embodiment, first, second and third linkers 181, 183, 185, insulating layer 182, and matrix layer 184 are not utilized, such that the MBR consists of antiligand 186 and ligand 187. Further alternatively, first linker 181 and insulating layer 182 may be deleted. Other alternative embodiments in which one or more of the described layers are deleted, or additional layers added, will be apparent to one skilled in the art.

Figure 1E:
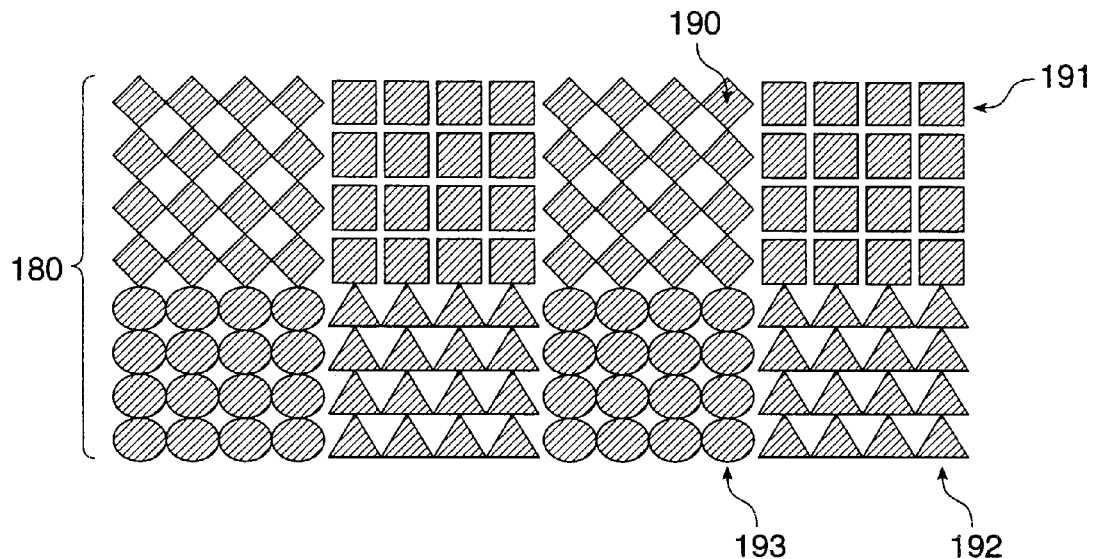
FIG. 1E illustrates one embodiment of a molecular binding region having multiple antiligands which are spatially separated in accordance with the present invention.
Figure 1F:
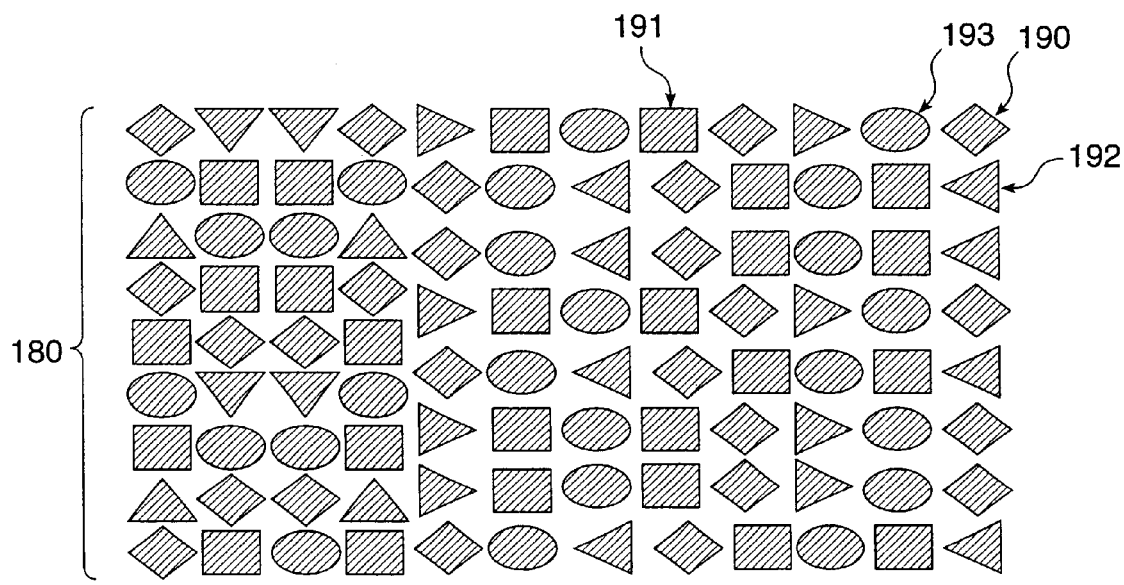
FIG. 1F illustrates one embodiment of a molecular binding region having multiple classes of antiligands in accordance with the present invention.

Further, the MBR may be composed of heterogeneous molecules which may be spatially grouped or randomly layered or distributed depending upon the particular array format. For example, FIG. 1E illustrates a top view of an MBR 180 having four different antiligands 190, 191, 192 and 193, which are spatially separated. FIG. 1F illustrates an MBR 180 in which four different antiligands 190, 191, 192 and 193 are randomly distributed throughout.

Electrically, the MBR exhibits unique dielectric properties which are in part attributable to the structural and conformational properties, and changes therein, of bound molecules, both isolated and in the presence of environmental changes such as binding events, pH changes, temperature, ionic strength and the like. The dielectric properties of the bound molecular structures, along with the local structures of the solvating medium (the solution) may also be attributable to changes in the intramolecular and intermolecular bonds caused by primary or other higher-order binding, and the displacement of the solvating medium near the conductive layer.

The bio-electrical interface region consists of a signal path designed to support the propagation of an electromagnetic signal at the desired test frequency. Many configurations are possible, one example being a sputtered gold transmission line operable between D.C. and 110 GHz. In another embodiment, the signal path consists of a dielectric medium, such as the MBR itself. In this embodiment, the signal path blocks DC voltages and currents but otherwise supports the propagation of the desired test signal, occurring at frequencies, for instance 1 MHz, 5 MHz 10 MHz, 20 MHz, 45 MHz, 80 MHz, 100 MHz, 250 MHz, 500 MHz, 750 MHz, 1 GHz, 2.5 GHz, 5 GHz, 7.5 GHz, 10 GHz, 12 GHz, 18 GHz, 20 GHz, 22 GHz, 24 GHz, 26 GHz, 30 GHz, 33 GHz, 40 GHz, 44 GHz, 50 GHz, 80 GHz, 96 GHz, 100 GHz, 500 GHz, 1000 GHz, or frequencies ranging therebetween. Accordingly, the signal path is designed using high frequency circuit design techniques, known in the art. Such design techniques include impedance matching the signal path to the interconnecting structures, minimizing the insertion loss of the signal path, and minimizing the Voltage Standing Wave Ratio (VSWR) of the signal path. In the preferred embodiment of the present invention, the signal path and MBR are oriented in a non-orthogonal orientation.

The present invention is not limited to the detection of a molecule of an anticipated size or structure attached to the signal path. The MBR may consist of 1, 2, 3, 4, 5, 10, 20, 30, 50, 100, 1000, or more molecular lengths attached or separated from but coupled to the signal path. Further, the MBR may consist of a multiple layers of homogeneous molecules, a single but heterogeneous molecular layer or multiple heterogeneous molecular layers.

III. The Bio-Assay Device

A. Device Structure

Structurally, the bio-assay device includes a signal path and a bio-electrical interface. The signal path may consist of a single input/output signal port, one input signal port path and one output port path, or multiple input and/or output signal port paths. The signal path(s) may be realized in a number of different architectures, such as a conductive wire, a transmission line, a waveguide structure, resonant cavity, or any other transmission medium that will support the propagation of the test signal over the desired frequency range. For possible embodiments, see R. E. Collins *Foundations for Microwave Engineering*, McGraw-Hill Publishing Co., 1966; and S. March, *Microwave Transmission Lines and Their Physical Realizations*, Les Besser and Associates, Inc., 1986. Further, the bio-assay device may also be realized in a variety of different configurations. Non-exhaustive configurations include large to miniaturized structures using conventional manufacturing techniques, conventional etching and photolithography, or semiconductor processing techniques.

Figure 2A:
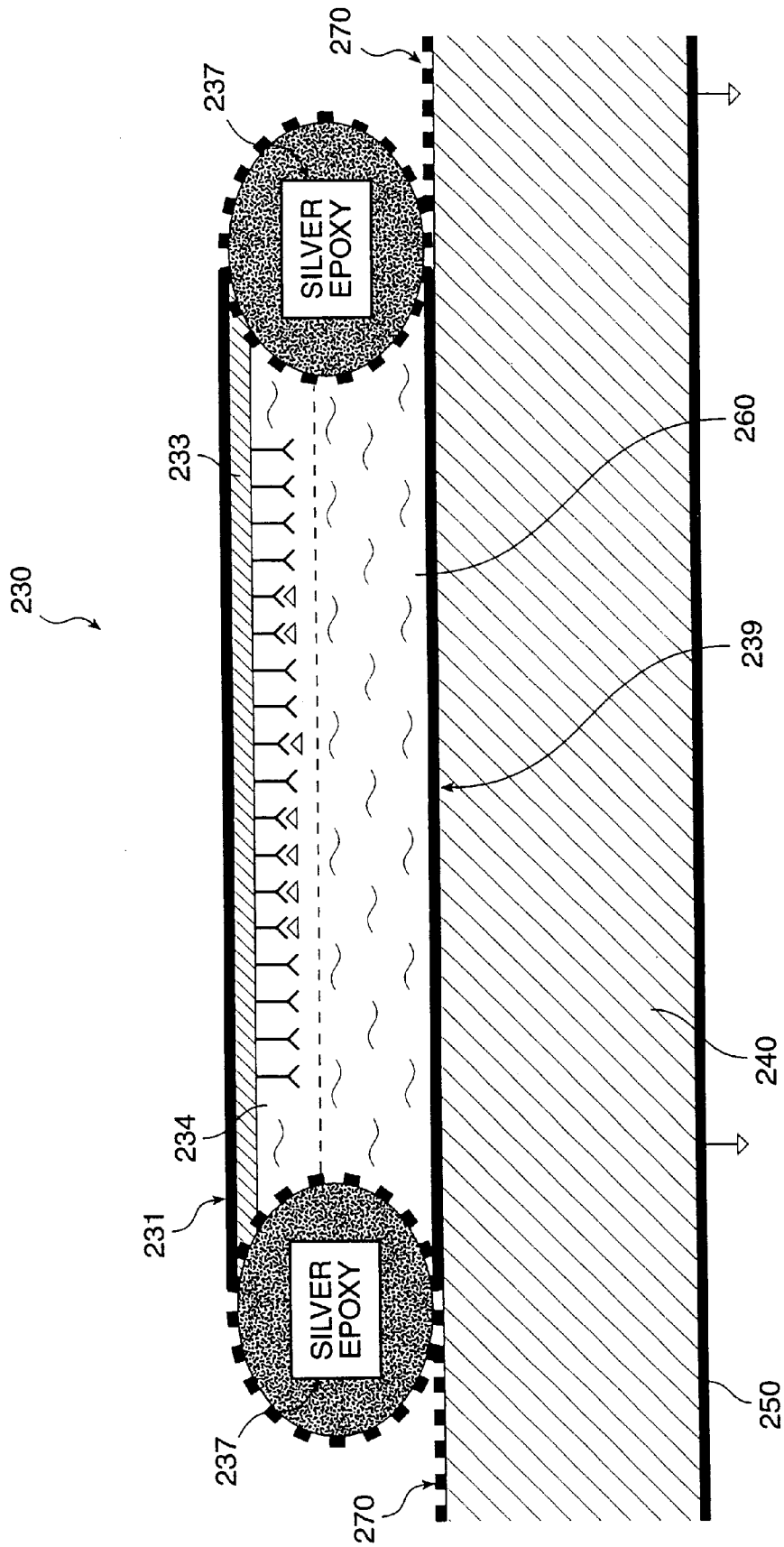
FIG. 2A illustrates one embodiment of the bio-assay device in accordance with the present invention.

FIG. 2A illustrates one embodiment of the bio-assay device as shown in cross-sectional view. The bio-assay device 230 consists of a top plate 231, contact terminals 237, and a bottom plate 239. Top plate 231 includes a bottom surface having an interface transmission line 233 disposed thereon. The dielectric substrate 240 and the ground plane 250 are located external to the bio-assay device. Top plate 231 and/or dielectric substrate 240 are formed from an insulating material, such as glass, which are preferably compatible with conventional photolithography or gold sputtering, etching or chemical vapor deposition (CVD) processing. Other materials such as alumina, silicon, gallium arsenide or other insulating materials, may alternatively be used.

As illustrated in FIG. 2A, the bottom surface of the interface transmission line 233 is in contact with the molecular binding region (MBR) 234. As illustrated, the MBR may consist of bound molecular structures of different layers or types as well as molecular structures occurring within the solution. In alternative embodiments, the MBR 234 may extend over small or large portions of the interface transmission line 233 and may consist of different bound molecular structures as shown. The MBR may consist solely of antiligand/ligand structures, or a variety intermediate of linker, matrix, and insulating layers, as shown in FIG. 1D. When implemented, the insulating layer 182 (FIG. 1D) may consist of air, polyimide, alumina, diamond, sapphire, or semiconductor insulating material such as silicon dioxide or gallium arsenide or a non-conductive material in addition to other conventional insulating materials. The thickness and dielectric constant of the insulating layer are such that the MBR 234 and the interface transmission line 233 are tightly coupled together during signal transmission. The thickness of the insulating layer 182 may be $10^{-1}$ m, $10^{-2}$ m, $10^{-3}$ m, $10^{-4}$, $10^{-5}$ m, $10^{-6}$ m, $10^{-7}$ m, $10^{-8}$ m, $10^{-9}$ m, $10^{-10}$ m or less in thickness, or values ranging therebetween, depending the amount of coupling required, the dielectric constant of the insulating layer, and the total coupling area. Coupling may be accomplished through a number of different configurations, including broadside and offset coupled configurations in multi-layer, coplanar, or waveguide circuit topologies. Implementing an insulating layer may be advantageous for hermetically sealing the interface transmission line from the solution medium and/or for preventing DC or low frequency current from flowing into the solution which could possibly disrupt molecular binding events occurring therein.

The interface transmission line 233 consists of a material which is capable of supporting signal propagation and which is capable of binding the MBR 234. The material will vary depending upon the makeup of the MBR, but some will include gold, indium tin oxide (ITO), copper, silver, zinc, tin, antimony, gallium, cadmium, chromium, manganese, cobalt, iridium, platinum, mercury, titanium, aluminum, lead, iron, tungsten, nickel, tantalum, rhenium, osmium, thallium or alloys thereof. Alternatively, the interface transmission line 233 may include one or more molecular structures (antiligands) (which forms a part of the MBR 234) for forming bonds with one or more targeted molecules (ligands). The material comprising the interface transmission line may also be chosen to promote the attachment of linkers as well as to support signal propagation. Other materials that can be used to form the interface transmission line 233 will be readily apparent to those of skill in the art.

The ligands may be transported to the MBR 234 using a solution 260, such as various buffered solutions (for example, Dulbecco's phosphate-buffered saline (d-PBS)). The ligand of interest, such as a nucleic acid target for example, can be applied to the binding surface using a variety of techniques such as wicking, pipeting, dipping, dropping, direct contact, capillary. action, or via various fluidic devices.

In a specific embodiment, the interface transmission line 233 is designed to provide low signal loss and close impedance matching to the external transmission lines 270. Low signal loss is achieved by fabricating the interface transmission line 233 from a conductive material, some examples being gold, copper, aluminum, indium tin oxide (ITO) or other conductive materials described above. Close impedance matching is achieved by defining the width of the interface transmission line 233 at approximately the width of external transmission lines 270, depending on the relative dielectric properties of the substrate, the solution, and the MBR. Signal continuity between the interface transmission line 232 and the external transmission lines 270 is provided via contact terminals 237. As explained above, the MBR 234 and solution medium 260 may be located proximate to the ground plane 250 alternatively, or in addition to these layer's location proximate to the interface transmission line 232.

Additional analog and/or digital circuitry in lumped element form, distributed form, or a combination of both may be included at the input and/or output ports of the bio-assay device. For instance, impedance matching circuits and/or buffer amplifier circuits may be employed at the input port. Alternatively, or in addition, impedance matching circuitry and one or more output amplifiers may be implemented to further enhance the output signal. Those of skill in the art of electronics will appreciate that other types of conditioning circuitry may be used in alternative embodiments as well.

Figure 2B:
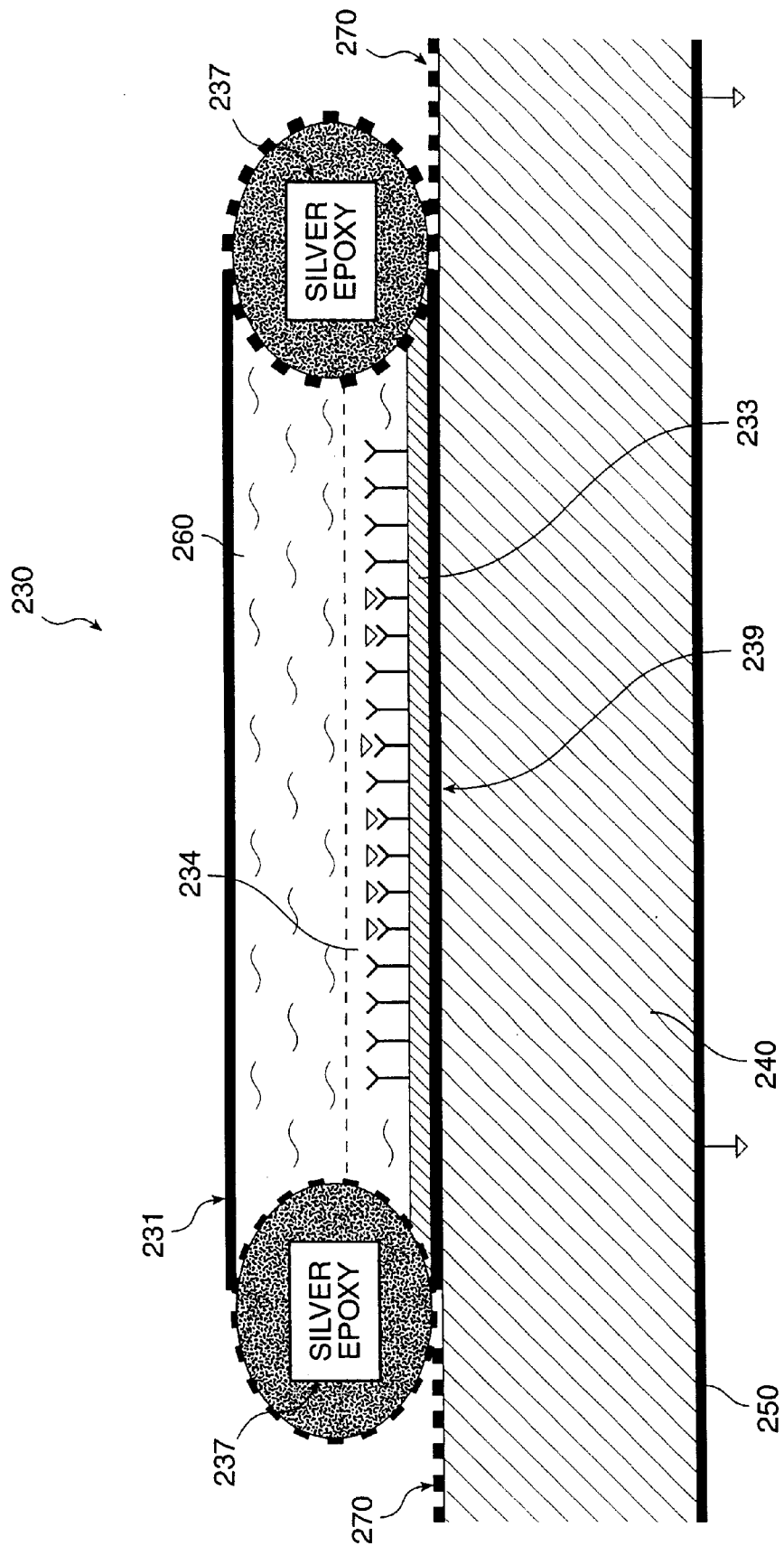
FIG. 2B illustrates a second embodiment of the bio-assay device in accordance with the present invention.

FIG. 2B illustrates a second embodiment of the bio-assay device. In this embodiment, the solution occupies a space above the interface transmission line 233 which is formed on the top surface of bottom plate 239. The top side of the interface transmission line 233 forms the binding surface to which the MBR 234 adheres. Dielectric layer 240 is positioned between interface transmission line 233 and the ground plane 250. Contact terminals 237 provide a signal path to the external transmission lines 270. The interface transmission line, top plate, bottom plate, contact terminals, and dielectric layer may be formed from the materials and the processes as described above. The MBR may also be configured as described above in FIG. 1D, or variations thereof. Further, the MBR 234 and solution medium 260 may be located proximate to the ground plane 250 alternatively, or in addition to these layer's location proximate to the interface transmission line 233.

Figure 2C:
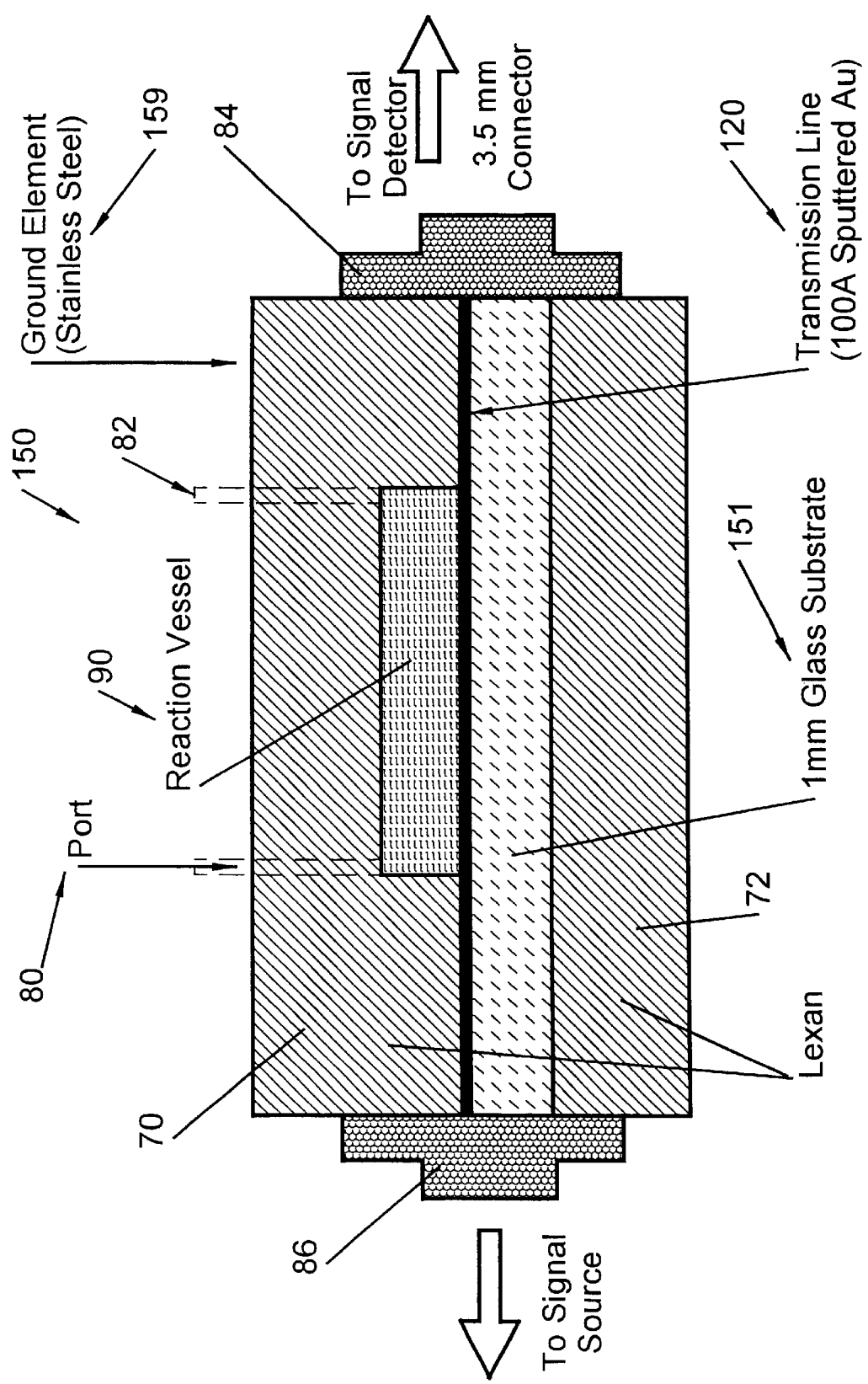
FIG. 2C is a cross-sectional view of a bio-assay device of the present invention.

FIG. 2C depicts a vertical cross-sectional view of another bio-assay device 150 of the present invention. This bio-assay device 150 comprises a two-element stripline configuration similar to that shown in FIG. 1A. The bio-assay device 150 includes a supporting substrate 151 made of glass (approximately 1 mm thick) onto the upper face of which a gold transmission line 120 is sputtered. A reaction vessel 90 (6.0 cm×1.5 cm×0.5 mm) made of LEXAN (a polycarbonate material manufactured by DuPont) is sealed to a section of the transmission line 120. The substrate 151 and attached transmission line 120, together with the reaction vessel 90 attached to the transmission line 120, are sandwiched between an upper and lower layer of a dielectric material 70, 72, respectively. In this particular embodiment, the dielectric material 70, 72, like the reaction vessel, is composed of LEXAN. The dielectric layers or spacers 70, 72 function so as to obtain the desired level of impedance in the system. Thus, other materials capable of achieving a like result can be used in place of LEXAN. In this particular embodiment, the transmission line is designed to give a nominal broadband impedance of 35Ω, and was 1.5 cm in width, 7.5 cm in length and approximately 100 Angstroms thick.

The subassembly including the glass substrate 151, transmission line 120, reaction vessel 90 and dielectric layers 70, 72 are encased in a stainless steel cover plate or ground element 159 to electromagnetically shield the transmission line 120 and provide mechanical support and pressure to keep the bio-assay device 150 sealed. A connector (e.g., a 3.5 mm connector) 84, 86 is attached at each of the two ends of the bio-assay device 150. The center pin of the connectors (not shown) is attached by conductive epoxy (not shown) to the transmission line 120 and substrate 151 with a 50$\mu$ rubber gasket. An inlet and outlet port 80, 82 extend through the cover plate 159, the upper layer of dielectric material 70 and separately connect to the reaction vessel 90, (typically at opposing ends of the reaction vessel 90.) These two ports 80, 82 allow solutions to be flowed into and out of the reaction vessel 90.

The bio-assay device 150 can then be connected via one connector 84 to an analyzer or detector (not shown) capable of measuring S-parameters from 45 MHz to 40 GHz. The other connector 86 is connected to the signal source (not shown).

Additional structural embodiments include bio-assay devices having multi-element transmission lines, waveguides, and resonant cavities, in which the MBR may be attached to one or more of the line or cavity elements in such a way as to enhance detection specificity and sensitivity. Examples of such structures include parallel arranged signal combiners, resonant cavities, or waveguides along which the bound MBR on one element alters the signal propagation properties as compared to another parallel element without the bound structure, and thus serve to change the mode properties of the combined signal, resulting in readily detectable output signal properties. These latter effects make use of well-known techniques to measure frequency, frequency stability, and very small changes in the frequency with ultra-high precision.

B. Binding Surface

Figure 3:
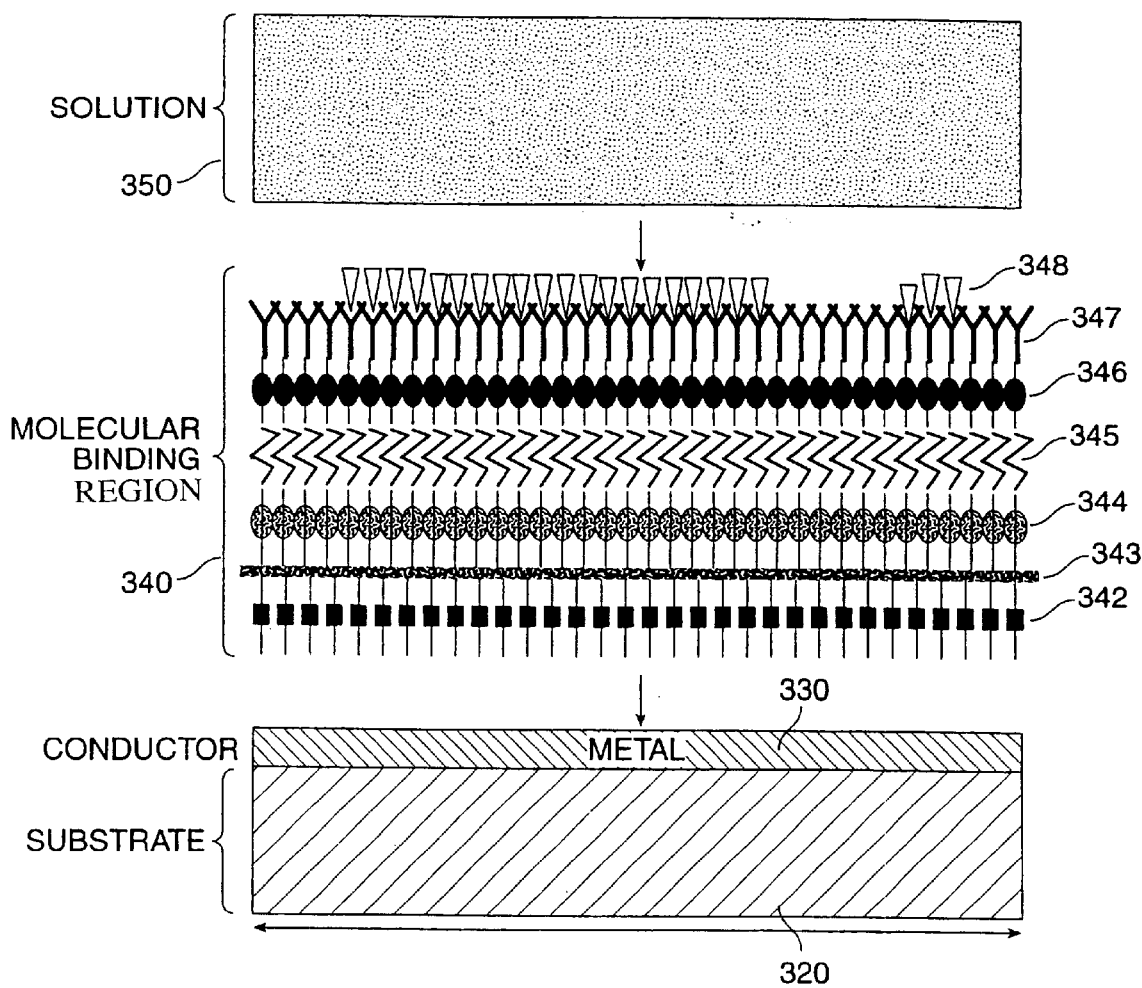
FIG. 3 illustrates one embodiment of the binding surface chemistry which occurs along the conductive layer of the bio-electrical interface.

FIG. 3 illustrates one embodiment of the binding surface chemistry which occurs along the conductive layer of the bio-electrical interface. The bio-electrical interface includes a substrate 320, a conductive layer 330, a MBR 340, and solution 350. The substrate 320 may be any of the dielectric layer or substrate materials described herein including alumina, diamond, sapphire, plastic, glass and the like and may provide structural support to the conductive layer 320. In an alternative embodiment, substrate 320 is removed and structural support is provided via insulating layer 342.

The conductive layer 330 consists of a material having a morphology which promotes signal propagation over the desired frequencies and which promotes binding of the MBR 340, as described above. In a two-conductor circuit topology, conductive layer 330 may comprise the signal plane or the ground plane. In either case however, a second conductive layer (either the signal plane or the ground plane, not shown) is located either below the substrate 320 (the arrangement of FIG. 2B) or at least one substrate layer removed from the solution 350 (an inverted arrangement of FIG. 2A). Alternatively, conductive layers may be positioned at both of these levels.

Solution 350 is coupled to the MBR 340 for permitting the flow of ligands to the MBR 340. Ligand flow from solution 350 to MBR 340 may directionally or non-directional. Solution consists of any transporting medium such as gases, ligius, or solid phase materials, some examples being aqueous d-PBS, Tris buffer, phosphate buffers, and the like.

Along the bio-electrical interface, the MBR is positioned between at least a portion of the solution and the signal path, such that the MBR is more proximate to the signal path than the solution along that portion. In the embodiment of FIG. 3, the MBR 340 is positioned between the solution 350 and the conductive layer 330, closer in proximity to the latter. In one embodiment (shown in FIG. 2A), the solution is positioned between the signal and ground planes. In a second embodiment (shown in FIG. 2B), the solution is positioned outside of the signal-ground plane region.

The MBR may consist of a ligand, ligand/antiligand complex, or other molecular structures as described herein. Typically, the ligand will be functionally intact, as close to the surface as possible, and the surface density of the antiligand will be high enough to provide the greatest dielectric effect, but not so high as to impair the function of binding, such as by steric hindrance or physically blocking the active binding site of the immobilized antiligand by neighboring molecules.

Ligands may bind specifically or non-specifically either directly to the conductive layer 320 or intermediate structures as shown in FIG. 3. If specifically bound ligands are desired, a linker is optionally used to facilitate the binding, for example to bind all proteins such that conductive layer 320 is exposed to solution. Substances may be applied to the conductive layer 320 in a number of ways, including photolithography, semiconductor processing, or any other conventional application techniques.

In addition, some ligands and antiligands may be able to bind in multiple ways. These ligands typically have a statistically predominant mode of binding or may be engineered to bind in a site-specific way. Some antiligands optionally bind the surface in a site-specific manner. For example, an oligonucleotide might be bound at one terminus. Generally, the antiligand will be attached in a manner which will not impair the function of the antiligand, e.g., preferably at concentrations that minimize surface denaturation.

The concentration of the antiligand on the binding surface will vary, depending upon the specific analyte. For example, typical concentrations for proteins are $10^7/cm^2$, $10^8/cm^2$, $10^9/cm^2$, $10^{10}/cm^2$, $10^{11}/cm^2$, $10^{12}/cm^2$, $10^{13}/cm^2$, $10^{14}/cm^2$, $10^{15}/cm^2$, or concentrations ranging therebetween. Typical concentrations for nucleic acids are $10^7/cm^2$, $10^8/cm^2$, $10^9/cm^2$, $10^{10}/cm^2$, $10^{11}/cm^2$, $10^{12}/cm^2$, $10^{13}/cm^2$, $10^{14}/cm^2$, $10^{15}/cm^2$, $10^{16}/cm^2$, $10^{17}/cm^2$, $10^{18}/cm^2 10^{19}/cm^2$, $10^{20}/cm^2$, or concentrations ranging therebetween. Typical concentrations for analytes in whole blood range from 55M, 25M, 10M, 1M, 0.5M, $10^{-1}$M, $10^{-2}$M, $10^{-3}$M, $10^{-4}$M, $10^{-5}$M, $10^{-6}$M, $10^{-7}$M, $10^8$M, $10^{-9}$M, $10^{-10}$M, $10^{-11}$M, $10^{-12}$M, $10^{-13}$M, $10^{-14}$M, $10^{-15}$M, $10^{-16}$M, $10^{-17}$M, $10^{-18}$M, or concentrations ranging therebetween.

Enough ligand should adhere within the MBR to alter the transmission of a signal through the bio-electrical interface. The quantity of ligands adhering to the binding surface may consist of 1, 10, $10^2$, $10^3$, $10^4$, $10^5$, $10^6$, $10^7$, $10^8$, $10^9$, $10^{10}$, $10^{11}$, $10^{12}$, $10^{13}$ or more ligands, as well as any number therebetween depending upon the surface area of the conductive layer. The ligands need not be applied in predefined regions along the conductive layer since the signal responses are determined by inherent dielectric properties of the MBR as opposed to placement on the bio-assay device or chip. The MBR will generally have a surface density for smaller molecules ranging from $10^{10}$ cm$^2$ to $10^{24}$ cm$^2$, typically $10^{15}$ cm$^2$ to $10^{20}$ cm$^2$. The ligand layer may be as thin as 1 layer, but 2, 3, 4, 5 or 10 or more layers are optionally used.

Once a ligand is bound to the conductive layer, the chemistry and/or structural biology of the system comes into play. The dielectric properties of the ligand yield a signal response which is characteristic of the bound structure(s), thereby permitting binding event detection, as well as detection of other properties of interest in the structure. The unique response provided by the binding event will depend on the immobilized antiligand, its target ligand, and the rearrangement of the nearby solution molecules (such as water and free ions). The range of molecules that can bind to the surface include but are not limited to proteins, nucleic acids, small molecules, saccharides, lipids, and any other molecule of interest.

Typically, the molecules of the MBR are disposed within a solution which may consist of an aqueous solution of water, d-PBS, Tris, blood, physiological buffer, cerebrospinal fluid, urine, sweat, saliva, other bodily secretions, organic solvents, and the like. Other solutions may include gases, emulsions, gels, and organic and inorganic compounds The secondary binding reaction occurs at the MBR of the bio-assay device. A ligand in a solution is transported across the bio-assay device such that it contacts the antiligand of the binding layer. The concentration of the ligand in the solution varies and may consist of $10^{-1}$M, $10^{-2}$M, $10^{-3}$M, $10^{-4}$M, $10^{-5}$M, $10^{-6}$M, $10^{-7}$M, $10^{-8}$M, $10^{-9}$M, $10^{10}$M, $10^{-11}$M, $10^{-12}$M, $10^{-13}$M, $10^{-14}$M, $10^{-15}$M, $10^{-16}$M, $10^{-17}$M, $10^{-18}$M, $10^{-19}$M, $10^{-20}$M. When an interaction, such as binding, occurs between the ligand and the antiligand, the ligand, then optionally becomes part of the binding layer, as dictated by the chemical equilibrium characteristics of the binding event.

The MBR includes the bound ligands and may also include solution molecules. The bound ligands can be any molecule, including proteins, carbohydrates, lipids, nucleic acids, and all other molecules discussed herein. The MBR may further include a linker to aid in the binding of the antiligand to the binding surface layer.

Additionally, the interaction of the antiligand with the ligand changes the characteristic dielectric response of the binding layer with only the antiligand attached. For example, if antiligand A is the antiligand that forms the binding layer, the dielectric response of a test signal propagating along the transmission line will reflect the characteristic properties of the structure of antiligand A. When ligand B binds to antiligand A, the structure and/or dielectric properties of the binding layer will change due to the binding of A to B. The structure of A may change as B binds to it, thus providing a different signal response. The change in signal due to the binding interaction will be characteristic of the binding of A to B. Therefore, the presence of a binding interaction can be determined from the change in the signal.

Moreover, information about the type of bond or the structural and/or conformational changes upon binding is obtained by noting which parts of the signal response have changed due to the interaction. Ligand B is optionally detected and identified by the signal change upon its binding to antiligand A. The binding of ligand B to antiligand A induces a conformational change, or other change in the molecular structure or surrounding solution, in antiligand A and its environs. These changes alter the dielectric properties of the MBR, thereby altering the signal response of the test signal propagating along the signal path. The change in the test signal can be used to detect the ligand B binding event and the particulars of the change can be used to identify the ligand B. In as much as the relationship between structure and function of the molecule is known, for example in the case of enzymes, antibodies, receptors and the like, the function of the bound ligand can be deduced from its spectral identification.

In one embodiment, one type of antiligand is applied to the binding surface to form a MBR, and a ligand is applied across the MBR to detect a binding event between the two molecules. For example, the antiligand can be a plurality of nucleic acid probes having the same sequence and the ligand can be a complementary target sequence. In another embodiment, the antiligand may be a mixture (e.g., numerous nucleic acid probes having different sequences) and the ligand that is applied across the binding layer is a known analyte (e.g., a target nucleic acid of known sequence). By detecting specific changes in the signal response, the particular ligand with which the antiligand interacted can be determined due to conformational and other changes induced in the ligand or antiligand, and the spectral response resulting therefrom. Such an embodiment does not require the spatial isolation of each of the specific antiligands, but rather derives the desired level of specificity from the spectral response, so that a given binding interaction is determined by looking at the electromagnetic response rather that noting on which part of the assay the binding event took place.

In another embodiment, the antiligand may be a known molecule (e.g., a nucleic acid probe of known sequence) on the binding layer and the ligand applied across the bio-assay device as a mixture of unknowns (e.g., a mixture of various target nucleic acids having different sequences). In this case, the presence of a particular ligand is detected by the presence or absence of a particular peak or signal in the spectrum that results from passing a signal through the bio-assay device. Alternatively, the ligand can be detected due to the changes in the spectrum of the antiligand or ligand upon binding of the ligand. Such an embodiment increases the specificity of the detection over that of the binding chemistry alone, since the signal contains information about the nature of the binding event. Thus, specific binding may be distinguished over non-specific binding, and the overall specificity of detection may be greatly improved over the specificity of the chemistry alone.

The system of detection formed through use of the bioassay device provides a high throughput detection system because detection optionally occurs in real time and many samples can be rapidly analyzed. The response period is optionally monitored on a nanosecond time scale. As soon as the molecules are bound to each other, detection occurs. More time is optionally required to measure low concentrations or binding events between molecules with a low binding affinity. The actual time is optionally limited by diffusion rates. Other than these potential limitations, thousands of compounds are optionally run through the system very quickly, for example, in an hour. For example, using chip fabrication technologies, a 10,000 channel device (using some of the emerging microfluidics technologies) is possible, and with small volumes and thus short diffusion times, and kinetic measurements measuring only the beginning of the reaction, 10 million samples per hour are optionally measured. With known concentrations, the binding affinity is optionally calculated from the kinetics alone and thus the device can be probed at a very fast time scale and the affinity calculated and/or estimated from the slope of the kinetic curve. References for kinetics and affinities can be found in any standard biochemistry or chemistry text such as Mathews and van Holde, *Biochemistry*, Benjamin Cummings, New York, 1990.

C. Bio-Electrical Interface

The bio-electrical interface is the structure along which the MBR and the signal path are formed. As described above, the signal path may consist of a conductive or dielectric waveguide structure, a two conductor structure such as a conventional signal/ground plane structure, or three or more conductor structures known in the art. Generally, the thickness of the conductive region of the signal path is designed to provide minimal signal loss. For example, a typical thickness of gold transmission line is in the order of 0.1 to 1000 $\mu$m, preferably about 1–10 $\mu$m.

The signal path is formed along a direction which is non-orthogonal to the MBR. In one embodiment, the test signal propagates in parallel to a tangent on the surface on which the MBR is formed. In other embodiments, the test signal may propagate at an angle of $\pm 1°$, $\pm 2°$, $\pm 3°$, $\pm 4°$, $\pm 5°$, $\pm 10°$, $\pm 15°$, $\pm 20°$, $\pm 30°$, $\pm 40°$, $\pm 45°$, $\pm 50°$, $\pm 60°$, $\pm 70°$, $\pm 80°$, or $\pm 85°$ relative to the MBR binding surface, or any ranges therebetween. In a first embodiment, the signal path consists of a transmission line in a two conductor structure and the direction of the signal path is defined by the Poynting vector as known in the art of electromagnetics. In a second embodiment, the transmission line may consist of a conductive region or layer which extends continuously along the bio-electrical interface region. In a third embodiment, the signal path maybe defined as the path having the least amount of signal loss along the bio-electrical interface over the desired frequency range of operation. In a fourth embodiment, the signal path maybe defined as having an a.c. conductivity of greater than 3 mhos/m, i.e., having a conductivity greater than that a saline solution, typically greater than 5 mhos/m, but ideally in the range of 100 to 1000 mhos/m and greater.

Thus, certain methods of the present invention involve placing a ligand or antiligand such as a nucleic acid, for example, so that it is coupled to a signal path. In such methods, the signal transmitted along the signal path need not pass through solution, for example from one electrical contact to another. This is important because, as described more fully below, water significantly attenuates electromagnetic signals that pass through water, thereby greatly reducing the sensitivity of such methods.

The bio-electrical interface region consists of a signal path designed to support the propagation of an electromagnetic signal at the desired test frequency. Many configurations are possible, one example being a sputtered gold transmission line operable between D.C. and 110 GHz. In another embodiment, the signal path consists of a dielectric medium, such as the MBR itself. In this embodiment, the signal path blocks DC voltages and currents but otherwise supports the propagation of the desired test signal, occurring at frequencies, for instance 1 MHz, 5 MHz 10 MHz, 20 MHz, 45 MHz, 80 MHz, 100 MHz, 250 MHz, 500 MHz, 750 MHz, 1 GHz, 2.5 GHz, 5 GHz, 7.5 GHz, 10 GHz, 12 GHz, 18 GHz, 20 GHz, 22 GHz, 24 GHz, 26 GHz, 30 GHz, 33 GHz, 40 GHz, 44 GHz, 50 GHz, 80 GHz, 96 GHz, 100 GHz, 500 GHz, 1000 GHz, or frequencies ranging therebetween. Accordingly, the signal path is designed using high frequency circuit design techniques, known in the art. Such design techniques include impedance matching the signal path to the interconnecting structures, minimizing the insertion loss of the signal path, and minimizing the Voltage Standing Wave Ratio (VSWR) of the signal path. In the preferred embodiment of the present invention, the signal path and MBR are oriented in a non-orthogonal orientation.

The present invention is not limited to the detection of a molecule of an anticipated size or structure attached to the signal path. The MBR may consist of 1, 2, 3, 4, 5, 10, 20, 30, 50, 100, 1000, or more molecular lengths attached or separated from but coupled to the signal path. Further, the MBR may consist of a multiple layers of homogeneous molecules, a single but heterogeneous molecular layer or multiple heterogeneous molecular layers.

Additional details regarding the design and operation of the bio-electrical interface are set forth in copending and commonly owned U.S. application Ser. No. 09/243,194, filed Feb. 1, 1999, which has been previously incorporated herein by reference for all purposes.

V. Measurement Methodology

A. General Overview

The measurement methodology of the present invention makes use of the observation that a vast number of molecules such as nucleic acids are distinguishable from one another based upon their unique dielectric properties which include dispersion effects, resonance effects, and effects on the solution surrounding said molecules. In the present invention, when a test signal couples to the MBR, the MBR interacts with the energy of the test signal, resulting in a unique signal response. The unique signal response can then be used to detect and identify the molecules which make up the MBR.

Those of skill in the art will appreciate that most molecules exhibit variation in dielectric properties over different frequencies. For instance, a molecule may exhibit a dramatic change in its dielectric properties as a function of frequency in one or more regions of the electromagnetic spectrum. The frequency band over which the molecule exhibits a dramatic dielectric change is often referred to as the molecule's dispersion regime. Over these regimes, the molecule's dielectric constant, permittivity, dipole and/or multipole moments, and susceptibility will change dramatically as a function of frequency. These quantities are often complex, having both real and imaginary parts to account for both the magnitude and phase changes that occur in the signal response. The dispersion regimes range over various frequencies, including the RF, microwave, millimeter wave, far-infrared, and infrared frequencies.

The molecule's dielectric properties can be observed by coupling a test signal to the molecule and observing the resulting signal. When the test signal excites the molecule at a frequency within the molecule's dispersion regime, especially at a resonant frequency, the molecule will interact strongly with the signal, and the resulting signal will exhibit dramatic variations in its measured amplitude and phase, thereby generating a unique signal response. This response can be used to detect and identify the bound molecular structure. In addition, because most molecules will exhibit different dispersion properties over the same or different frequency bands, each generates a unique signal response which can be used to identify the molecular structure.

Detection and identification of molecular binding events can be accomplished by detecting and measuring the dielectric properties at the molecular level. The dielectric properties at the molecular level can be defined by the molecule's multipole moments, the potential energy of which can be represented as an infinite series as is known in the art:

$$\Phi(x) = \frac{q}{r} + \frac{p \cdot x}{r^3} + \frac{1}{2}\sum_{i,j} Q_{ij} \frac{x_i x_j}{r^5} + \ldots$$

The infinite series consists of multiple terms, each of which describes in varying degrees the molecule's dielectric properties in the presence of an electric, magnetic or an electromagnetic field. The first term is referred to as the monopole moment and represents the scalar quantity of the electrostatic potential energy arising from the total charge on the molecule. The second term or "dipole moment" is a vector quantity and consists of three degrees of freedom. The third term or "quadrupole moment" is a rank-2 tensor and describes the molecule's response over 9 degrees of freedom. In general, the $N^{th}$ term is a tensor of rank $N-1$, with $3^{N-1}$ degrees of freedom, though symmetries may reduce the total number of degrees of freedom. As one can appreciate, the higher-order moments provide greater detail about the molecule's dielectric properties and thus reveals more of the molecule's unique dielectric signature. Since the gradient of the potential results in the electric field:

$$E = -\Delta\Phi(x),$$

The field strength of the higher-order moments falls off rapidly as a function of distance and thus their contribution is difficult to measure. For instance, the field due to dipole moment falls off as $r^{-3}$ and the field due to the quadrupole moment falls off as $r^{-4}$. Thus, this approach requires close proximity between the binding molecules and test signal path and low signal loss therebetween. Since it is often the case that molecular binding event detection occurs in strongly signal-absorbing solutions, such as whole blood samples or ionic solutions, signal loss between the binding events and signal path becomes quite high and detection of the higher order moments is very difficult.

In addition, each multipole term couples to the electric field in a different way. This is demonstrated by first looking at the energy of a given electrostatic system:

$$W = \int \rho(x)\Phi(x)d^3x$$

Expanding the electrostatic potential in a Taylor Series gives $$\Phi(x) = \Phi(0) + x \cdot \nabla\Phi(0) + \frac{1}{2}\sum_i \sum_j x_i x_j \frac{\partial^3 \Phi(0)}{\partial x_i \partial x_j}$$

Since $E = -\nabla\Phi(x)$, $$\Phi(x) = \Phi(0) - x \cdot E(0) - \frac{1}{2}\sum_i \sum_j x_i x_j \frac{\partial E_j}{\partial x_i}$$

Further, for the external field, $\Delta \cdot E = 0$, so that we get $$\Phi(x) = \Phi(0) - x \cdot E(0) - \frac{1}{6}\sum_i \sum_j (3x_i x_j - r^2 \delta_{ij}) \frac{\partial E_j}{\partial x_i}$$

Inserting this back into the equation for the energy given above yields $$W = q\Phi(0) - p \cdot E(0) - \frac{1}{6}\sum_i \sum_j Q_{ij} \frac{\partial E_j}{\partial x_i}$$

This shows the manner in which each multipole term interacts with the interrogating field: The total charge q with the potential, the dipole p with the electric field, the quadrupole $Q_{ij}$ with the gradient of the electric field, etc. This illustrates the second difficulty with the detection of the higher order multipole moments: It is difficult in a bulk sample to achieve sufficient field gradients to couple to the higher order moments.

The present invention overcomes the aforementioned obstacles by implementing the described bio-electrical interface. The interface includes a MBR which is coupled along the signal path. The MBR consists of a very thin and highly inhomogeneous layer (from a dielectric standpoint), thus providing the required proximity to the electromagnetically probing structure as well as the sufficient field gradients to couple to the higher order multipole moments. These qualities enable detection of higher order moments which provide a greatly enhanced view of the molecule's dielectric properties. The positioning of the MBR proximate to the signal and/or ground planes serves to isolate the signal propagating thereon from becoming absorbed into solution, thereby reducing the signal loss and enabling the usage of higher test frequencies to more accurately detect and identify the binding events. In this manner, the present invention enables to a greater degree the recovery or the signal response including the contributions from the molecule's dipole and other higher-order multipole moments.

The ability to detect and measure molecular dipole, quadrupole, and higher order multipole moments in solution represents a significant advance in the art for a number of reasons. First, many molecules of biomedical interest have very distinct structures, and therefore distinct multipole moments. Thus, identifying the multipole moments for a given molecule reveals properties of said molecule which are unique, and thus allows identification of said molecule. Second, structure and function are intimately related in many molecules of biomedical relevance. Thus, the ability to detect properties of a given molecule which relate directly to the function of said molecule means that functionality may be monitored for whole ranges of activities. Third, the local physiologic environment often plays an important role in the structure and function of a given molecule, so that an ability to detect the physical properties described above means that molecules may be used a monitors and probes for the purpose of measuring changes in a given system. Thus, with the ability to translate complex and informative properties about molecular and cellular systems into a detectable electronic data format, whole new possibilities emerge in the areas discussed herein.

B. Detecting Bound Molecular Structures

The bio-assay device described herein enables the detection of molecular binding events occurring along the signal path. Detectable binding events include primary, secondary, and higher-order binding events. For instance, in a two-conductor bio-electrical interface having no pre-existing MBR, the molecules of the conductive layer will form the antiligands for binding to the ligands, the ligands forming the MBR. In another embodiment, the antiligand and ligand are both included in the MBR. In this embodiment, the MBR is attached to the signal path surface via linkers, matrix molecules, insulating layers or a combination of each as show in FIG. 1D.

Figure 4A:
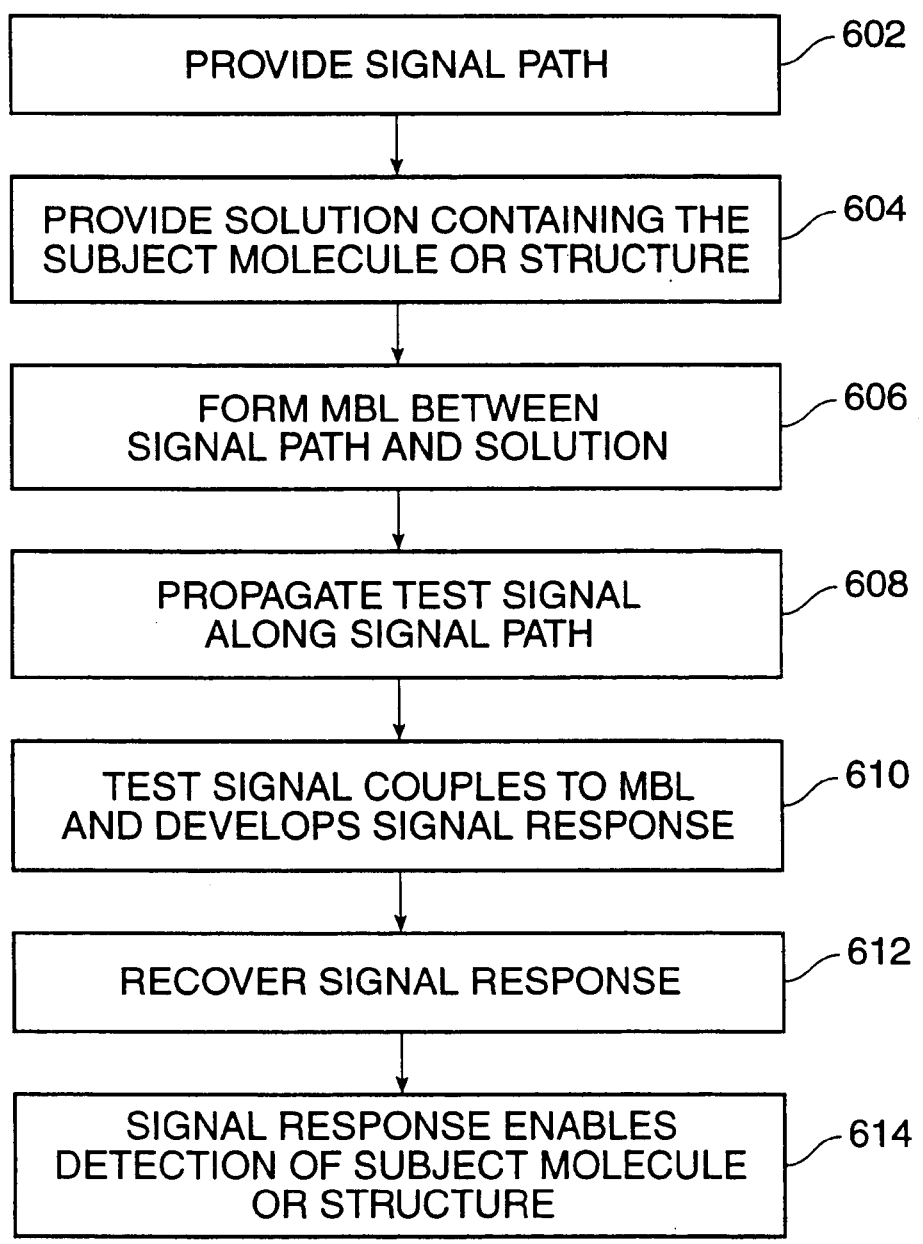
FIG. 4A illustrates one embodiment of a method for detecting molecular binding events in accordance with the present invention.

FIG. 4A illustrates one embodiment of this process. Initially at step 602, a signal path is formed from a material which can support the propagation of a signal over the desired frequency of operation. The signal path may consist of a single port path, a two port path, or a multiple port path within one of the bio-assay devices described herein. In addition, the signal path may be realized as a transmission line, resonant cavity, or as a waveguide structure.

Next at step 604, a solution is provided which contains the subject molecule or molecular structure. At step 606, a MBR consisting of the ligand is formed from the solution and is coupled between at least a portion of the signal path and the solution. Next at step 608, a test signal is propagated along the signal path. Alternatively, the test signal may be launched during the application of the solution in order to observe in real time the signal response occurring as a result of the binding events. At step 610, the test signal propagates over, couples to the MBR and develops a signal response which indicates the presence of the ligand. Next at steps 612 and 614, the test signal is recovered, the response of which indicates detection of the ligand.

The dielectric properties of the MBR may contribute to induce any number of signal responses, each of which may be indicative of molecular binding. For instance; the dispersive properties of the MBR may vary dramatically over frequency. In this instance, the test signal response will exhibit large changes in the amplitude and/or phase response over frequency when molecular binding events occur along the binding surface, thereby providing a means for detecting molecular binding events along the binding surface.

In another embodiment, the dielectric relaxation properties of the MBR will vary as a function of pulse period of the input signal. In this instance, the test signal response will indicate a change in the amount of power absorbed, or change in some other parameter of the test signal like phase or amplitude, at or near a particular pulse period. By observing a change in the absorbed power or other parameters, binding events along the binding surface may be detected. Other quantities such characteristic impedances, propagation speed, amplitude, phase, dispersion, loss, permittivity, susceptibility, frequency, and dielectric constant are also possible indicators of molecular binding events.

The above-described method may be used to detect the primary binding of an antiligand or ligand directly or indirectly along the signal path. Similarly, the process of FIG. 4A may also be used to detect secondary binding of a ligand to an antiligand. The method of FIG. 4A is not limited to detection of primary or secondary binding events occurring along the signal path. Indeed, tertiary, and higher-order binding events occurring either along the signal path or suspended in solution can also be detected using this method.

Figure 4B:
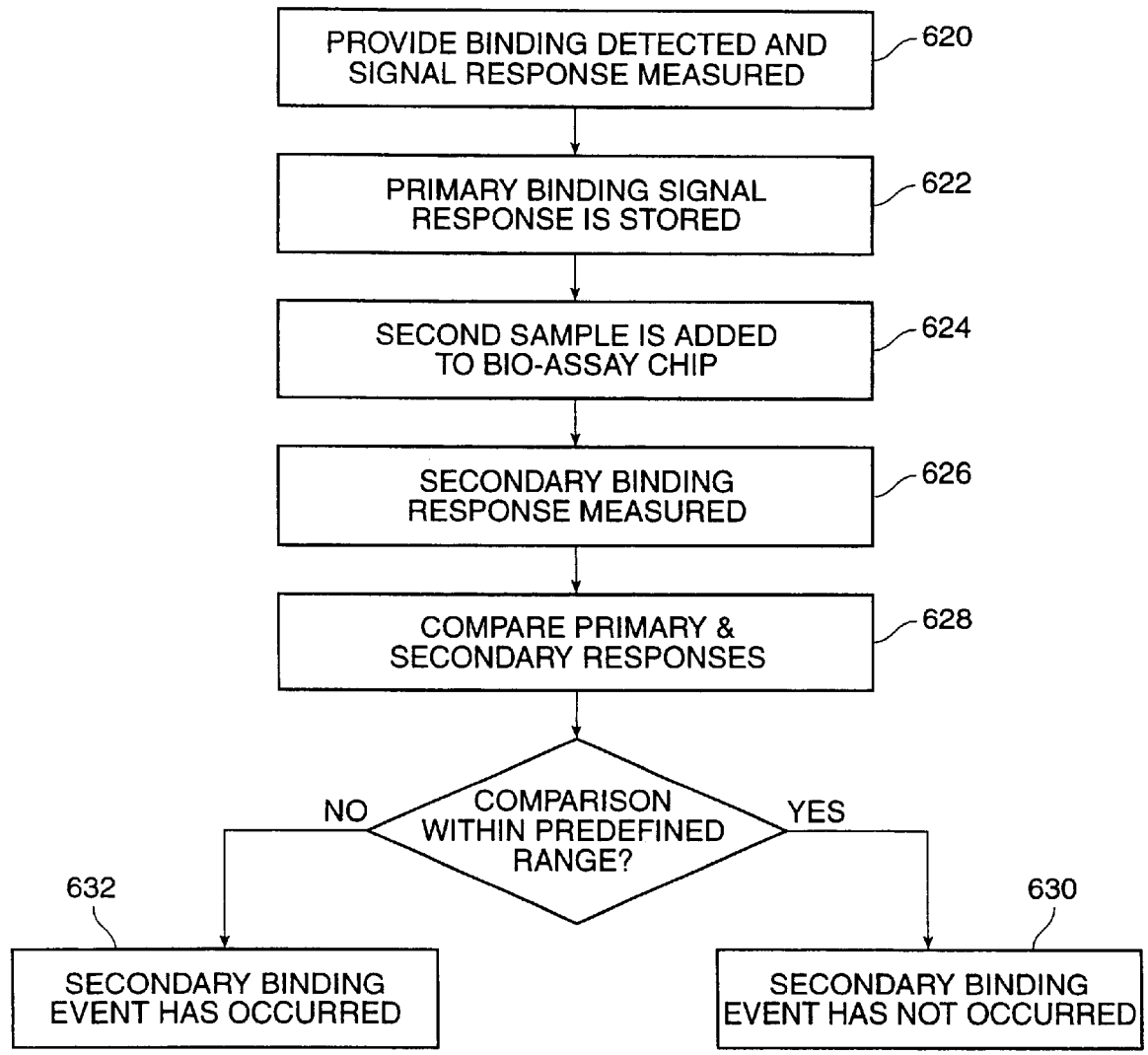
FIG. 4B illustrates one embodiment of a method for detecting secondary and higher-order binding events in accordance with the present invention.

FIG. 4B illustrates a second process for detecting secondary and higher-order binding events occurring either along the signal path. Initially at step 620, the primary binding event is detected and the signal response measured, one embodiment of which is shown in steps 602–612. Subsequently at step 622, the primary binding event signal response is stored and used as a baseline response. Next at step 624, a second molecular solution is added to the bio-assay device and allowed to circulate over the binding surface. Next at step 626, steps 608 through 612 of FIG. 4A are repeated to obtain a second signal response. Next at step 628, the second signal response and the baseline response are compared. Little or no change indicates that the two signal responses are very close, indicating that the structural and dielectric properties of the MBR have not been altered by the addition of the molecules within the new solution. In this case, secondary binding has not occurred to a significant degree (step 630). If the comparison results in a change outside of a predetermined range, the structure and/or dielectric properties of the MBR have been altered, thereby indicating secondary binding events (step 632). Quantities which can be used to indicate secondary binding events will parallel the aforementioned quantities, e.g., amplitude, phase, frequency, dispersion, loss, permittivity, susceptibility, impedance, propagation speed, dielectric constant as well as other factors. Tertiary or high-order binding events may be detected using this approach.

An alternative method of detecting secondary or higher order binding events does not required prior knowledge of the specific primary binding event. In this embodiment, the bio-assay device is designed in the assay development stage to operate with known parameters, so that whenever a pre-defined change in one of these parameters is detected, for example at the point-of-use, the binding event or events are then known to have occurred. In this embodiment, the pre-measurement of a primary binding event is not necessary, as the initial characterization has already been done either at the time of fabrication or at the time of design.

Secondary binding events can also be achieved by detecting changes in the structure of the primary bound molecule. When a molecule becomes bound, it undergoes conformational and other changes in its molecular structure relative to its unbound state. These changes affect the primary binding molecule's dielectric properties as well as inducing changes in the surrounding solution, the variation of which can be detected using steps 620–628 of FIG. 4B, described above. Quantities which can be monitored to indicate a change in the dielectric properties of the primary bound molecule include the aforementioned quantities, e.g., amplitude, phase, frequency, dispersion, loss, permittivity, susceptibility, impedance, propagation speed, dielectric constant as well as other factors.

C. Detecting Changes in the Dielectric Properties of the Molecular Binding Layer The bio-assay device described herein may also be used to measure the dielectric changes of the MBR as a result changes in temperature, pH, ionic strength and the like.

Figure 4C:
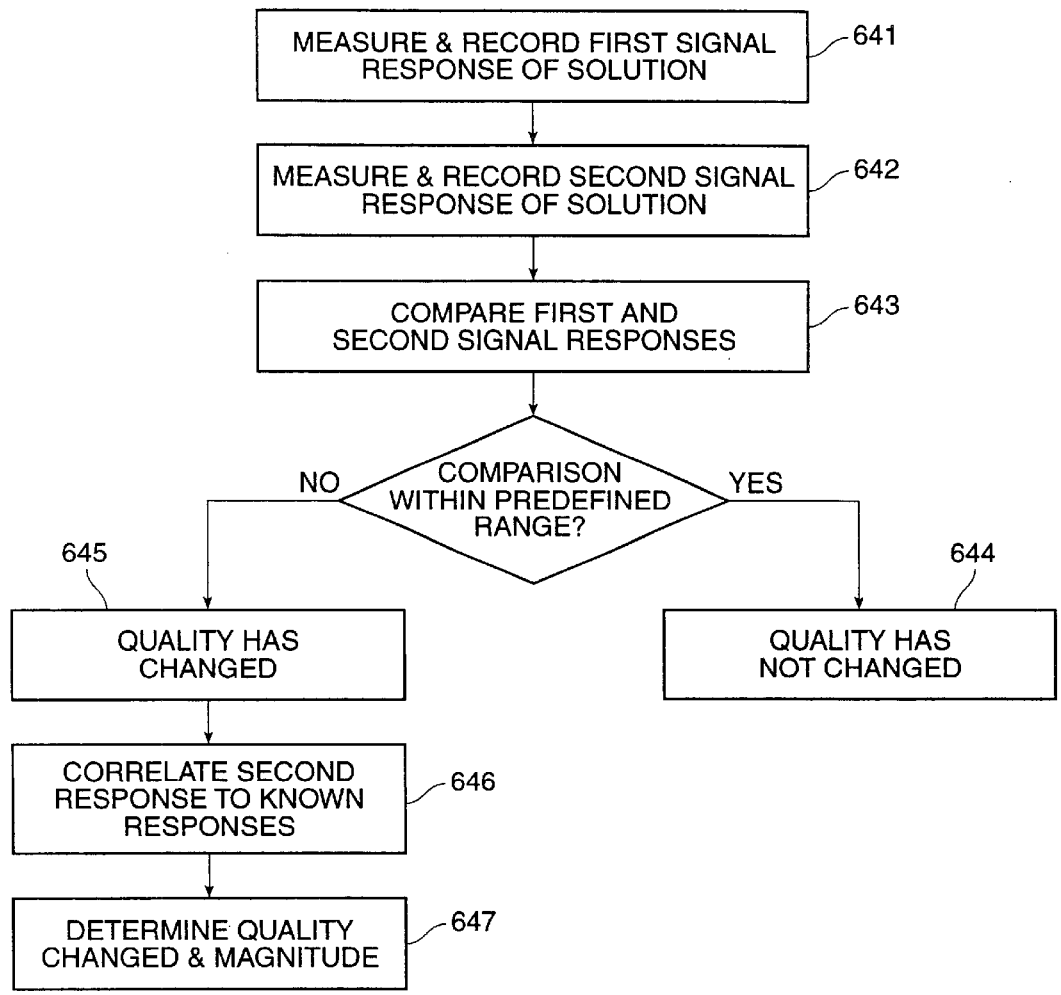
FIG. 4C illustrates one embodiment of a method for measuring dielectric changes of the molecular binding region in accordance with the present invention.

FIG. 4C illustrates an exemplary embodiment of the process. The process closely parallels the disclosed method for identifying binding events, the exception being that the method allows for the detection and quantitation of changes in dielectric properties of the MBR.

The process begins at step 641, when a solution having an initial dielectric property is added to the bio-assay device, the signal response is measured and recorded. In one embodiment, this step is performed according to steps 602–612. After a predetermined time or operation, a second measurement is made and a second signal response is recorded (step 642), again in one embodiment according to steps 602–612. At step 643, a comparison is then made between the first and second signals to determine whether the two signals correlate within a predefined range. If so, the properties of the solution are deemed to not have undergone any dielectric changes (step 644).

If the signal responses do not correlate within a predefined range, one or more dielectric properties of the solution is deemed as having undergone (step 645). Optionally the change in dielectric properties may be quantitated in the following manner. At step 646, the second signal is stored and correlated to a known signal response. The closest correlated response will identify the dielectric property of the solution and the first signal response can be correlated to the initial value of the dielectric property, the difference of which can be used to determine the amount by which the identified dielectric property has been altered (step 647).

D. Identifying Bound Molecular Structures

Figure 4D:
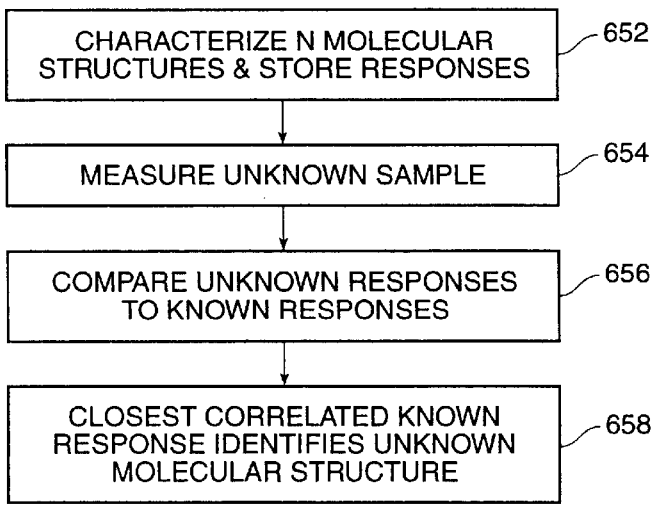
FIG. 4D illustrates one embodiment of a method for identifying a ligand in an unknown solution in accordance with the present invention.

Using the described bio-assay devices, it is possible to characterize a known ligand and subsequently identify it in a solution having an unknown ligand make-up. FIG. 4D illustrates one embodiment of this process. Initially at step 652, a large number of molecular structures are measured and their responses stored using one or more of the measurement systems, described below. In one embodiment, this step is performed according to steps 602–612. Each stored response may correspond to a single ligand occurring within the solution or multiple ligands occurring within the same solution. Subsequently at step 654, a measurement is made of an unknown solution. In one embodiment, this step is performed according to steps 602–612. Next at step 656, the signal response of the solution is compared to the stored signal responses to determine the degree of correlation therewith. At step 658, the unknown molecular structure is identified by selecting the stored response which exhibits the closest correlation to the unknown response. The comparison may be performed using one or more data points to determine the correlation between one or more stored responses, and may involve the use of pattern recognition software or similar means to determine the correlation. The process may be used to identify primary, secondary or higher-order bound molecular structures.

E. Identifying Classes of Bound Molecular Structures

It is also possible to characterize known molecular substructures such as sequence homologies in nucleic acids. In one embodiment, the process proceeds as shown in FIG. 4D, except that in step 652, N number of molecular substructures are measured and their responses stored. Each stored signal response may correspond to one or more sub-structures. The process continues as described in steps 654, 656 and 658 until a sufficient number or structures have been detected and characterized to identify the unknown compound. Once a sufficient number of correlations occur, it is then possible to classify the unknown molecular structure.

Figure 4E:
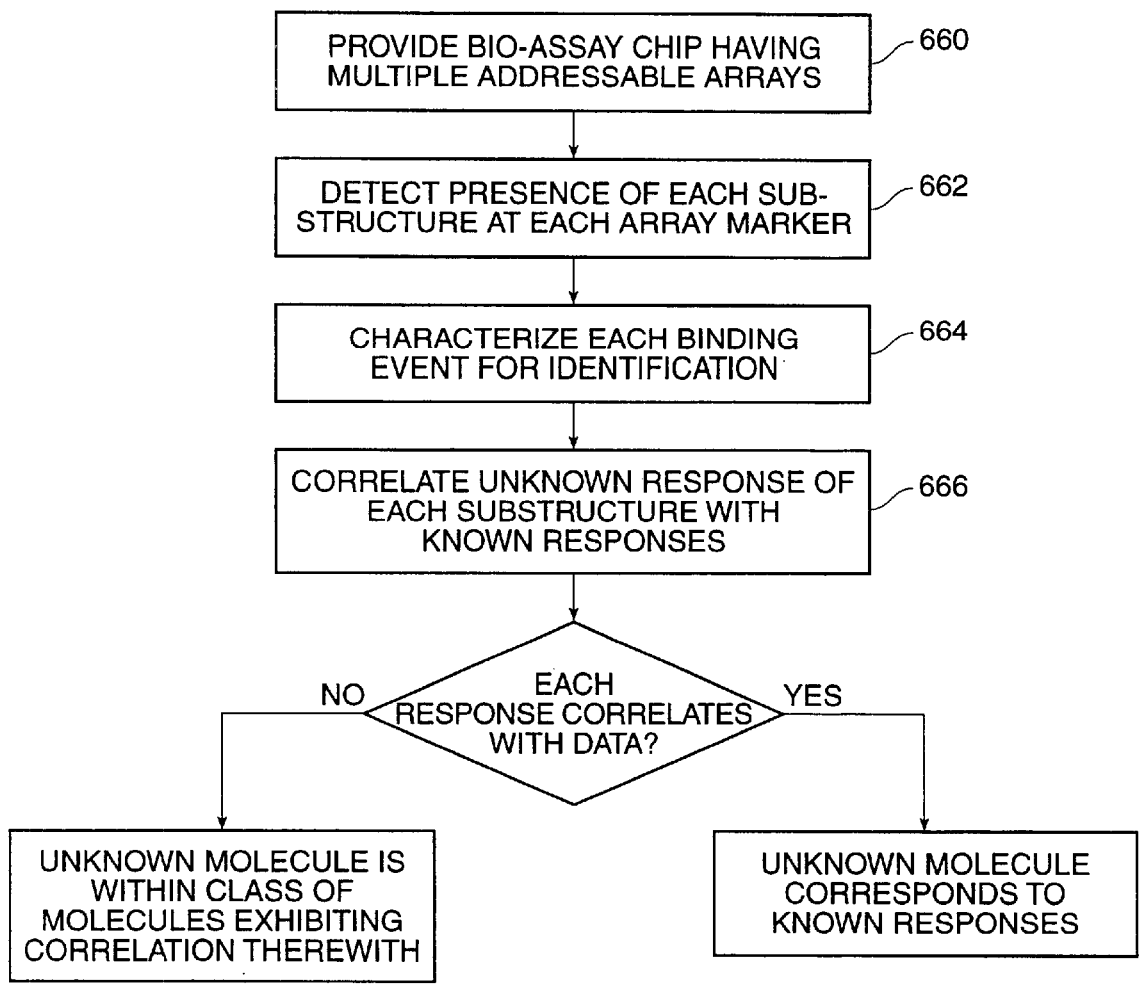
FIG. 4E illustrates one embodiment of a method for identifying the class of a ligand in accordance with the present invention.

FIG. 4E illustrates another process by which unknown ligands may be classified. The process identifies the unknown ligand by detecting binding to structural motifs on the unknown compound. Initially, at step 660 a bio-assay device is provided which has multiple addressable arrays, each of which has a antiligand for a specific ligand substructure. Next at step 662, the presence of particular substructures is detected by the binding of each to its respective antiligand, and subsequent characterization. In one embodiment, this step is performed according to steps 602–612. Subsequently at step 664, each of the binding events is then characterized by identification of qualities such as affinity, kinetics, and spectral response. At step 666, a correlation is then made between the known and unknown responses. If each of the unknown responses correlates to known responses, the ligand is identified as the ligand corresponding to the known response. If the sub-structures exhibit both correlated and uncorrelated responses, the correlated responses may be used to construct a more general classification of the unknown ligand. This process may be used to identify any molecular structure, for example proteins, which occur within the same class or have re-occurring structural homologies.

It is also possible that an intensive spectral analysis of a given unknown compound could lead to insights on structure and function, as comparisons can be made to known structures, and extrapolation will lead to some level of classification.

F. Specific v.s. Non-Specific Binding

Specific ligand binding is distinguished form non-specific binding by the spectral "fingerprint" or "signature" of the binding event. A given binding event of interest (for example nucleic acid probe and target nucleic acid) may be first characterized in a purified solution containing just the ligand of interest and the antiligand specific to said ligand on the MBR. A broad spectral study is then carried out to see where in the spectrum the strongest responses are found. The assay is then repeated in the solutions typically found in the dedicated applications, for example whole blood, to determine what effects non-specific binding has on the response. Then various points are found which are determinate of specific binding, and a separate set of points are found which are determinate of non-specific binding, an a subset of these frequency points are chosen for the actual assay application. By comparing the response due to specific binding with those due to the non-specific binding, the extent of specific binding can be determined.

G. Characterization of a Given Ligand

Often it is desirable to determine certain qualities of a given molecule. Examples include determining the class to which a protein belongs, or which type of polymorphism a given gene or other nucleic acid sequence is. This may be done in a number of ways.

For example, a given gene may be known to have a certain base pair sequence. Often times in nature there will be small variations in this sequence. For example, in the gene which codes for a chloride ion transport channel in many cell membranes there are common single base-pair mutations, or changes. Such changes lead to a disease called cystic fibrosis in humans. Thus characterizing a given nucleic acid sequence with respect to small variations is of enormous importance. Such variations are often called polymorphisms, and such polymorphisms are currently detected by forming complementary strands for each of the known polymorphisms. Since any given gene may take the form of any one of hundreds or even thousands of polymorphisms, it is often an arduous task to generate complementary strands for each polymorphism. Using the invention described herein, non-complementary binding or hybridization may be detected and distinguished by measuring many of the same physical properties as were described in the previous paragraph: The dielectric properties of the hybridization event can be characterized and correlated to known data, thereby determining the type of hybridization which has occurred—either complete or incomplete. Thus with an antiligand comprised of a given nucleic acid sequence, hundreds of different polymorphisms (as ligands) may be detected by the characterization of the binding event. One of skill in the art will appreciate that further refinements are possible, such as modifying the stringency conditions to alter the hybridization process, or varying the temperature and determining the melting point, which serves as another indicator of the nature of the hybridization process.

H. Quantitating Concentrations

Figure 4F:
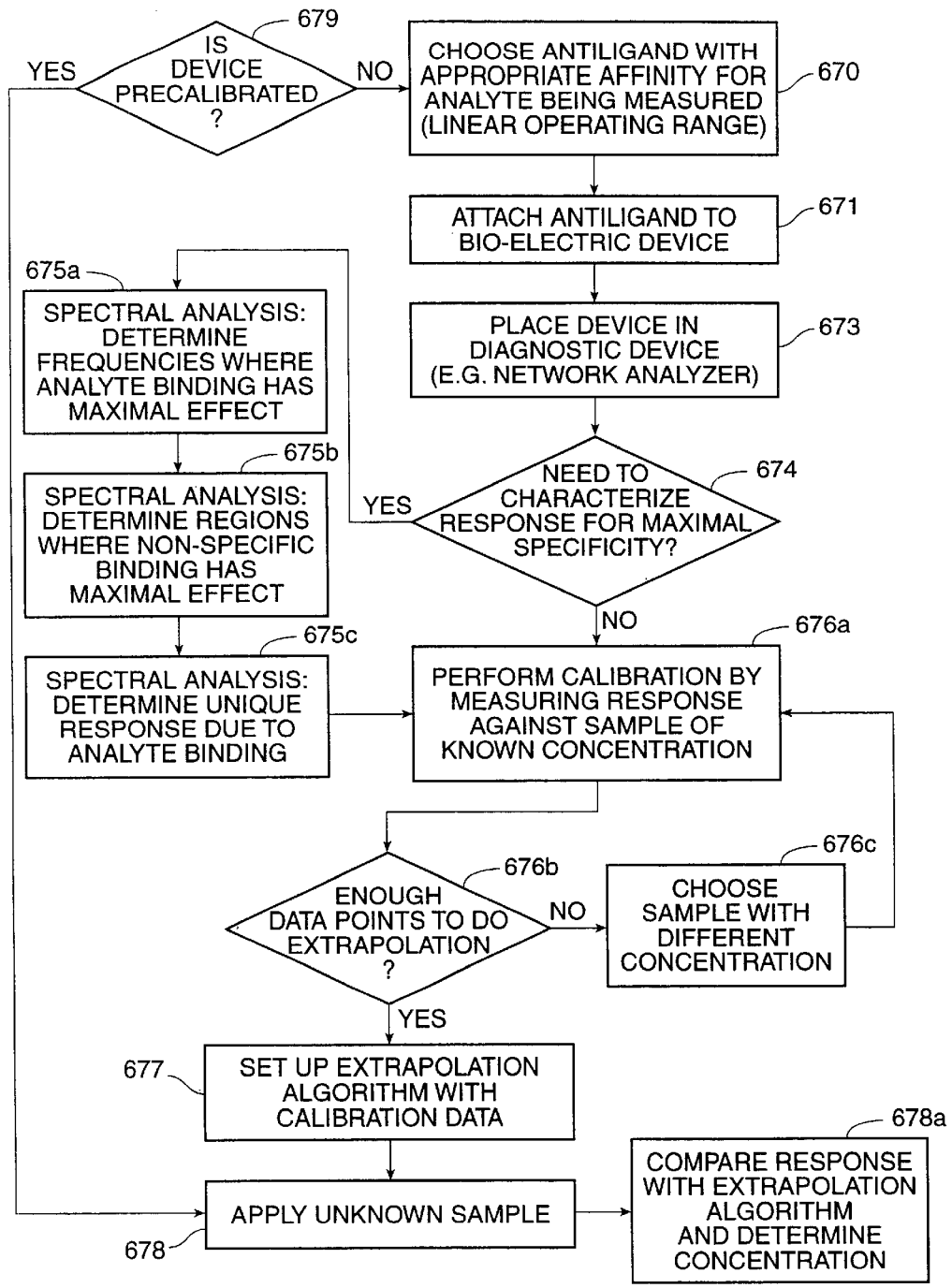
FIG. 4F illustrates one embodiment of a method for quantitating the ligand concentration of a solution in accordance with the present invention.

The bio-assay devices described herein may also be used to quantitate the concentrations of ligands. FIG. 4F illustrates one embodiment of this process. In the event the device is not precalibrated (step 679), initially at step 670, antiligands are chosen having the appropriate binding properties, such as binding affinity or kinetics, for the measured analyte. These properties are selected such that the antiligand's equilibrium constant is near the center of its linear operating region. For applications where the range of concentration is too wide for the use of a single antiligand, several antiligands may be used with differing affinities and/or linear operating ranges, thereby yielding a value for the concentration over a much wider range.

Next at step 672, the antiligands are attached to the bio-assay device or chip, and at step 673 the device is connected to the measurement system. At step 674, a decision is made as to whether the response requires characterization for maximum specificity. If so, a spectral analysis is performed in which the frequencies where analyte binding has maximal binding is determined (step 675a), the regions where the non-specific binding has maximal effect is determined (step 675b), and the unique response due to analyte binding is determined (step 675c). If characterization is not required, or if so, after its completion, the device is calibrated. This step is performed in one embodiment by supplying a known concentration of ligands to the bio-assay device and measuring the resulting response (step 676a). Alternatively, if more data points are needed for the calibration (step 676b), then a sample may be chosen with a different concentration (step 676c), and the response against this concentration may be measured (step 676a). In one embodiment, the measurement is made in accordance with steps 602–612. Subsequently at step 677, an extrapolation algorithm is generated by recording the calibration points from the foregoing response. Next at step 678, a sample of unknown ligand concentration is measured. This step is accomplished in one embodiment by supplying the unknown sample to the bio-assay device, correlating the response to the titration algorithm, and determining therefrom the ligand concentration.

In the event that a given bio-assay device is either pre-calibrated, or calibrated by design, the only step required is to apply the ligand or analyte to the surface, and measure the response. Such a bio-assay device may be realized in many different ways. For example, some circuit parameter like impedance or characteristic frequency of a resonant circuit may be designed to change in a pre-determined way when the binding event occurs, and the amount by which the parameter changes may further be designed to have a dose-response. Thus, a measurement of said circuit parameter will, when analyzed via a suitable algorithm, immediately yield a quantitative value for the concentration of a given analyte or ligand.

I. Bio-assay Device Self-Calibration

The described bio-assay devices possess a self-diagnostic capability and thus a point-of-use quality control and assurance. For a given dedication application, a particular antiligand (primary binding species) will act as an antiligand for some ligand (the secondarily binding species) of interest in the solution. The primary binding species may be attached at the point of fabrication, and the secondary binding species may be attached at the point-of-use. Thus, variations in fabrication—especially the attachment of the primary species—will cause variations in the ability of the device to bind its specific ligand. However, the amount of ligand bound will be in direct proportion to the amount of antiligand bound, thus a ratiometic measurement of the two is possible.

Figure 4G:
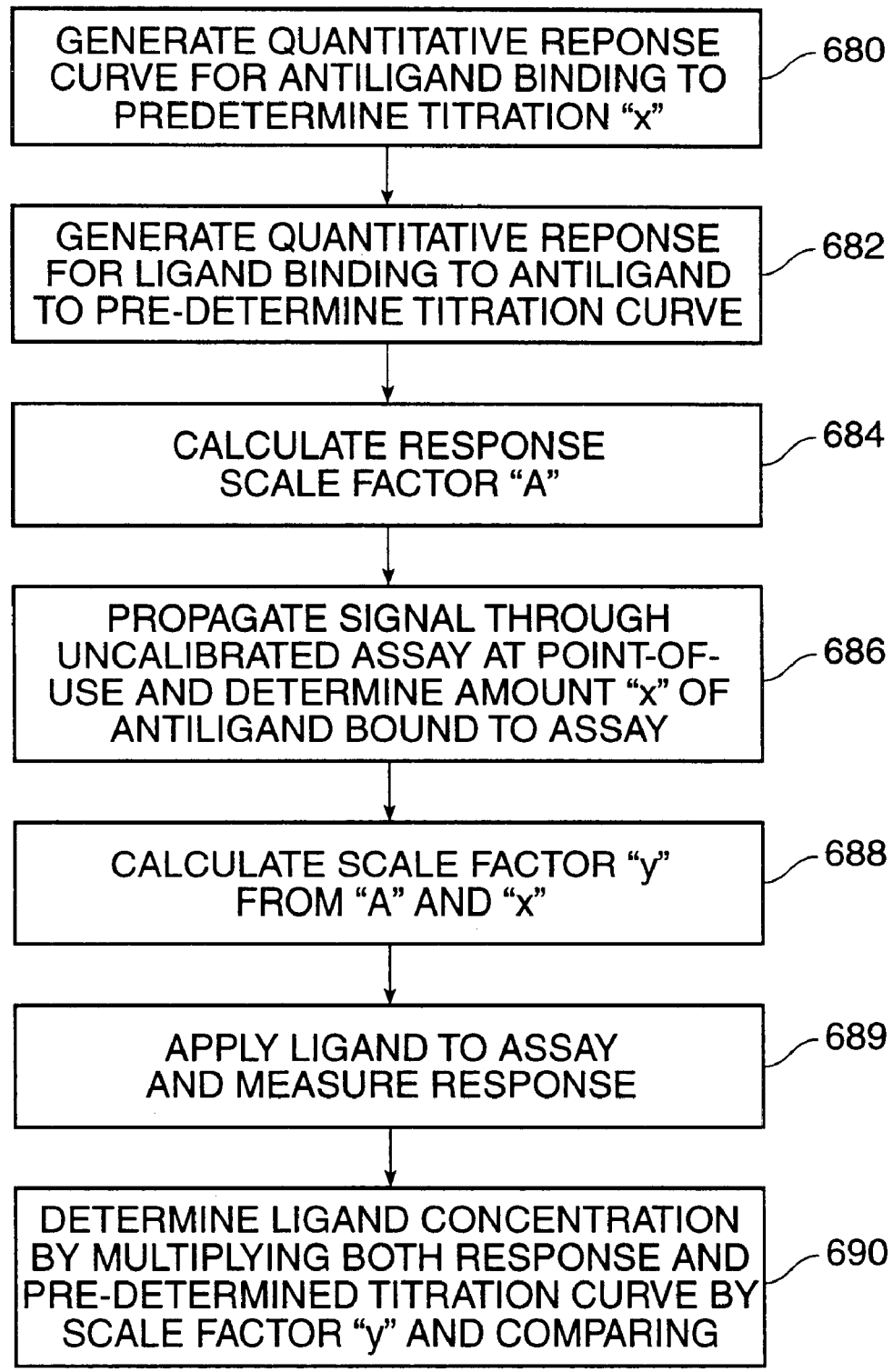
FIG. 4G illustrates one embodiment of a method for providing a self-diagnostic capability of the bio-assay device in accordance with the present invention.

FIG. 4G illustrates one embodiment of the process. Initially at step 680, a molecular binding surface is formed along the signal path by binding the appropriate antibody at various concentrations and characterizing the resulting response for each of these concentration, yielding some value "x" for each concentration. Next, at step 682, a similar titration curve is generated for the ligand by measuring the antibody/ligand binding response for several different concentrations of ligand, and a ligand titration curve is predetermined. Next, at step 684 a scale factor A is generated by taking the ratio of responses of antibody binding to ligand binding. At the point-of-use, the uncalibrated assay is then first probed (step 686) to determine the amount of bound antibody "x." The scale factor "y" is subsequently computed as A*x. The ligand is then applied to the assay and the response is measured (step 689), and the response and predetermined titration curve are scaled by the scale factor "y" (step 690) to determine unknown concentration.

The process of FIG. 4F may also be modified to allow quantitating the amount of ligand in the solution. In the modification, the binding surface of the bio-assay device includes antiligands having a predefined affinity and ligand specificity. The solution is subsequently applied to the device, and a response is measured. The signal response will be proportional to the amount of the ligand that has bound. Thus, a titration of any given ligand may be carried out by choosing an antiligand with an appropriate linear operating range—the range in which the equilibrium constant is within a couple of log units of the desired range of concentrations to be detected. The same ratiometric analysis as described above can be applied to yield a robust and precise quantitative assay with internal controls and calibration necessary to insure reliability.

VI. Measurement Systems

Various measurement systems may be used to perform the above-described methods. FIGS. 5–8 illustrate three examples of possible measurement systems: a frequency domain test system, a time domain test system and a dielectric relaxation measurement system.

A. Frequency Measurement System

Figure 5A:
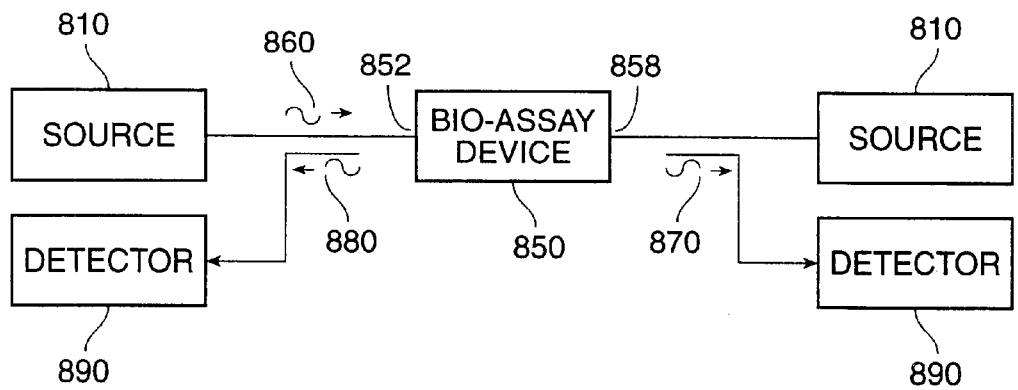
FIG. 5A illustrates one embodiment of a frequency measurement system in accordance with the present invention.

FIG. 5A illustrates one embodiment of a frequency measurement system in accordance with the present invention. The system 800 includes a signal source 810 coupled to the bio-assay device input 852 and a signal detector 890 coupled to the bio-assay device output 858. Optionally, an additional signal source may be coupled to the bio-assay device output 858 and an additional signal detector coupled to the test circuit input 852 for providing complete two-port measurement capability. The system may be modified to a one-port test system in which a signal detector is coupled to the signal path for receiving a reflected signal. In a specific embodiment, the aforementioned frequency measurement system consists of a network analyzer such as model number 8510C from the Hewlett-Packard Company. Other high frequency measurement systems, such as scalar network analyzers, which provide signal information based upon transmitted and reflected signals may alternatively be used.

Figure 5B:
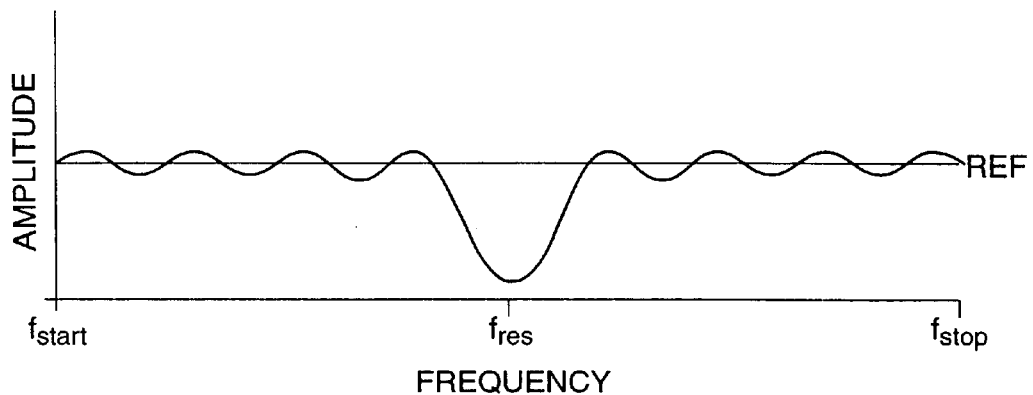
FIG. 5B illustrates a first frequency response measured which can be used to detect or identify a molecular structure in accordance with the present invention.
Figure 5C:
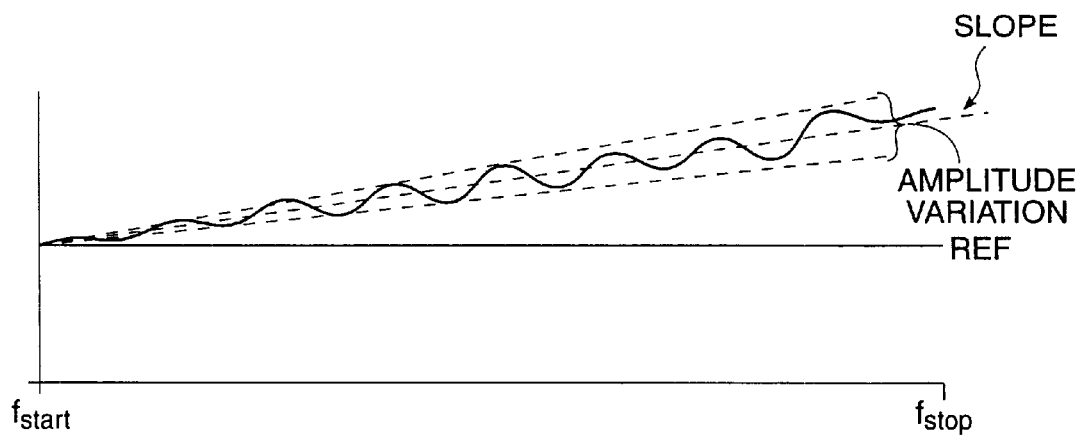
FIG. 5C illustrates a second frequency response which can be used to detect or identify a molecular structure in accordance with the present invention.

Measurements are made according to the aforementioned methodologies. Initially, an incident signal 860 is launched toward the test circuit and the transmitted and/or reflected signals 870 and 890, respectively, are subsequently recovered. The resulting signal responses will take the form of unique frequency responses, also called "spectral fingerprints" or "signatures," two examples of which are shown in FIGS. 5B and 5C. FIG. 5B illustrates one type of frequency response in which a resonance occurs at frequency $f_{res}$. Here, response 870 undergoes a steep fall and rise, indicating that little or no signal energy reaches the output port at this frequency. The resonance is caused by the dielectric property and impedance of the MBR changing over frequency $f_{start}$ to $f_{stop}$. Different ligands will resonate at different frequency points. In addition, some ligands may exhibit multiple resonant frequency points over the measured band $f_{start}$ to $f_{stop}$. Once a ligand has been characterized as having one or more uniquely occurring resonance points, this data can be used to identify the presence of the ligand in an unknown solution. This characterization can be ascertained from empirical data or from theoretical calculations of multipole moments and resonant frequencies. Furthermore, when detecting the presence of secondary binding events, this data can indicate when an analyte is bound to a ligand by a change in the one or more unique resonance points.

FIG. 5C illustrates another type of frequency response which can be used to detect or identify a molecular structure. In this case, the frequency response exhibits a generally monotonically increasing or decreasing trend with some degree of amplitude variation. The response's slope and/or the amplitude variation may be used to detect and/or uniquely characterize the bound molecule. Thus in the described manner, the resonant frequency points, slope, trend, and variation of the test signal's phase may be used to uniquely identify the molecular binding event. The frequency response may be measured at the input port 852, at the output port 858 or at both ports to uniquely identify the bound molecular structure.

Figure 6:
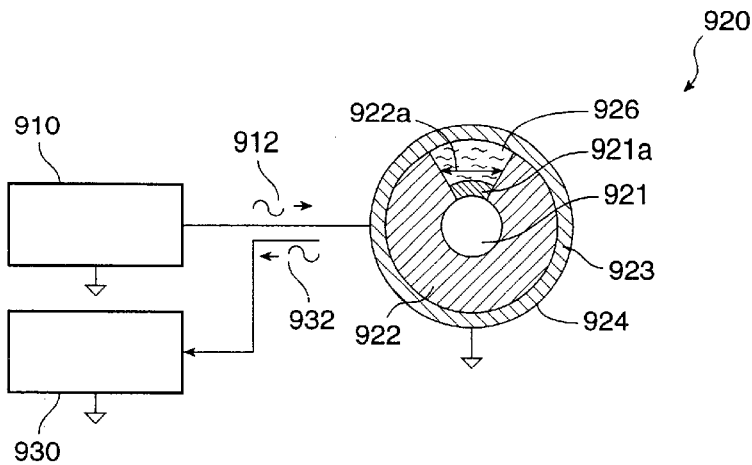
FIG. 6 illustrates a second embodiment of a frequency measurement system in accordance with the present invention.

FIG. 6 illustrates a second exemplary embodiment of a frequency measurement system in accordance with the present invention. The bio-assay device under test 920 consists of coaxial topology having a center conductor 921, a first insulator 922 having a cavity 922a, a second insulator 923, and an outer conductor 924. Solution 926 occupies cavity 922a. Of course, devices of other circuit topologies may be tested as well.

Once the solution 926 is added to the cavity 922a, the molecules within the solution 926 form a MBR 921a proximate to the center conductor 921. During the measurement, a signal source 910 launches an incident test signal 912 to center conductor 921. The MBR 922a modulates the incident test signal 912, and the reflected test signal 932 provides a unique signal response which can be used to identify the ligand. The one-port coaxial configuration may be realized, for instance, as a sub-cutaneous needle structure.

B. Time Domain Measurement System

Figure 7:
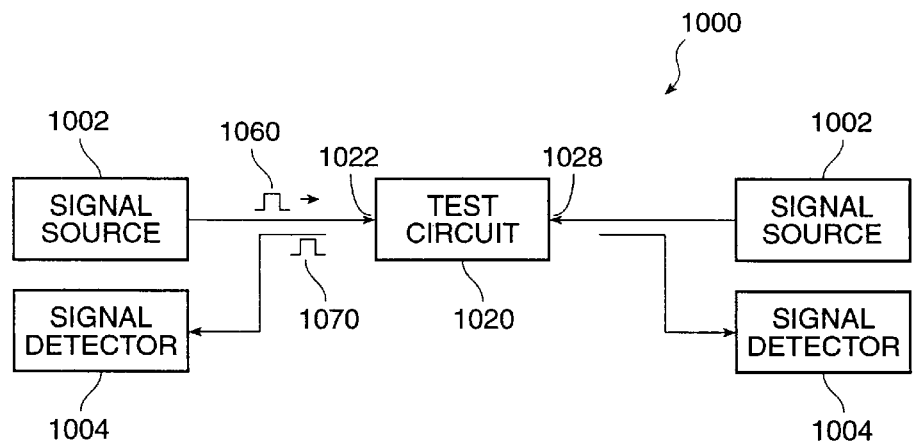
FIG. 7 illustrates one embodiment of a time domain measurement system in accordance with the present invention.

FIG. 7 illustrates one embodiment of a time domain measurement system 1000 in accordance with the present invention. The system includes a pulse source 1002 and a detector 1004 coupled to the input 1022 of the test circuit 1020 (consisting of any of the bio-assay devices described herein). In an alternative embodiment, an additional pulse source and detector may be coupled to the output port 1028 to provide complete two-port measurement capability. Further alternatively, the system may comprise a one-port test system in which a signal detector is coupled to the signal path for receiving a reflected signal. In a specific embodiment, the time domain measurement system consists of a time domain reflectometer such as model number 11801 manufactured by the Tektronix Corporation. Other high frequency measurement systems, such as network analyzers having a time domain measurement mode which provide signal information based upon transmitted and reflected signal pulses may alternatively be used.

In the time domain measurement system, the input test signal 1060 consists of a time domain pulse, the reflected portions of which can be displayed over time. In the present embodiment, an incident pulse 1060 is launched toward the portion of the transmission line which is tightly coupled to the assay surface. Due to the dielectric property of the MBR, a portion of the incident pulse 1060 is reflected toward the detector 1004. The reflected pulse 1070 will exhibit a unique shape and/or time delay which is characteristic of the MBR's dielectric properties, which are in turn largely defined by the dielectric properties of the ligand, antiligand, and the surrounding solution. Thus, the pulse shape and delay of the reflected pulse 1070 can be used to characterize and identify the ligand. The time domain test system may be used separately or in conjunction with the high frequency test system to identify one or more unknown ligands.

C. Dielectric Relaxation Measurement System

As known in the art, the dielectric relaxation frequency of a ligand is the rate at which the dielectric properties of the molecular level changes when an electric field is applied to the molecule. As with the dielectric properties of the ligand, the dielectric relaxation frequency is primarily defined by the structure and binding geometries unique to each molecule. Thus once measured, the dielectric relaxation frequency of a ligand can be used to identify it.

Figure 8:
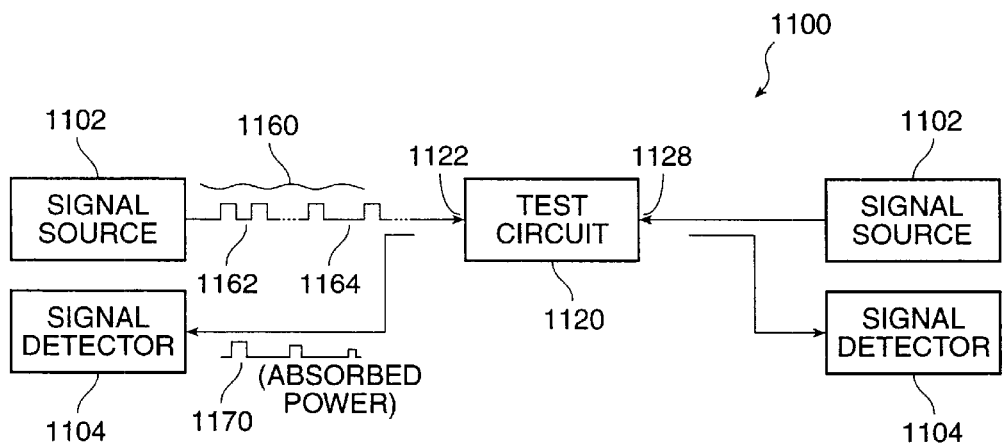
FIG. 8 illustrates one embodiment of a dielectric relaxation measurement system.

The dielectric relaxation frequency can be quantified by measuring the rate at which the ligand absorbs power over frequency. FIG. 8 illustrates one embodiment of a system 1100 for making this measurement. The measurement system 1100 is similar to the time domain measurement system 1000 illustrated in FIG. 7 and includes a pulse source 1102 and a detector 1104 coupled to the input 1122 of the test circuit 1120 (consisting of any of the bio-assay devices described herein). An additional pulse source and detector may be coupled to the output port 1128 to provide complete two-port measurement capability. In a specific embodiment, the time domain measurement system consists of a time domain reflectometer such model number 11801 manufactured by the Tektronix Corporation. Other high frequency measurement systems, such as network analyzers having a time domain measurement mode which provide signal information based upon transmitted and reflected signal pulses may alternatively be used.

The input test signal 1160 consists of separate pulse groups, each group having two or more incident pulses and a different pulse interval. The pulse groups 1162 and 1164 are launched toward the portion of the transmission line which is tightly coupled to the binding surface. If a pulse group 1162 has an interval substantially equivalent to the dielectric relaxation period (the reciprocal of the relaxation frequency), the MBR will absorb successively less energy in succeeding pulses. The decrease in signal absorption can be measured in the reflected response 1170 at the input port 1122 or at the output port 1128. As an alternative measurement quantity, the remaining signal power may be measured either at the input port 1122 or the output port 1128.

The rate of change of signal absorption and the pulse interval at which the change occurs can then be plotted and used to characterize and identify the unknown bound molecule(s). This system characterization may be used independently or in conjunction with the above-described time and/or frequency domain test systems.

In all of the above systems, one of skill in the art will readily appreciate that such systems can be scaled down to the chip level using such technologies as Microwave Monolithic Integrated Circuits (MMIC) and the like. Such miniaturized systems can be readily extended to highly parallel systems capable of detecting and measuring hundreds, thousands, or tens of thousands of compounds simultaneously. These systems can be configured to yield "logic gates" which are switched by the binding event itself, such as by changing a characteristic impedance and thus the transmission and/or reflection coefficients, or by changing the band pass properties of such a circuit, and using this as the on/off gate.

VII. Integration of Detection System With Chip Technology
A. General

The bio-assay device described above can be included on an inexpensive and disposable chip. Because of the ease of miniaturization, very small chips with thousands or tens of thousands of addressable bio-assay devices contained therein can be prepared. As described in additional detail below, chips containing arrays of nucleic acids can be used in expression monitoring, sequence checking, detection and identification of SNPs, and de novo sequencing applications, as well as a variety of other diagnostic, detection and identification purposes. For a review on the use of microarrays in nucleic acid analyses see, for example, the review articles by various authors in Nature Genetics Supplement, 21:1–60 (1999), each of which is incorporated herein by reference in its entirety.

The chips can be manufactured from a variety of inexpensive materials, such as plastic or glass substrates, for example. The chips can have a variety of shapes and sizes and the binding layer can vary in structure as described above in relation to FIGS. 1D–1F.

In current methodologies using chips to analyze nucleic acids, the target nucleic acids contained in a sample generally need to be labeled, most commonly with a fluorescent label. The present invention eliminates the need to label target nucleic acids and the problems associated with such labeling, since binding events can be detected directly through modulation of the transmitted signal.

B. General Design

The chip used in the methods of the present invention typically includes multiple element arrays, wherein each element or site includes a nucleic acid probe or, more typically, a plurality of probes. Each element of the array includes a signal path such as a transmission line and appropriate circuitry for addressing the element. Each element is contacted with a solution potentially containing target nucleic acids under hybridizing conditions. After providing a sufficient period for hybridization to occur, the elements are washed to remove molecules not bound to the probe. However, as described in greater detail below, given the sensitivity of the detection system of the present invention and its ability to distinguish between different binding events, a wash cycle is not necessary in some methods.

Arrays can vary widely in the number of elements or sites, as well as with regard to the number of probes within any given element. As for the number of elements, the number of desired elements may vary according to the type of application. Thus, for example, the number of elements in sequence checking or diagnostic applications can be relatively few since typically the number of different nucleic acids being tested for is relatively limited. Hence, the array may consist of a single element if only one sequence is being assayed. There may be additional elements if multiple sequences are being checked, or if additional redundant elements (i.e., elements in which the probes located therein have the same sequence as another element) are used as controls. In expression analysis studies, the number of different elements is typically considerably higher than in sequencing checking applications since the presence of many more nucleic acids are being probed. The number of elements in sequencing applications is generally even higher yet since, in some embodiments, it may be desired to utilize full length cDNAs to probe for many different genes, the cDNA for each gene being positioned within a separate element. In such embodiments, the number of elements can be up to 100,000 elements. Hence, in general, the number of elements can range from 1 up to 100,000. More specifically, some embodiments may include $10^1$, $10^2$, $10^3$, $10^4$, or $10^5$ elements, or any number therebetween.

The number or density of nucleic acid probes within an array also varies depending upon application and signal sensitivity considerations. In some methods, only a single probe is attached at an element, for example when the target sequence is present in considerable excess over other sequences or in samples containing relatively few target sequences. Single probes may can also be used, for example, when characteristic peaks for the hybridization complex of interest are well defined and do not overlap with other adjacent signals in a spectral scan. It is possible to use single probes in a variety of other situations as well. For applications involving more complex samples and lower sensitivity, the number of probes per element may be up to $10^{18}$ probes/cm². Hence, probe density typically varies from 1 probe per element to $10^1$, $10^2$, $10^3$, $10^4$, $10^5$, $10^6$, $10^7$, $10^8$, $10^9$, $10^{11}$, $10^{12}$, $10^{13}$, $10^{14}$, $10^{15}$, $10^{16}$, $10^{17}$ or $10^{18}$ probes/cm², or any density therebetween.

Probe length is another variable in array structure. Arrays using synthetic oligonucleotide probes may be quite short, such as 5, 10, 20, 30, 40, 50, 100 or a few hundred base pairs long, or any number of base pairs therebetween; cDNA probes can also be relatively short if prepared from segments of genes. Probes can, however, be up to $10^5$ base pairs long, especially with full length cDNA clones. Hence, probes are typically 5, 10, $10^2$, $10^3$, $10^4$, $10^5$ or $10^6$ base pairs long, including all size ranges therebetween.

C. Addressing Array Elements

In general terms, it is possible to interrogate each element of an array by propagating a signal down each of the signal paths which run to the various elements and detecting a signal resulting from the formation of a hybridization complex at an element wherein a hybridization complex has formed. In some instances, signal detection involves propagating a signal along a signal path when only a nucleic acid probe is coupled to the signal path and measuring a baseline signal. In other instances, the baseline signal is obtained when only a buffered solution is in contact with the signal path. After the probe is contacted with sample and the array optionally rinsed, another signal is propagated down the transmission line and a measured signal compared with the baseline signal to obtain a difference between the signals. It is also possible to simultaneously transmit signals down multiple signal paths—one path extending to a test element and another path running to a control element which lacks either probe and/or target. Signals propagated down the various signal paths can be launched simultaneously or serially, i.e., launched at different times.

The exact nature of the addressing depends on the applications, but an example of the general strategy is as follows. A vector space is defined by the variables $K_{eq}$, $k_A$, and $\omega=(\omega 1, \omega 2, \omega 3, \ldots)$ where these variables represent the equilibrium constant, the kinetic constant, and a basis set of N frequencies at which the dielectric properties are probed. An N+2 dimensional space is thus defined into which every binding event can be mapped. A group of reference molecules (e.g., nucleic acids) is subsequently chosen which represents a spectrum of binding events of interest, such as a group of nucleic acids with different sequences; these reference molecules are then attached to addressable points on the chip. A particular species of molecules or group of species (e.g., target nucleic acid sequences) is introduced to the chip, and each address is then probed for the value of each of the points in the vector space defined above (or a suitable subset thereof). Each species can then be represented by an address in the vector space. The complexity of the system will depend on the size of the vector space and the total number of different immobilized ligands on the surface.

As an example of the above, consider a simple system comprised of two different nucleic acid probes which are analyzed at four different frequencies; and further, each of these frequencies can be parsed into ten different amplitudes. Such a system would have 100 million possible addresses ($10^4$ for a first polymorphism, for example, and $10^4$ for the second polymorphism, for example). An unknown placed in the system can be represented by a unique address of the form [(1,5,3,7)(4,8,6,7)], where the first four numbers represent the spectral response of the first probe at the four selected frequencies, and the latter four numbers represent the spectral response of the second probe at the four selected frequencies. Thus with just two probes and four frequencies, 100 million unique addresses can be generated.

D. Detection

Signals generated as a result of hybridization at the various sites can be tracked using a computer which stores the signals for the various elements. In this way, it is possible to identify which elements include a hybridization complex. Often signal measurement involves scanning a range of frequencies or wavelengths. As indicated above, the signal generally ranges from the MHz to hundreds of Gigahertz level. In some embodiments, the signal is a microwave. In certain instances, for example, a signal may be scanned from 1 to 21 GHz.

The detector for the modulated signal can include a version of a "logic gate" in which the presence of a particular ligand or analyte has the effect of either turning on the gate or turning off the gate, as is appropriate for a given application. Such a gate may be realized in any number of ways which translate the binding event into an electromagnetic signal which can be assigned to one of two possible states corresponding to off and on, 1 or 0, and the like. The two states could be different frequencies of a resonant cavity or waveguide corresponding to bound and unbound, or amplitude changes in a transmission line or waveguide which correspond to bound and unbound, or changes in the band-pass of a particular circuit, or the like.

E. Specific Array Embodiments

Figure 11:
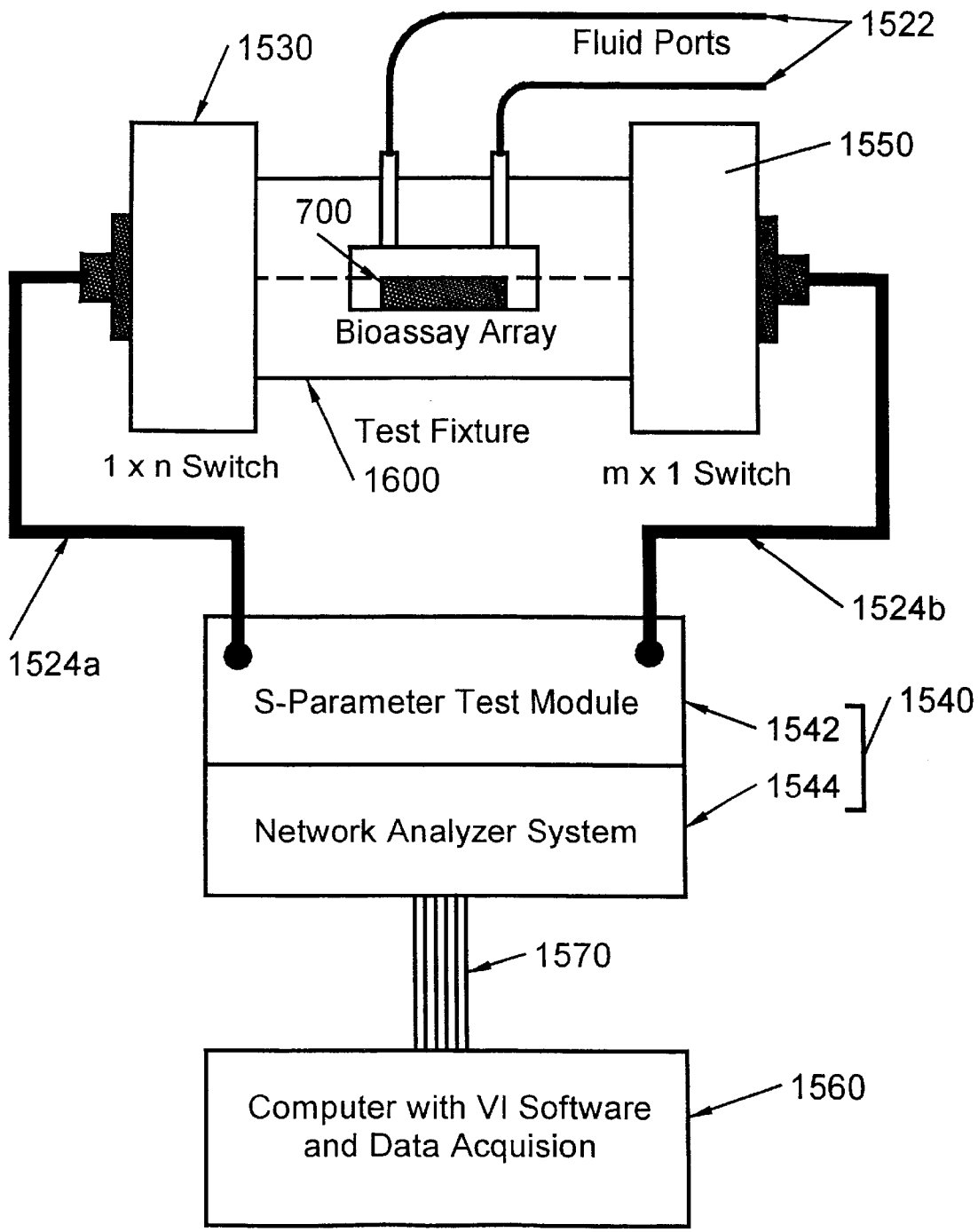
FIG. 11 illustrates one possible embodiment of an N×M array test system in accordance with the present invention.

FIG. 11 illustrates one possible embodiment of an N×M array test system 1500 in accordance with the present invention. The test system includes a test fixture 1600 further described below, a 1×N input switch 1530, a measurement system 1540, a M×1 output switch 1550, and a computer 1560. Measurement system 1540 communicates test signals to the test fixture 1600 via input test cable 1524a and 1×N input switch 1530. The test signal is subsequently received from the test fixture via M×1 output switch 1550 and output test cable 1524b. Computer 1560 controls 1×N input switch 1530, measurement system 1540, and M×1 output switch 1550 via a control bus 1550.

In one embodiment, measurement system 1540 includes an S-Parameter Test Module model no. 8516A, a Frequency Synthesizer (not shown) model no. 8341B, and a Vector Network Analyzer model no. 8510B, all of which are manufactured by the Hewlett Packard Company of Palo Alto, Calif. (www.hp.com). In this embodiment, measurement system 1540 provides a measurement capability between the frequencies of 45 MHz and 40 GHz. In an alternative embodiment, measurement system 1540 may consist of model number HP 8751A network analyzer which provides a measurement capability between 5 Hz and 500 MHz. In a further embodiment, measurement system may consist of model number HP 85106D which provides a measurement capability between 33 GHz and 110 GHz, both manufactured by the Hewlett Packard Company. Other measurement systems such as scalar network analyzers, Time Domain Reflectometers, an other similar measurement systems may also be used to detect a change in the test signal which is attributable to the dielectric properties of the MBR.

Test cables 1524 support the propagation of the test signals at the desired frequency. In one embodiment, test cables consists of model number 6Z PhaseFlex™ Microwave test cables manufactured by the W. L. Gore and Associates, Inc. of Newark Del. (www.gore.com). Control bus 1550 provides communication between the test system and computer 1560 and in the illustrated embodiment consists of a General Purpose Instrument Bus (GPIB). In alternative embodiments, measurement system 1540 and computer 1560 may be integrated within a single automated measurement unit.

Computer 1560 controls measurement system 1540 to generate test signals at one or more frequencies, output power levels, signal shapes, phase offsets or other measurement settings. In the preferred embodiment, computer 1560 includes a +450 MHz microprocessor, such as those manufactured by the Intel Corporation of Santa Clara, Calif. (www.intel.com). Test system control, data acquisition, and analysis may be performed using a graphical programming software tool, such as LabVIEW® manufactured by the National Instruments Corporation of Austin, Tex. (www.natinst.com).

Alternatively or in addition, measurement system 1540 may include a Time Domain Reflectometer (TDR) system, such as those optionally available with the above-described network analyzers or described in the incorporated patent application entitled: "Method and Apparatus for Detecting Molecular Binding Events," Ser. No. 09/243,194. Essentially, TDR systems transmit a signal pulse towards a unit under test. The return signal (either reflected from or transmitted through the unit under test) can be analyzed to ascertain information about the unit under test. Specifically in the present embodiment, the dielectric properties of the MBR will modulate the signal pulse, thereby enabling detection and identification of the molecular binding events therein.

TDR measurements may be made at the fixture level using the aforementioned systems, or at the bio-assay device level utilizing one or more of the standard techniques of microwave monolithic circuit (MMIC) technologies. When a TDR measurement is made at the device level, a time-domain test signal is generated in close proximity to the bio-assay device. This signal is then propagated along the signal path to the bio-assay element via standard conductive geometries used in MMIC technologies. The molecular binding region modulates the time-domain test signal, and the modulated signal is then recovered to be analyzed.

The 1×N input switch 1530 routes the test signal from the input test cable 1524a to one of the N test fixture signal inputs. The M×1 output switch 1550 routes the test signal from one of the M test fixture outputs to the output test cable. Input and output switches 1530 and 1550 may consist of any switching or multiplexing means which will support the propagation of the desired test signal. For instance, input and output switches 1530 and 1550 may consist of low frequency switches (DC to 2 GHz), such as those manufactured by Amplifonix, Inc. of Philadelphia, Pa. (www.amplifonix.com). Switches for use at higher frequencies (2–18 GHz), such as those manufactured by the General Microwave Corporation of Amityville, N.Y. (www.generalmicrowave.com) may alternatively be employed. Connection between bio-assay device and input and output switches 1530 and 1550 may be made using insulated cables, wire bonds, or other conventional interconnection means appropriate for the test frequency of operation.

In an alternative embodiment, input and output switches 1530 and 1550 and the bio-assay array form a monolithic integrated circuit. For instance, when the bio-assay array is fabricated using GaAs semiconductor processing techniques, input and output switches 1530 and 1550 may consist of integrally formed PIN diodes which are coupled to the bio-assay array. Further alternatively, input and output switches 1530 and 1550 may form an integrated assembly in which the input and output switches 1530 and 1550 are discrete components which are connected (via wire or ribbon bonds) to the bio-assay array. Both alternative embodiments provide advantages in that the interconnecting structures are miniaturized or eliminated, thereby reducing or eliminating the signal loss associated therewith.

As explained, the bio-assay array may be fabricated in wafer form using semiconductor processing techniques. In this embodiment, the array test system 1500 may consist of a wafer probe test station, such as those manufactured by Cascade Microtech, Inc. of Beaverton, Oreg. (www.cascademicrotech.com) which includes or is coupled to the aforementioned input and output switches 1530 and 1550, and computer 1560. The wafer probe station utilizes one or more probe cards, each of which is capable of providing a large number of low loss, low VSWR signal interconnections to the bio-assay array.

The probe card(s) may be used to provide N and/or M signal interconnections to the remotely located input and/or output switches 1530 and 1550, respectively. Alternatively, input and/or output switches 1530 and 1550 may be monolithically fabricated with the bio-assay array, in which case the probe card(s) provides a single input and/output signal transition to the measurement system 1540. In this latter embodiment, the probe card(s) includes probes for providing switch control voltages to the monolithically formed switches.

Alternatively or in addition, measurement system 1540 may include a Time Domain Reflectometer (TDR) system, such as those optionally available with the aforementioned network analyzers or described in the incorporated patent application entitled: "Method and Apparatus for Detecting Molecular Binding Events," Ser. No. 09/243,194.

2. Array Test Fixture

Figure 12A:
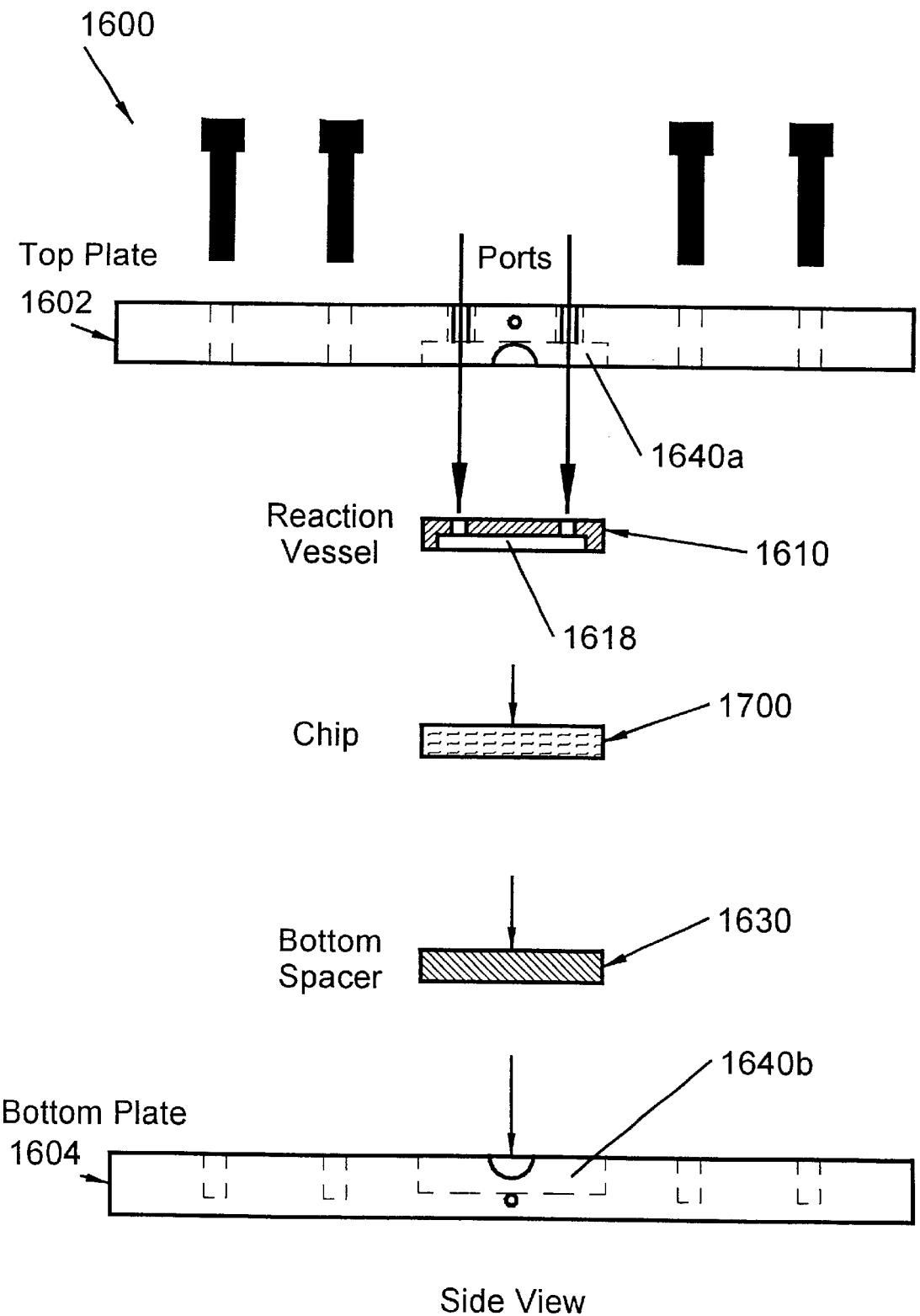
FIGS. 12A–12B illustrate various views of an N×M array test fixture in accordance with the present invention.

FIG. 12A illustrates a side view of one possible embodiment of the N×M array test fixture 1600 in accordance with the present invention. Test fixture 1600 includes a top plate 1602, bottom plate 1604, and a sample cavity 1640 (having top and bottom recesses 1640a and 1640b, respectively) which holds the aforementioned reaction vessel 1610, bio-assay device 1700 (further described in FIG. 13A below), and bottom spacer 1630 elements. In the illustrated embodiment, the supplied sample is contained on the top surface of the bio-assay device in recess 1618 of the reaction vessel 1610. In the N×M array test fixture embodiment, the dimensions of sample cavity 1640, correspondingly reaction vessel 1610, and bottom spacer 1630 are designed to accommodate the bio-assay device 1700 which may be larger or smaller than the bio-assay device. Each array element includes a small, monolithically deposited structure to form a recessed area over the signal path in order to hold a portion of the applied sample in electromagnetic communication with the signal path of each array element.

Figure 12B:
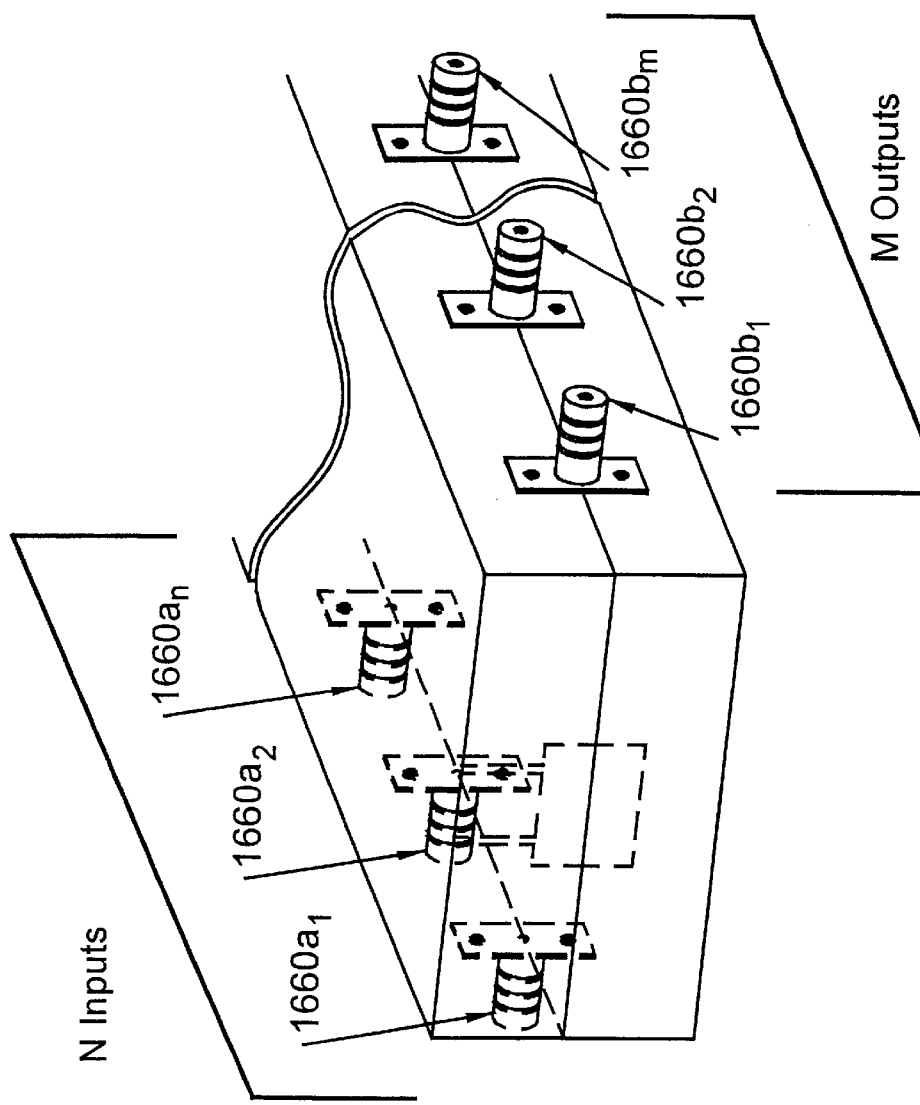

FIG. 12B illustrates an end view of the N×M array test fixture 1600. Test fixture 1600 includes N input connectors 1660a_1 to 1660a_n and M output connectors 1660b_1 to 1660b_m. Test fixture 1600 also includes N input transmission lines (not shown) which provide a signal transition between the fixture's N connectors 1660a_1 to 1660a_n and the bio-assay's N inputs. Test fixture 1600 further includes M output transmission lines (not shown) which transition between the bio-assay's M outputs and the fixture's M output connectors 1660b_1 to 1660b_m. The input and output transmission lines may be realized as insulated conductive wires, microstrip, stripline, coplanar waveguide transmission lines deposited on a dielectric substrate, or other conventionally known signal path architectures. The choice of the transmission line's architecture will be influenced by the test frequency band and the bio-assay device's input and output port density.

3. Bio-assay Array

Figure 13A:
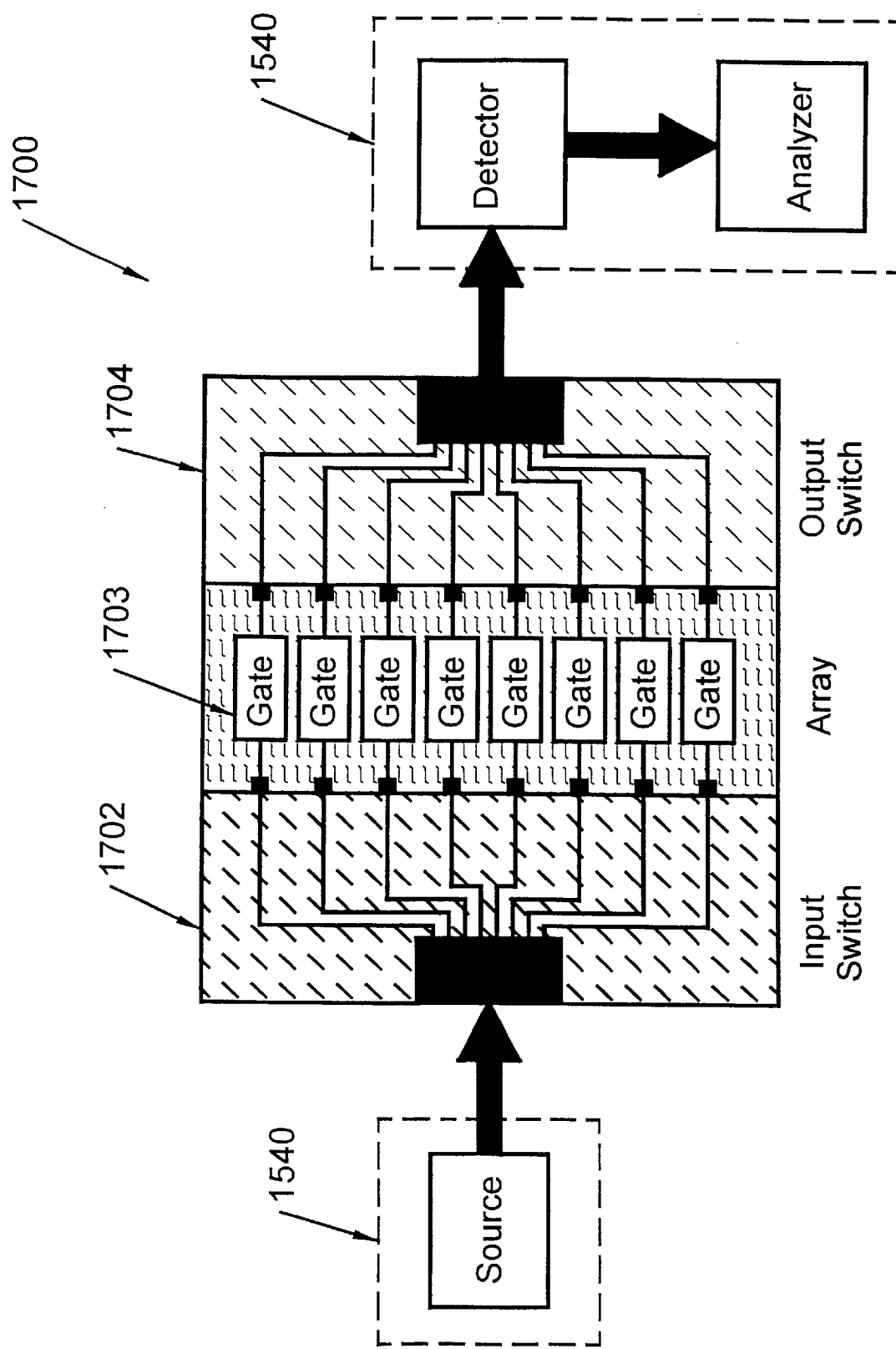
FIG. 13A illustrates one embodiment of a bio-assay array in accordance with the present invention.

FIG. 13A illustrates one embodiment of an integrated bio-assay array 1700 in accordance with the present invention. The integrated array 1700 is supplied with a test signal via the signal source of measurement system 1540. The array 1700 includes an integrated 1×N input switch 1702 and a M×1 output switch 1704 which are monolithically formed during the semiconductor fabrication process. The number of inputs may be the same as the number of outputs in which case M=N, the number of inputs and outputs may differ.

The 1×N input switch 1702 routes the incoming test signal to the desired array element within array 1703. The MBR in the array element 1703$_i$ modulates the test signal according to the dielectric properties of the molecular binding events which make up the MBR. An M×1 output switch 1704 routes the modulated test signal to a detector of the measurement system 1540. An analyzer of the test system 1540 compares the input and modulated test signals to determine the measured signal response. While each array element 1703$_i$ is illustrated as a two-port device, those of skilled in the art will appreciate that one-port or multiple port array elements may be used alternatively.

As explained above, the array 1703 and the input and output switches 1702 and 1704 may be fabricated either as discrete components or in wafer form and integrated in varying degrees depending upon the application. In the illustrated embodiment, the array 1703 and input and output switches 1702 and 1704 are monolithically formed on a semiconductor wafer. In another embodiment, the input and output switches 1702 and 1704 are monolithically formed separately from the detector array 1703 and connected via wire or ribbon bonds. In a further embodiment, input and output switches 1702 and 1704 and array 1703 are each discrete units. Those skilled in the art will appreciate that other arrangements are also possible.

Figure 13B:
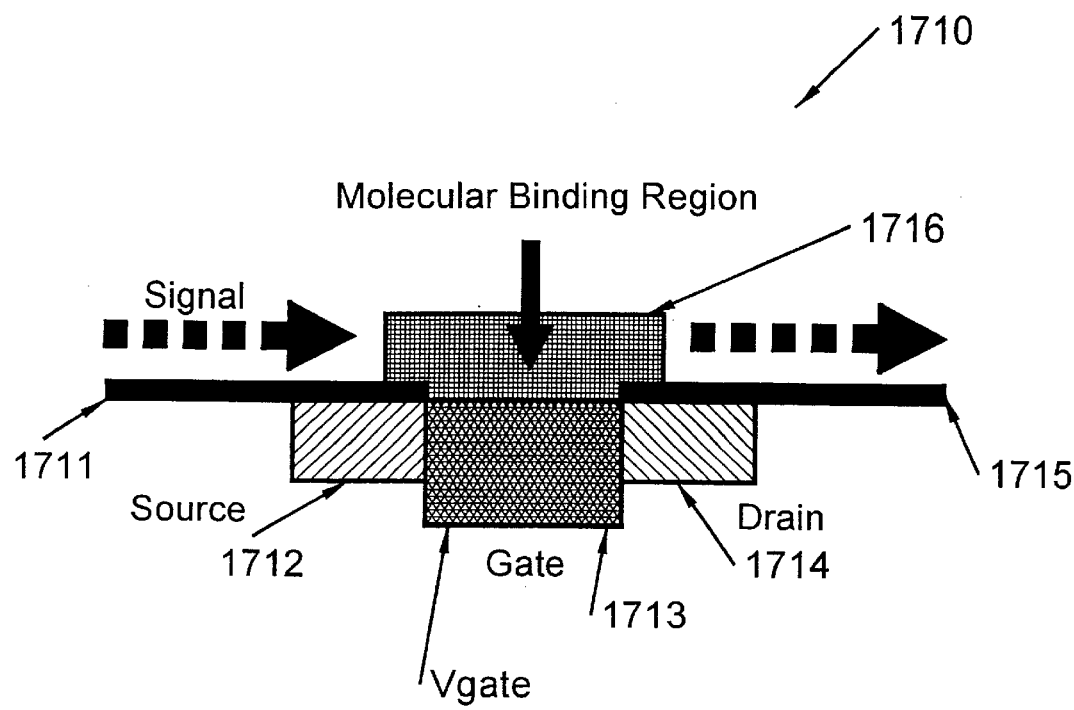
FIG. 13B illustrates one embodiment of an array element in accordance with the present invention comprising a series-connected, electronically switched field Effect Transistor.

FIG. 13B illustrates one embodiment of an array element, shown as a series connected, electronically switched Field Effect Transistor (FET) 1710. FET 1710 may be a Metal Semiconductor Field Effect Transistor (MESFET) fabricated using GaAs processing. Other transistor configurations are also possible for instance, High Electron Mobility Transistors (HEMT), heterostructure FETs, homogenous or heterojunction bipolar transistors, or PN junctions devices such as PIN diodes to name a few. Other active or passive array elements may be used alternatively or addition to these as well.

In the embodiment of FIG. 13B, the source and drain terminals 1712 and 1714 of FET 1710 are employed as the input and output ports, 1711 and 1715 respectively, and the on/off state of the FET 1710 is controlled via a voltage applied to the gate terminal 1713. The sample is applied over FET 1710 such that the MBR 1716 provides a parallel path between the source and drain terminals 1712 and 1714. FET 1710 is designed such that when turned off, it presents a drain to source resistance ($R_{ds}$) which is much higher than resistance through the MBR 1716. In this instance, the signal path propagates through the MBR 1716 which modulates the test signal. The modulated test signal is recovered (through a DC blocking capacitor to remove the DC bias) and compared to the input test signal to detect and/or identify the molecular binding events occurring within the MBR 1716.

When the FET 1710 is activated, it provides a much lower $R_{ds}$ compared to the resistance of the MBR 1716. In this instance, the MBR 1716 is effectively switched out of the signal path and the signal propagates largely unaffected by it. Thus by simply opening or closing a switch, an array element may be addressed.

Figure 13C:
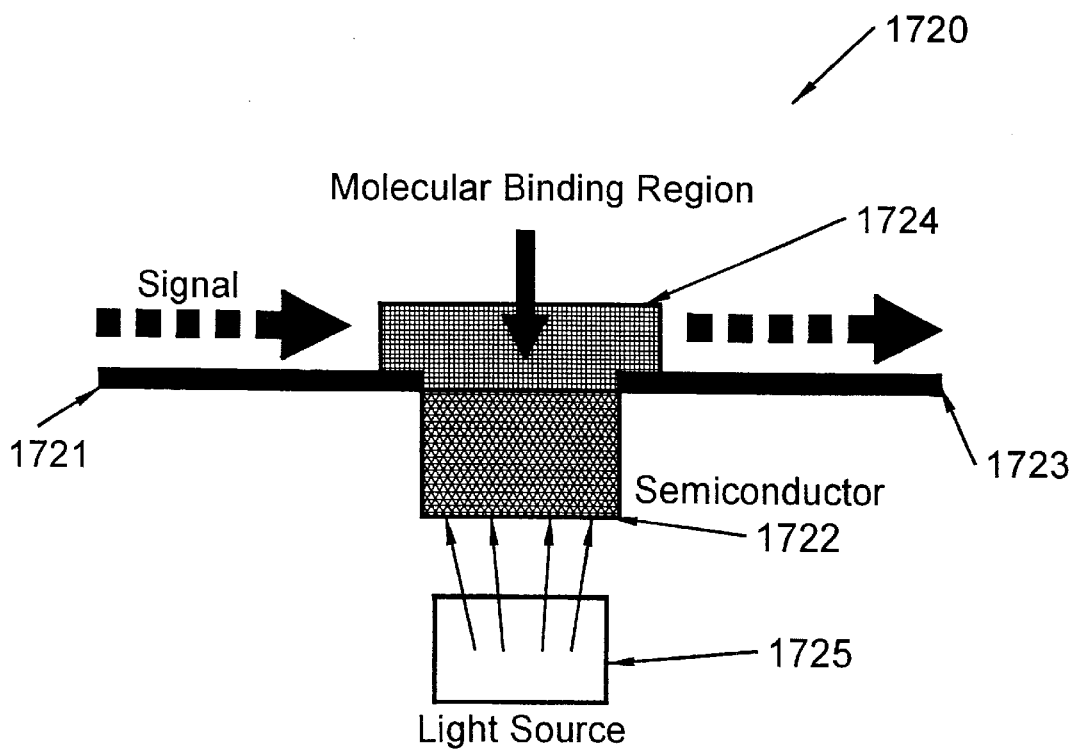
FIG. 13C illustrates one embodiment of an array element in accordance with the present invention comprising a series-connected, optically switched Field Effect Transistor.

FIG. 13C illustrates a further embodiment of a FET used as an array element which is optically switched. FET 1720 is connected similarly to FET 1710 described in FIG. 13B and may consist of a photosensitive transistor, diode or other photosensitive device. The gate junction 1722 may be illuminated, for instance, with normal sunlight, a laser, a Light Emitting Diode (LED), or other source having a wavelength to which FET 1720 has a high sensitivity. The incident light activates FET 1720 to switch out the MBR 1722. When the FET 1720 is deactivated, the test signal propagates from the FET input 1721 to the FET output 1723, through the MBR 1722 and is modulated thereby. The modulated test signal is recovered (through a DC blocking capacitor not shown) and analyzed to determine the presence and/or identity of molecular binding events within the MBR 1722.

Figure 13D:
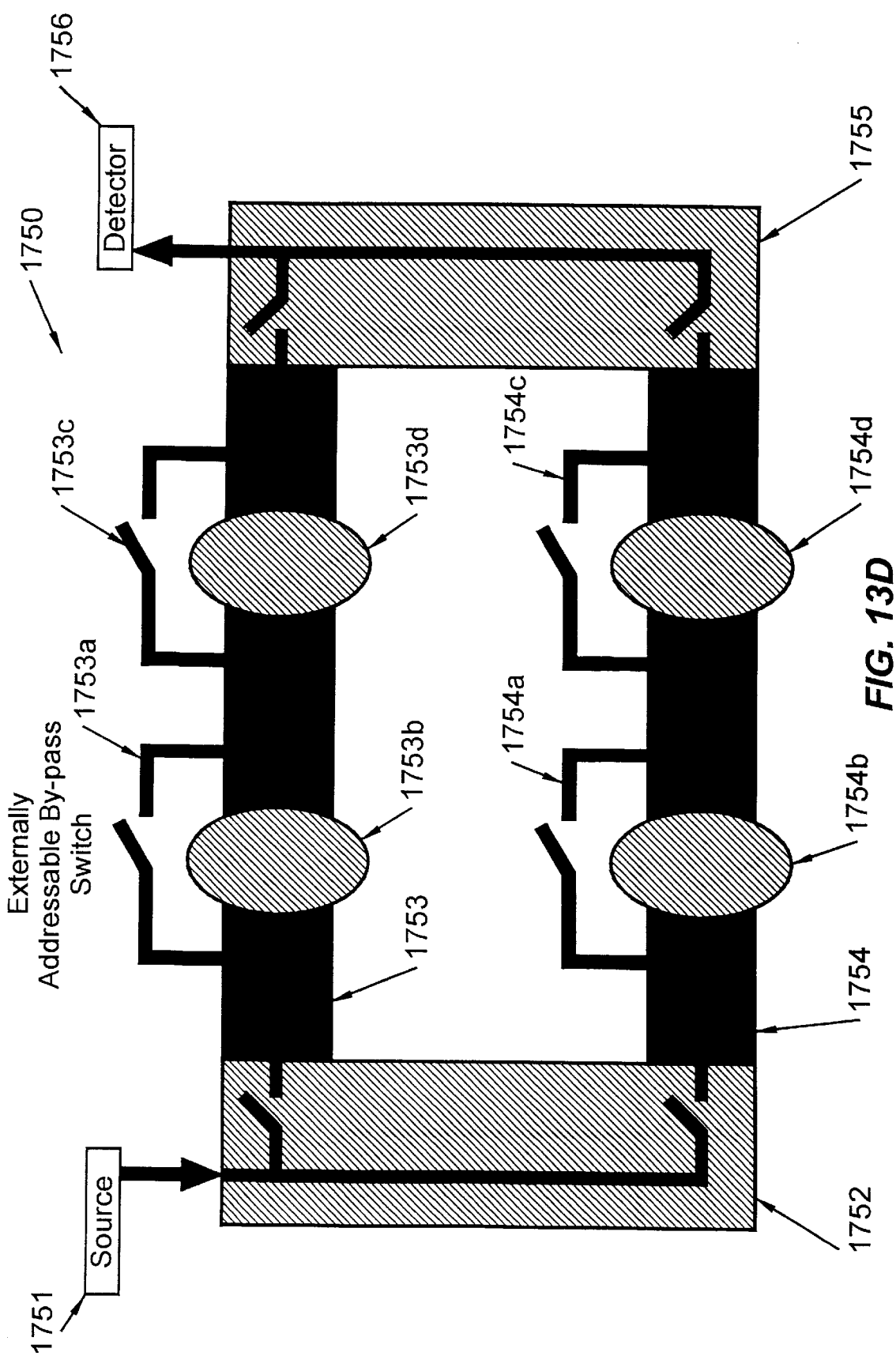
FIG. 13D illustrates one embodiment of an array in accordance with the present invention comprising two paths of two, serially-connected FET devices.

FIG. 13D illustrates an extension of FIG. 13B and 13C in which two or more FETs are serially-connected. Array 1750 includes a first test path 1753 along which addressable switches 1753a and 1753c are coupled. In one embodiment, addressable switches are electronically or optically controlled MESFETs, described above. Array path 1753 further includes sample regions 1753b and 1753d, each of which provides a parallel signal paths to the corresponding addressable switches 1753a and 1753c.

As described above, addressable switches 1753a and 1753c operate to switch in and out the sample regions 1753b and 1753d between a signal source 1751 and a signal detector 1756 via input switch 1752 and output switch 1755. Thus, a particular row is made into a transmission path in which a single assay site appears as an impedance mismatch. Each assay site can be either switched into the circuit, or switched out of the circuit, as desired. The nature of the impedance mismatch is a function of binding and other changes in the MBR. Additional signal paths such as signal path 1754 (having addressable switches 1754a and 1754c connected in parallel to sample regions 1754b and 1754d) may be included in the array and cross-strapped to the other paths using other low loss switches (not shown) to allow the test signal to propagate between signal paths 1753 and 1754. Input and output switches 1752 and 1755 are used to inject and recover the test signal to/from the array 1750. As those of skill in the art will appreciate, the described array may be extended to any number of N×M elements to provide a two dimensional array device.

Figure 13E:
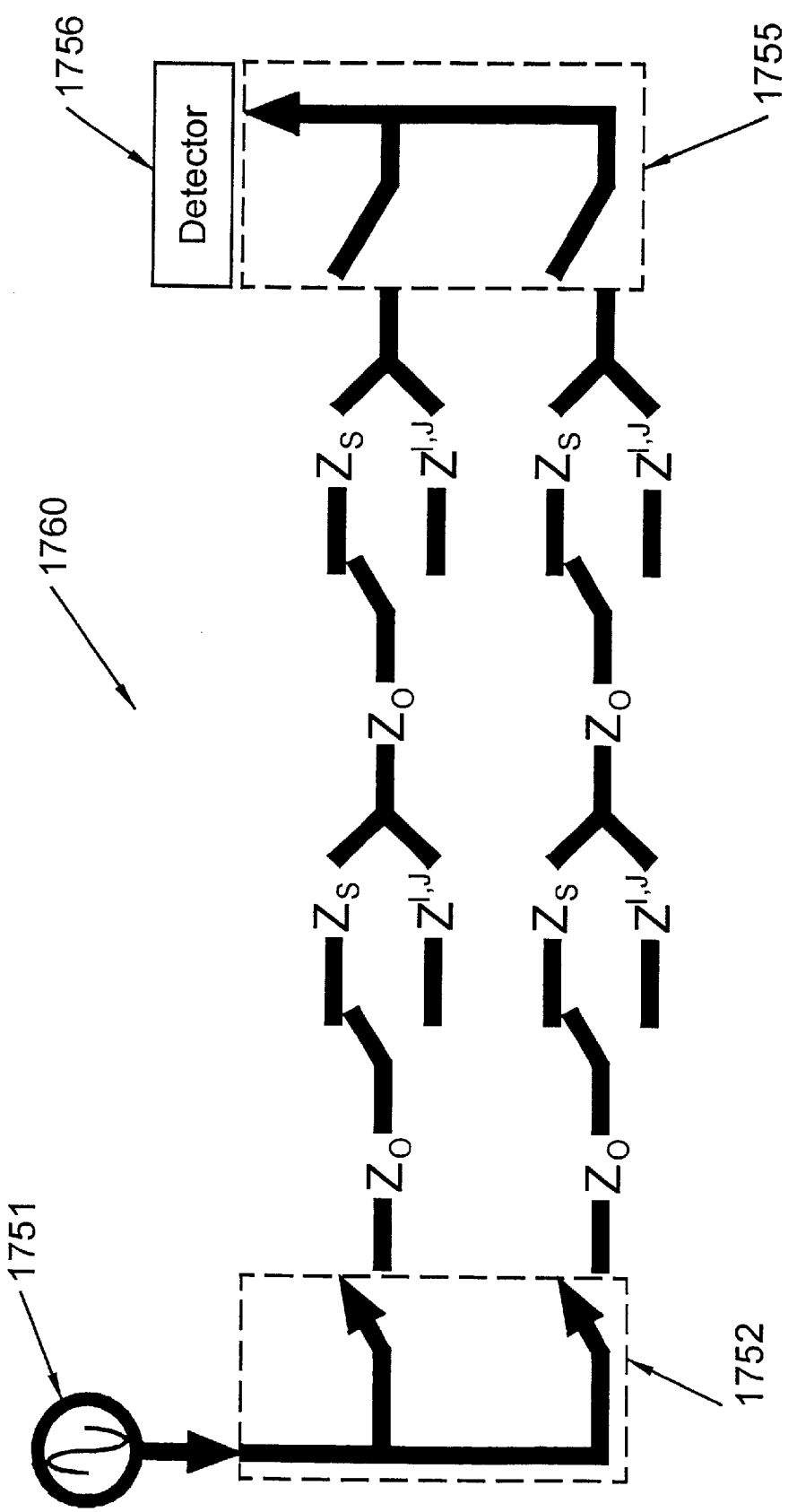
FIG. 13E illustrates the circuit equivalent model of the array shown in FIG. 7D in accordance with the present invention.

FIG. 13E illustrates the circuit equivalent model of the array shown in FIG. 13D. The input source 1751, input switch 1752, output switch 1755, and signal detector 1756 are as illustrated in FIG. 13D. The switch impedance ZS is designed to be a close match with the reference impedance of the signal path ZO, and the assay impedance $Z^{I,J}$ is designed to be much different than either the switch or reference impedance. Thus, small changes in the assay impedance will dominate the electrical properties of any given row, and will therefore be easily detectable. The exact values for the impedances will depend on the design criteria for the particular array, but certain general principles of engineering apply, such as the greatest efficiency in terms of delivering power to the load (detector) is obtained with matched-impedance design, and reference impedances are frequently taken to be 50Ω.

In an alternative embodiment, each array element may consist of a logic gate which is capable of occupying one of two possible states, depending on the conditions of gating. As an example, the conditions of gating may be whether or not a particular binding event has occurred. Such a condition may be the hybridization of nucleic acid material to specific capture probes on the surface of the device, or a particular drug-receptor interaction. In any case, the device is engineered so that a binding event or structural change in the MBR triggers the gating. Essentially the modulation of any circuit parameter may trigger the gating; all that is required is to have the necessary hardware and software in place to make the decision as to whether or not the circuit parameter has been modulated.

As an example, one may monitor a characteristic frequency of a given system such as a resonant structure. The shift in this frequency as a result of a particular binding event may serve as the modulation which signals the logic state. Any parameter which changes as a function of binding may be used to trigger logic gate. Such parameters include, but are not limited to: frequency, voltage, current, power, phase, delay, impedance, reactance, admittance, conductance, resistance, capacitance, inductance, or other parameters.

Figure 13F:
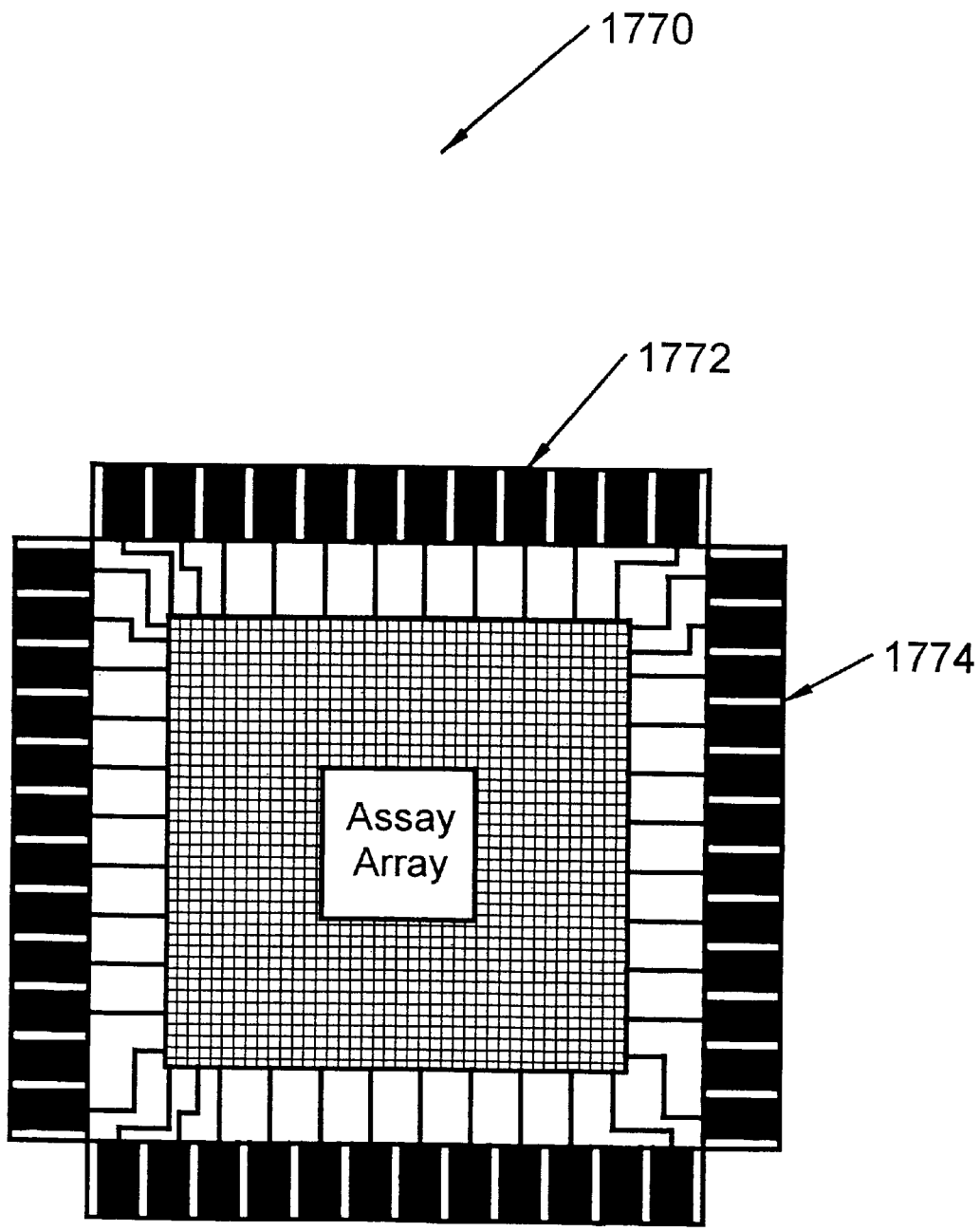
FIG. 13F illustrates one embodiment of a two-dimensional bio-assay array in accordance with the present invention.

FIG. 13F illustrates one embodiment of a two-dimensional bio-assay array 1770. As shown, the array 1770 includes a first input/output (I/O) axis 1772 and a second I/O axis 1774 for inputting/outputting test signals.

The array is interfaced with conventional external diagnostic hardware which is capable of generating and detecting the appropriate frequency or frequencies, then communicating it to and from the assay array via a multiplexer, through the ports as illustrated above. Such an externally supported system may be comprised of any number of electromagnetic sources such as vector and scalar network analyzers, time-domain devices like TDR analyzers and other pulsed techniques; utilize any of the detection schemes mentioned herein, including vector and network analyzers; and use any number of well-known techniques to deliver the signals to and from the assay array via standard and non-standard multiplexing techniques.

Generically, such a chip may be fabricated using standard semiconductor chip approaches. Those of skill in the art will readily appreciate that such a configuration may be used in a one-port format, a two port format, or utilize more than two ports.

The bio-electrical interface region consists of a signal path designed to support the propagation of an electromagnetic signal at the desired test frequency. Many configurations are possible, one example being a sputtered gold transmission line operable between D.C. and 110 GHz. In another embodiment, the signal path consists of a dielectric medium, such as the MBR itself. In this embodiment, the signal path blocks DC voltages and currents but otherwise supports the propagation of the desired test signal, occurring at frequencies, for instance 1 MHz, 5 MHz 10 MHz, 20 MHz, 45 MHz, 80 MHz, 100 MHz, 250 MHz, 500 MHz, 750 MHz, 1 GHz, 2.5 GHz, 5 GHz, 7.5 GHz, 10 GHz, 12 GHz, 18 GHz, 20 GHz, 22 GHz, 24 GHz, 26 GHz, 30 GHz, 33 GHz, 40 GHz, 44 GHz, 50 GHz, 80 GHz, 96 GHz, 100 GHz, 500 GHz, 1000 GHz, or frequencies ranging therebetween. Accordingly, the signal path is designed using high frequency circuit design techniques, known in the art. Such design techniques include impedance matching the signal path to the interconnecting structures, minimizing the insertion loss of the signal path, and minimizing the Voltage Standing Wave Ratio (VSWR) of the signal path. In the preferred embodiment of the present invention, the signal path and MBR are oriented in a non-orthogonal orientation.

The present invention is not limited to the detection of a molecule of an anticipated size or structure attached to the signal path. The MBR may consist of 1, 2, 3, 4, 5, 10, 20, 30, 50, 100, 1000, or more molecular lengths attached or separated from but coupled to the signal path. Further, the MBR may consist of a multiple layers of homogeneous molecules, a single but heterogeneous molecular layer or multiple heterogeneous molecular layers.

Additional information regarding arrays of the present invention is described in a copending and commonly owned U.S. application entitled "Test Systems and Sensors for Detecting Molecular Binding Events", U.S. Ser. No. 09/365,978, which was filed on the same date as the present application and which was previously incorporated herein by reference in its entirety for all purposes.

VIII. Synthesis of Probe Arrays

Nucleic acid arrays for hybridization methods such as those provided for by the present invention can be prepared in two general ways. One approach involves binding DNA from genomic or cDNA libraries to some type of solid support, such as glass for example. (See for example, Meier-Ewart, et al., Nature 361:375–376 (1993); Nguyen, C. et al., Genomics 29:207–216 (1995); Zhao, N. et al., Gene, 158:207–213 (1995); Takahashi, N., et al., Gene 164:219–227 (1995); Schena, et al., Science 270:467–470 (1995); Southern et al., Nature Genetics Supplement 21:5–9 (1999); and Cheung, et al., Nature Genetics Supplement 21:15–19 (1999), each of which is incorporated herein in its entirety for all purposes.)

The second general approach involves the synthesis of nucleic acid probes. One method involves synthesis of the probes according to standard automated techniques and then post-synthetic attachment of the probes to a support. See for example, Beaucage, Tetrahedron Lett., 22:1859–1862 (1981) and Needham-VanDevanter, et al., Nucleic Acids Res., 12:6159–6168 (1984), each of which is incorporated herein by reference in its entirety. A second broad category is the so-called "spatially directed oligonucleotide synthesis" approach. Methods falling within this category further include, by way of illustration and not limitation, light-directed oligonucleotide synthesis, microlithography, application by ink jet, microchannel deposition to specific locations and sequestration by physical barriers.

Light-directed combinatorial methods for preparing nucleic acid probes are described in U.S. Pat. Nos. 5,143,854 and 5,424,186 and 5,744,305; PCT patent publication Nos. WO 90/15070 and 92/10092; Fodor et al., Science 251:767–777 (1991); and Lipshutz, et al., Nature Genetics Supplement 21:20–24 (1999), each of which is incorporated herein by reference in its entirety. These methods combine solid-phase chemical synthesis and semiconductor-based lithography. Briefly, such methods begin with the attachment of linkers modified with photochemically removable protecting groups to a solid substrate. Light is directed through a photolithographic mask to specific areas of the synthesis surface, activating those areas for chemical coupling. The first of a series of nucleosides which includes a photo-liable protecting group at the 5' end is incubated with the array; chemical coupling occurs at those sites that have been illuminated in the preceding step. A different mask is then aligned with the chip and light is directed to a different region of the substrate through this mask, and the chemical cycle repeated. Through appropriate selection of masks and chemical steps, a defined collection of oligonucleotides can be synthesized at predefined positions on the surface of the array. An algorithm for design of masks to reduce the number of synthesis cycles is described in U.S. Pat. Nos. 5,571,639 and 5,593,839 to Hubbel et al., and by, Fodor et al., Science 251:767–777 (1991), each of which is incorporated herein by reference in its entirety.

Other combinatorial methods which can be used to prepare arrays for use in the current invention include spotting reagents on the support using ink jet printers. See Pease et al., EP 728, 520, and Blanchard, et al. Biosensors and Bioelectronics II: 687–690 (1996), which are incorporated herein by reference in their entirety. Arrays can also be synthesized utilizing combinatorial chemistry by utilizing mechanically constrained flowpaths or microchannels to deliver monomers to cells of a support. See Winkler et al., EP 624,059; WO 93/09668; and U.S. Pat. No. 5,885,837, each of which is incorporated herein by reference in its entirety.

IX. Attaching Nucleic Acid Probes to Transmission Line

The transmission line is generally constructed of materials which exhibit appropriate conductivity over the desired test frequency range and which possess good molecular binding qualities as described above. Such materials include, but are not limited to gold, indium tin oxide (ITO), copper, silver, zinc, tin, antimony, gallium, cadmium, chromium, manganese, cobalt, iridiuim, platinum, mercury, titanium, aluminum, lead, iron, tungsten, nickel, tantalum, rhenium, osmium, thallium or alloys thereof. The conductive layer may also be formed from semiconducting materials which may be either crystalline or amorphous in structure, including chemically doped or pure carbon, silicon, germanium, gallium-arsenide, idium-gallium arsenide, glass, quartz, ceramics, or the like. The conductive material may also be formed from polymers including, by way of illustration and not limitation, polyethylene, polypropylene, polyacetylene, polythiophene and the like.

In general, nucleic acids may be attached to the transmission line through electrostatic interactions or covalent bonds, for example. Attachment can be achieved by utilizing various functional groups on the nucleic acid and/or the transmission line. Examples of such functional groups include, for example, thiols, carboxylic acids, silanes, siloxanes, amides, succinimides, and acyl chlorides.

Nucleic acids can be attached directly to the transmission line or, as described in association with FIGS. 1D–1F, the nucleic acid can be attached via one or more linkers. A linker is a molecule that may be used to join the biological binding partner (e.g. ligand or antiligand) to the underlying (e.g. apparatus or device) surface. The linker is capable of forming covalent bonds with a nucleic acid and the transmission line. A bifunctional linker having one functional group which can react with a group on the surface of the transmission line, and another group reactive with the nucleic acid can be used to form the desired conjugate. Many procedures and linker molecules for attachment of various biological molecules to various metal, glass, and plastic substrates are known in the art. See, for example, European Patent Application No. 188,256; U.S. Pat. Nos. 4,671,958; 4,659,839; 4,414,148; 4,699,784; 4,680,338; 4,569,789; and 4,589,071; and Borlinghaus et al., Cancer Res. 47: 4071–4075 (1987). An illustrative but non-exhaustive list of linkers that can be used with nucleic acids include polyethylene glycol, thiols, functional alkanes, peptides and other nucleic acids.

In one embodiment, the transmission line is gold and the nucleic acid is attached to the transmission line through a nucleic acid having a thiol group attached thereto (preparation of thiolated nucleic acids is described in James D. Watson, et al., Recombinant DNA, $2^{nd}$ Edition, Scientific American Books, NY 1992, which is incorporated herein by reference in its entirety). One method for fabricating a gold transmission line is as follows. A support material such as glass or other inexpensive, relatively smooth material is used as the underlying physical structure. On top of this material a thin layer of titanium (10–100 Angstroms) is deposited through thermal evaporation, sputtering, chemical vapor deposition or other means. The titanium acts as an adhesive layer between the gold and support. Subsequent to titanium deposition, gold (10–10000 Angstroms) is deposited through thermal deposition, sputtering, chemical vapor deposition, or like methods.

Derivatized nucleic acids having a disulfide terminus can be attached to the gold line. The disulfide functionality on the nucleic acid can be reduced with dithiothreitol before use, or the nucleic acid can be attached directly via the disulfide. The nucleic acid (either reduced to thiol or as disulfide) is prepared in a buffer solution. Attachment is achieved, for example, by dipping the transmission line into the solution, flowing the solution across the transmission line, or wicking the solution onto the transmission line. The transmission line is subsequently washed to remove any unbound material and is then ready for use in a hybridization experiment.

In other instances, the transmission line can be manufactured from indium tin oxide and attached to a nucleic acid using silanized nucleic acids (preparation of silanized nucleic acids is described for example, in James D. Watson, et al., Recombinant DNA, $2^{nd}$ Edition, Scientific American Books, NY 1992). An indium tin oxide (ITO) transmission line can be prepared by sputtering tin doped indium in a sputtering chamber. The support material can include, for example, glass, plastic or silicon. The resulting ITO fabricated support is then typically baked in an oven at 400° C. for several hours to induce greater conductivity as desired. Silanized nucleic acids can be prepared in a buffer and then contacted with the transmission line, for example, by dipping the transmission line into the DNA solution, flowing buffer across the transmission line in a cell, or wicking the solution onto the transmission line. The fabricated product is then washed with distilled water and heated at 80–90° C. for 60–120 minutes; the resulting transmission line is then ready for use.

X. Target Nucleic Acids

A. General

A target sequence is generally a known sequence, or a variant of a known or partly known reference sequence. However, in some instances, such as de novo sequence analysis, for example, the sequence of the target nucleic acid is unknown. A target sequence often encodes a gene or part of a gene. Often the target sequence contains one or more known polymorphic sites. The function of the target sequence may or may not be known.

The target nucleic acid can be genomic, RNA or cDNA. Genomic DNA samples are usually amplified before application to an array using primers flanking the region of interest. Genomic DNA can be obtained from virtually any tissue source (other than pure red blood cells). For example, convenient tissue samples include whole blood, semen, saliva, tears, urine, fecal material, sweat, buccal, skin and hair.

In some instances, it is helpful to amplify the target sequence to aid in detection. However, because the methods of the present invention are more sensitive than other nucleic acid detection methods and not subject to interference from background it is possible in some instances to avoid having to amplify the sequence of interest or to at least reduce the extent to which the sequence must be amplified.

Amplification of genomic DNA containing a polymorphic site generates a single species of target nucleic acid if the individual from the sample was obtained is homozygous at the polymorphic site or two species of target molecules if the individual is heterozygous.

RNA samples are also often subject to amplification. In this case amplification is typically preceded by reverse transcription. Amplification of all expressed mRNA can be performed as described in publications WO 96/14839 and WO 97/01603. Amplification of an RNA sample from a diploid sample can generate two species of target molecule if the individual from whom the sample was obtained is heterozygous at a polymorphic site occurring within expressed RNA.

The PCR method of amplification is described in *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202 (each of which is incorporated by reference for all purposes). Nucleic acids in a target sample are usually labeled in the course of amplification by inclusion of one or more labeled nucleotides in the amplification mix. Labels can also be attached to amplification products after amplification e.g., by end-labeling. The amplification product can be RNA or DNA depending on the enzyme and substrates used in the amplification reaction.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

XI. Label Free Analysis

With the detection system of the present invention, binding events can be detected without the use of labels. This is true of hybridization between probes and targets as well. Nearly all current hybridization methods require the use of labels as a way to identify which probes have hybridized to a target. The types of labels used in existing methods vary, but frequently include radioactive labels or fluorescent labels. Because the methods of the present invention involve direct detection, it is not necessary to prepare labeled nucleic acids prior to conduct an experiment, thus simplifying the procedure and reducing costs. Not having to use labels also insures that there is no steric hindrance caused by the presence of the label which might interfere with the hybridization process. Furthermore, unlike most other methods, the methods described herein are insensitive to background signal resulting from unbound labeled nucleic acids (e.g., background fluorescence resulting from unbound nucleic acids). This means that the methods of the present invention can monitor the hybridization process in real time, thereby allowing kinetic studies to be undertaken. Although labels are not necessary with the present invention, the nature of the detection system does not preclude their use.

XII. Analysis Utilizing Hybridization Fingerprints or Profiles

A. Acquiring a Fingerprint or Profile

With the detection system of the present invention it is possible to obtain spectral scans which include signals that are characteristic for certain ligand/antiligand complexes or for certain types of binding interactions. Such scans are referred to herein as profiles or fingerprints. Profiles can be obtained for essentially any type of ligand/antiligand complex. Such profiles are particularly useful in studying nucleic acid hybridization complexes. As described in greater detail below, profiles can be used in identifying the formation of a particular complex, detecting the presence of certain nucleic acids, and distinguishing between different types of binding interactions.

Hence, certain methods of the present invention include determining the profile or fingerprint for various types of ligand/antiligand complexes, in particular various types of hybridization complexes. Within the context of nucleic acid studies, such a process typically involves monitoring an electromagnetic signal transmitted down a signal path to which a probe that is hybridized to a target is electromagnetically coupled. A response signal (transmitted and/or reflected) generated from interaction of the transmitted signal with the hybridization complex is monitored as either the frequency or wavelength is scanned over a desired range to obtain a spectrum which depicts the response signal as a function of the frequency or wavelength. Since each hybridization complex gives a different spectrum, the spectrum can serve as a profile or fingerprint for that particular complex.

For example, it is possible to identify certain peaks or signals at particular frequencies in the spectrum which are unique to a particular hybridization complex. By monitoring such characteristic peaks, it is possible to distinguish between complementary and mismatched hybridization complexes, quantitate the amount of a particular complex and conduct kinetic studies, for example.

By repeating this analysis with numerous different hybridization complexes, a database of profiles or fingerprint can be accumulated. By storing these profiles in an electronic storage medium, the profiles can be rapidly accessed during an experiment and compared to an experimental spectrum to aid in the types of analyses just listed.

B. Distinguishing between Complementary and Non-complementary Hybridization Complexes The profiles just described have utility in distinguishing between a complementary and mismatch complex. In general, a spectrum is obtained for a test sample in the usual way by measuring a signal generated from a hybridization complex between a probe and target. The resulting spectrum is then examined for the presence of a complementary signal or a mismatch signal. A complementary signal is one which is characteristic for a complementary complex between a particular probe and a particular target which have complementary sequences. Similarly, a mismatch signal is a signal which is characteristic for a mismatch complex formed between a specific probe and a specific target which are substantially complementary but which include one or more mismatches. The presence of the complementary signal indicates that the complex between probe and target is complementary, whereas the mismatch signal indicates that the probe and target form a mismatch complex. Using a database containing data for many different mismatches, it is possible in some instances not only to identify the existence of a particular mismatch, but to identify what type of mismatch exists in the hybridization complex, i.e., it is possible to identify the base at the mismatch site.

In certain embodiments utilizing profiles to analyze hybridization complexes, it is unnecessary to conduct stringency washes to remove unbound nucleic acids which fail to form a hybridization complex with the nucleic acid probe. In existing methods, either the nucleic acid probe or the nucleic acid target, generally the latter, are labeled. Because conventional techniques differ from the methods of the present invention in that they can not directly detect hybridization complexes, labeled nucleic acids must be used to identify which probes have formed hybridization complexes. Such methods require stringency washes for at least two reasons. First, it is necessary to remove unbound labeled nucleic acids so it is possible to distinguish between signals resulting from hybridized and unhybridized nucleic acids. Secondly, the washes must be performed under stringent conditions because current methodologies can not differentiate between complementary hybridization complexes and mismatch hybridization complexes.

In contrast, using the profiles just described, it is possible not only to differentiate between bound nucleic acids and unbound nucleic acids, but also possible to distinguish between complementary and mismatch hybridization complexes. In fact, as described further in Example II below, it is possible to distinguish between single mismatches. In some instances, it may be necessary to wash the probes of unbound molecules. However, even in such instances, it is still often possible using hybridization profiles to reduce the amount of washing and/or reduce the stringency of wash conditions, thereby allowing greater flexibility in analysis.

The ability to avoid stringency washing through the use of profiles means that it is possible to simplify nucleic acid analysis by avoiding a complex step of standard techniques, thus also allowing analyses to be performed in a more rapid and cost effective manner. It thus enables certain methods to be performed as homogenous assays, i.e., as assays wherein a separation step is not required. Profiles can also be used to make quantitative measurements for different hybridization complexes.

XIII. Quantitative Analysis

The fact that the detection methods can be performed without label (and thus signals monitored in real time) and that it is possible to correlate certain signals with particular hybridization complexes (i.e., to develop hybridization profiles) makes it is possible to perform certain quantitative analyses. For example, certain signals in a spectrum shown previously to be correlated with a particular complex can be measured with time to obtain kinetic information regarding the rate of hybridization. Measurements may include, for example, measuring signal amplitudes or a shift in signal frequency. Other changes could also be monitored.

It is also possible to compare the rate of change of various signals to obtain relevant information regarding the hybridization process. For example, complementary hybridization complexes form more quickly than mismatch hybridization complexes. Thus, differences in the rate of change of different signals within the spectrum can be used to differentiate between complementary and mismatch hybridization complexes. By monitoring complementary signals and mismatch signals it is also possible to compare hybridization rates for complementary complexes and mismatch complexes. Such rate studies can be used to assess the number of mismatches in a hybridization complex, for example.

XIV. Expression Analysis

A. General

Certain methods of the present invention involve the analysis of gene expression levels. In general terms, expression analysis involves the detection and quantification of mRNA levels in one or more samples. Expression analysis provides key insight into a variety of biological phenomenon. Cellular development and differentiation is one area in which expression analysis finds particular utility. In any given cell, only a fraction of all the encoded genes are expressed. The levels and timing of expression control cellular development, differentiation, function and physiology. Thus, monitoring gene expression can be used to analyze these processes. As an example, expression analysis can be utilized to assess differences in expression between different types of tissue. Expression studies can also provide important information into the genetic basis for aging and phenotypic differences.

Expression analysis can also be of value in studies of various diseases. For instance, expression analysis can be used to analyze the development and progression of cancer, since these events are accompanied by complex changes in the pattern of gene expression. Such studies can involve, for example, a comparison of gene expression in diseased tissue and normal tissue or infected tissue and normal tissue. Expression analysis can also be used in other clinical applications, including evaluating the effects of various drug treatments on expression. For example, variations in gene expression for normal tissue treated with drugs or a drug candidate and normal tissue can be compared. Similar drug studies could be performed with diseased tissue and normal tissue. By determining which genes are expressed in various diseases, it is possible to identify genes or their protein products that could be drugs or drug targets. In other clinical applications, expression analysis can be used in toxicological evaluations by comparing expression levels between tissue treated with poison or toxins and normal tissue. Of course, expression analysis can be used in a variety of other comparative studies to assess the impact of variations in gene expression.

General methods for using arrays of nucleic acid probes for monitoring expression of mRNA molecules are described in PCT/US/96/143839 and WO 97/17317, which are incorporated herein by reference in their entirety. These methods utilize nucleic acids probes which are complementary to mRNA targets of interest or amplification products therefrom. In general, mRNA molecules or amplification products generated therefrom are applied to the nucleic acid probes to identify targets of interest. In some instances, binding of target to probes known to be mismatched with the target can be used to control for nonspecific binding.

Additional discussion regarding the use of microarrays in expression analysis can be found in Duggan, et al., Nature Genetics Supplement 21:10–14 (1999); Bowtell, Nature Genetics Supplement 21:25–32 (1999); Brown and Botstein, Nature Genetics Supplement 21:33–37 (1999); Cole et al., Nature Genetics Supplement 21:38–41 (1999); Debouck and Goodfellow, Nature Genetics Supplement 21:48–50 (1999); Bassett, Jr., et al., Nature Genetics Supplement 21:51–55 (1999); and Chakravarti, Nature Genetics Supplement 21:56–60 (1999), each of which is incorporated herein by reference in its entirety.

B. RNA Preparation and Hybridization

As described above, samples can be obtained from essentially any source from which nucleic acids can be obtained. Cells in the sample can be disrupted in a variety of ways to release the RNA therein (see for example, Watson, et al., Recombinant DNA, $2^{nd}$ Edition, Scientific American Books, NY 1992, which is incorporated herein by reference in its entirety). For example, nucleic acids may be released by mechanical disruption (such as repeated freeze/thaw cycles, abrasion and sonication), physical/chemical disruption, such as treatment with detergents (e.g., Triton, Tween, or sodium dodecylsulfate), osmotic shock, heat, or enzymatic lysis (e.g., lysosyme, proteinase K, pepsin, etc.).

Once nucleic acids have been obtained, they typically are reversed transcribed into cDNA, although mRNA could be used directly. Following formation of the cDNA, generally sequences of interest are amplified according to any of the various amplification techniques which are known in the art and described above.

A sample containing the nucleic acids is then contacted with a probe, normally a multitude of probes that are part of an array. After allowing a period for targets to hybridize to the probes, in some methods the probes are stringency washed to remove unbound target and to minimize nonspecific binding to the nucleic acid probes of the arrays. However, such washes may not be necessary because of the ability of the current detection system to distinguish between perfectly complementary binding and binding involving mismatches as described above.

Because the current methods do not require labeling of the target molecules, there is no background signal to subtract out. This means that measurements can be made in real time, thus allowing the kinetics of binding to be monitored and making it possible to distinguish spectroscopically between perfectly complementary and mismatched binding.

C. Types of Arrays

The probes utilized in the arrays of the present invention can include, for example, synthesized probes of relatively short length (e.g., a 20-mer or a 25-mer), cDNA (full length or fragments of gene), amplified DNA, fragments of DNA (generated by restriction enzymes, for example) and reverse transcribed DNA. For a review on different types of microarrays, see for example, Southern et al., Nature Genetics Supplement 21:5–9 (1999), which is incorporated herein by reference.

1. Synthesized Arrays

In general, two major categories of arrays can be utilized with the expression analysis methods of the present invention: custom arrays and generic arrays. Custom arrays are useful for detecting the presence and/or concentration of a particular mRNA sequences that are known in advance. In such arrays, nucleic acid probes can be selected to hybridize to particular preselected subsequences of mRNA gene sequences or amplification products prepared from them. In some instances, such arrays can include a plurality of probes for each mRNA or amplification product to be detected.

The second type of array is sometimes referred to as a generic array because the array can be used to analyze mRNAs or amplification products generated therefrom irrespective of whether the sequence is known in advance of the analysis. Generic arrays can be further subdivided into additional categories such as random, haphazardly selected, or arbitrary probe sets. In other instances, a generic array can include all the possible nucleic acid probes of a particular pre-selected length.

A random nucleic acid array is one in which the pool of nucleotide sequences of a particular length does not significantly vary from a pool of nucleotide sequences selected in a blind or unbiased manner form a collection of all possible sequences of that length. Arbitrary or haphazard nucleotide arrays of nucleic acid probes are arrays in which the probe selection is made without identifying and/or preselecting target nucleic acids. Although arbitrary or haphazard nucleotide arrays can approximate or even be random, the methods by which the array are generated do not assure that the probes in the array in fact satisfy the statistical definition of randomness. The arrays can reflect some nucleotide selection based on probe composition, and/or non-redundancy of probes, and/or coding sequence bias; however, such probe sets are still not chosen to be specific for any particular genes.

Alternatively, generic arrays can include all possible nucleotides of a given length; that is, polynucleotides having sequences corresponding to every permutation of a sequence. Thus since the polynucleotide probes of this invention preferably include up to 4 bases (A, G, C, T) or (A, G, C, U) or derivatives of these bases, an array having all possible nucleotides of length X contains substantially $4^X$ different nucleic acids (e.g., 16 different nucleic acids for a 2 mer, 64 different nucleic acids for a 3 mer, 65536 different nucleic acids for an 8 mer). Some small number of sequences can be absent from a pool of all possible nucleotides of a particular length due to synthesis problems, and inadvertent cleavage).

In some applications, it may be advantageous to utilize oligonucleotide arrays containing collections of pairs of nucleic acid probes for each of the RNAs being monitored. In such instances, each probe pair includes a probe (e.g., a 20-mer or a 25-mer) that is perfectly complementary to a subsequence of a particular mRNA or amplification product generated therefrom, and a companion probe that is identical except for a single base difference in a central position. The mismatch probe of each pair can serve as a internal control for hybridization specificity. See for example, Lockhart, et al., Nature Biotechnology 14:1675–1680 (1996); and Lipshutz, et al., Nature Genetics Supplement 21:20–24, 1999, which are incorporated by reference herein in their entirety.

2. cDNA Arrays

Instead of using arrays containing synthesized probes, the probes can instead be full length cDNA molecules or fragments thereof which are attached to a solid support. Expression analyzes conducted using such probes are described, for example, by Schena et al. (Science 270:467–470 (1995) and DeRisi et al. (Nature Genetics 14:457–460 (1996), which are incorporated herein by reference in their entirety.

D. Array Structure

As indicated above, the number of elements in an array can vary depending upon factors such as sensitivity and the number of redundant elements desired for use as controls, with the number of elements generally ranging from 1 to $10^5$. For expression analysis methods, the number of elements most typically includes at least 1000 elements and extends up to 10,000 or even 100,000 elements depending upon the number of sequences being probed and whether cDNA or synthetic oligonucleotide probes are utilized. However, other numbers of elements can be used within the general ranges set forth above.

E. Probe Density and Length

The density of probes within an element can vary widely, depending upon factors such as sensitivity, complexity of sample and whether characteristic signals for the hybridization complex of interest have been identified. Depending upon such factors, density typically varies from 1 to $10^{18}$ probes/cm$^2$, as set forth above. Density in some embodiments is $10^2$ to $10^5$ probes/cm$^2$. In still other methods, density is approximately $10^5$ to $10^8$ probes/cm$^2$. In yet other embodiments, density is between $10^8$ and $10^{12}$ probes/cm$^2$. In yet other embodiments, density is between $10^{12}$ and $10^{15}$ probes/cm$^2$. Probe concentration in other methods is between $10^{15}$ to $10^{18}$ probes/cm$^2$.

Probe length can vary significantly, depending for example on whether synthetic oligonucleotides or cDNAs are used in the array. The synthetic oligonucleotides tend to be quite short, such as 10-20, 20-30, 30-40 or 40-50 base pairs long, although cDNA fragments in this length can also be used. When nucleic acids corresponding to full length genes are utilized in the array, probe length can vary from a few thousand base pairs up to approximately 100,000 base pairs. Probe length between elements may also vary widely, since different cDNAs, for example, may be attached at different elements of the array. As described previously, however, probes can range from 5 up to $10^6$ base pairs long, including all sizes therebetween.

F. Detection and Quantitation

Signal transmission and detection is as described above. In general, a signal is launched down each signal path and a modulated transmitted and/or reflected signal (i.e., response signal) detected to identify binding of target to a probe. Because the sequence of the probe or probes at each element is known, a computer can monitor which element a signal is coming from, making it possible to determine the sequence of the target hybridized at each of the elements from which a response signal is generated. Quantitation is possible by measuring changes in the intensity of a characteristic peak associated with hybridization, or even the background. Changes in an absorption peak, for example, correspond to a change in concentration. In some instances, a known quantity of a target having a sequence complementary to a probe in the array can be added to perform a calibration. Other detection methods for reading microarrays is described by Cheung et al., Nature Genetics Supplement 21:10–15–19 (1999).

XV. Sequence Checking

A. General

Certain methods of the present invention. involve various aspects of sequence checking. For example, some methods involve screening samples for known sequences. Such methods find utility in a variety of different applications. Examples include, for example, identifying mutations known to affect the efficacy of certain types of medical treatment, analyzing a forensic sample taken from a crime scene, paternity testing, checking for viral or bacterial sequences to test for infection and testing food for microorganism contamination. Other sequence checking applications involve developing a "signature" for an unknown sequence and in gene discovery. Developing a signature for unknown sequences involves hybridizing nucleic acids of known sequence with nucleic acids of unknown sequence which are bound to a solid support. By identifying the number and particular sequences of nucleic acids which hybridize to a longer unknown nucleic acid sequence it is possible to develop a "signature" for the unknown sequence, thus allowing the nucleic acid of unknown sequence to be classified. Such signatures are useful in initial screening for new genes.

Methods for sequence checking are reviewed by Hacia, Nature Genetics Supplement 21:42–47 (1999), which is incorporated herein by reference in its entirety.

B. Identification of Particular Mutations

1. Sample Preparation

In general, sample types and methods for isolating nucleic acids from cells are similar to the methods described for expression analysis. Once nucleic acids from a sample are obtained, typically segments of interest are amplified from genomic DNA, RNA or cloned templates according to methods set forth above. Following amplification, targets are subjected to partial random degradation to minimize inter- and intramolecular structures that might interfere with hybridization of target with probes. Targets are then contacted with probes of the appropriate sequence as just described.

2. Methodology

For methods designed to identify particular mutations, nucleic acid probes are selected to have sequences which are at least partially complementary with the target sequence of interest. Thus, for example, in the instance of testing forensic evidence, the probe would be complementary to a sequence unique to the suspect. In paternity testing, a probe would be prepared to be complementary to a sequence from the putative father. Similarly, in food adulteration testing, probes would be selected to be complementary to unique sequences from various microorganisms. As can readily be appreciated, other probe sequences can be tailored according to the particular sequence of interest.

In methods in which the probe is selected to be complementary with the sequence of the target of interest, typically stringency washes are utilized to remove nucleic acids which form mismatches with the probe. Detection of a hybridization complex in these cases simply involves monitoring a signal generated by the formation of a hybridization complex. Formation of a signal is indicative of the target of interest being present in the sample. In this approach, it is not necessary to have previously acquired a hybridization profile.

However, for other methods in which a hybridization profile for the probe/target complex of interest is known, detection can include examining the test spectrum for the presence of a signal (or set of signals) which is characteristic for that particular complex (for example, a complementary signal). The existence of such a signal indicates that the sample includes the target of interest. As described above, by utilizing profiles, it is possible to avoid stringency washes.

Regardless of approach, with the sequence checking methods of the present invention, it is not necessary to use labeled nucleic acids. With profiles, it is also possible to use fewer sequences on an array because a single probe can provide unambiguous sequence information, particularly since it is possible to distinguish between single base pair mismatches with the methods of this present invention.

3. Array Design

Like expression analysis methods, sequence checking methods can also utilize array technology. In general the number of elements in the array is considerably less than in the expression analysis case since fewer targets are examined in sequence checking. Multiple elements may nonetheless be utilized if the presence of multiple different nucleic acids in a sample are being tested for. In such methods, each element would contain probes complementary to at least a protion of one of the target sequences being assayed. It may also be desireable to use redundant elements (for example, multiple elements each having the same sequence) as a control. Given the nature of the application, arrays typically have 1 to 100 elements. However, as described earlier, from a technical standpoint, there is no reason that the array could not include many more elements.

The density of probes within each element can vary widely as set forth above, generally ranging from 1 probe per element to $10^{18}$ probes/cm$^2$ and all sizes therebetween. A single probe per element can be used in situations in which there is excellent sensitivity and/or well-defined characteristic signals for the hybridization complex of interest. Density in other embodiments is $10^2$ to $10^5$ probes/cm$^2$. In still other methods, density is approximately $10^5$ to $10^8$ probes/cm$^2$. In yet other embodiments, density is between $10^8$ and $10^{12}$ probes/cm$^2$. In yet other embodiments, density is between $10^{12}$ and $10^{15}$ probes/cm$^2$. Probe concentration in other methods is between $10^{15}$ to $10^{18}$ probes/cm$^2$.

Probe length can also vary widely, ranging from a few bases to 100,000 bases, for example. In various embodiments, the length may be 10-25 base pairs, 25-50, 50-100, 100-250, 250-500, 500-1000; 1,000-10,000 and 10,000 to 100,000 base pairs.

C. Sequence Signatures and Gene Discovery

Typically these methods include placing numerous nucleic acids of unknown sequence (for example, cDNAs) on a chip to form an array of nucleic acids of unknown sequence. These unknown nucleic acids can then be probed with relatively short nucleic acids of known sequence. The identity of the known sequence or sequences that hybridize with a particular nucleic acid of unknown sequence provides a "signature" of the nucleic acid of unknown sequence. As noted above, such profiles can be useful in categorizing an unknown sequence or in gene discovery.

XVI. Single Nucleotide Polymorphism Analysis

A. General

Single nucleotide polymorphisms (SNPs) are point mutations that constitute the most common type of genetic variation. SNPs are stable mutations that can be contributory factors for human disease and can also serve as genetic markers. In fact, a number of SNPs have already been correlated with various human diseases. Publication WO 93/02216 provides an extensive list of such SNPs. Additional SNPs are listed in Cooper, et al., Hum. Genet. 85:55–74 (1990). Both of these publications are incorporated herein by reference in their entirety.

B. Methodology

SNP detection methods of the present invention are similar to the sequence checking methods described above, particularly with regard to sample preparation, hybridization conditions and washing. Typically, a nucleic acid probe is attached to an element on a chip. Depending on the number of SNPs being interrogated, there can be a plurality of elements, thereby forming an array. Each element normally includes probes of the same sequence. In certain methods, the probe sequence is such that there is complementary binding with the target containing the SNP of interest (i.e., the probe and target form a complementary complex).

SNP analysis is particularly suited for analysis using hybridization profiles. Using hybridization profiles for each polymorphic sequence and its corresponding complement, it is possible to examine a spectrum for the presence of a signal or signals characteristic for each of the various SNP hybridization complexes to identify the polymorphism which is present in the target sequence.

As an example of alternative forms of analysis, assume that the wild type form of a sequence containing an SNP has the sequence GCGCCGAGACAGCCAGGTCG (SEQ ID NO: 6) and the variant allele has the sequence GCGC-CGAGACTGCCAGGTCG (SEQ ID NO: 7). The complementary sequence for the wild type from is CGCGGCTCT-GTCGGTCCAGC (SEQ ID NO: 8); whereas, the complementary sequence for the variant allele is CGCG-GCTCTGACGGTCCAGC (SEQ ID NO: 9)(for all sequences, the polymorphic site is indicated in bold).

In certain embodiments, a probe having a sequence complementary to that of the wild type form is coupled to a signal path and then contacted with a sample containing targets having either the wild type form (i.e., base A is at the polymorphic site) and/or the variant allele form (i.e., base T at the polymorphic site). After washing the coupled probe under stringent conditions to remove noncomplementary sequences, a signal generated by formation of a hybridization complex indicates that the target is of the wild type form.

Alternatively, hybridization profiles can be used in the analysis. Still assuming coupling of the wild type form to the signal path, if a target in the sample is of the wild type form, signals characteristic of a complementary complex are generated. However, if the target is the variant allelic form, then a mismatch complex is formed and a signal or signals characteristic of that complex are formed. If a hybridization profile for that particular mismatch hybridization complex has already been obtained and stored, it is possible to identify the polymorphic form directly.

Variations on this basic approach are possible. For example, the probe sequence attached to the transmission line can be that of the variant allele rather than the wild type. In other methods, a probe or set of probes complementary to the wild type form and a different probe or set of probes complementary to the variant allele are attached to different transmission lines, such as different elements of an array for example.

C. Arrays

1. Methods of Analysis

Arrays can be used in SNP analysis in different ways. In some instances, probes complementary to different sequences having different SNPs can be coupled to signal paths at different elements; in such cases, multiple different sequences can be analyzed for different SNPs. With other methods, probes complementary to the different allelic forms of a particular polymorphism are attached to different elements of an array.

In other methods for analyzing SNPs, an array of nucleic acid probes that are complementary to subsequences of a target sequence can be utilized to determine the identity of a target sequence, measure its amount, and detect differences between the target and a reference sequence using a procedure commonly referred to as "tiling." See for example, WO 95/11995; U.S. Pat. No. 5,858,659; Chee, et al. Science 274:610–614 (1996); U.S. Pat. No. 5,837,832; and Lipshutz; et al., BioTechniques 19:442–447 (1995), each of which is incorporated herein by reference in its entirety.

In brief, tiling strategies utilize a tiled array, such as a 4L tiled array, for example. In a 4L tiled array, there is a set of four probes of relatively short length (for example, 15-mers) which vary at the SNP position but which otherwise are identical and are perfect complements to a segment of the nucleic acid being screened. A perfectly complementary probe binds more tightly than those probes which have a single mismatch. In traditional methods using fluorescently labeled probes, the probe with the highest intensity corresponds to the unknown base. In the current methods, the label is unnecessary; perfect matches and mismatches can be distinguished by direct measurement. This approach to SNP analysis can be extended to examine long nucleic acid targets and detect numerous polymorphisms/mutations relative to a characterized consensus sequence.

2. Design

Considerations for array design in SNP analysis parallels that for sequence checking since SNP analysis is essentially a specific application of sequence checking. Thus, the probe density and length considerations described in relation to sequence checking apply to SNP analysis also.

The number of elements in the array, as for the sequence checking applications generally, often is fairly small given the specific nature of the analysis. With characteristic signals for the various allelic forms of a SNP, it is possible to have a single element. However, multiple element arrays can be useful. For example, as described above, it may be desireable to have a probe for each of the different allelic forms at a separate element. Also, multiple elements each containing the same probe may be useful for control purposes. Another control approach may involve using different sequences for the same allelic form of an SNP at different elements. The different sequences are selected such that the SNP site hybridizes at different locations on the various sequences (for example, in one element the SNP site hybridize near one end of the probe; in another element, the SNP site hybridizes in the middle of the probe, etc.).

XVII. Sequence Determination

A. General

Traditional sequencing technologies involve complicated and time consuming procedures requiring electrophoretic size separation of labeled DNA fragments (see, for example, Alphey, DNA Sequencing: From Experimental Methods to BioInformatics, Springer-Verlag, N.Y., 1997). An alternative, typically referred to as "Sequencing by Hybridization" (SBH) has been proposed. See for example, Lysov et al., Dokl. Akad. Nauk SSSR 303:1508–1511 (1988); Bains et al., J. Teor. Biol. 135:303–307 (1988); Drmanac et al., Genomics 4:114–128 (1989); Barinaga, Science 253:1489 (1991); Stresoska et al., Proc. Natl. Acad. Sci. USA 88:10089 (1992); Bains, BioTechnology 10:757–758 (1992); and U.S. Pat. No. 5,202,231, each of which is incorporated herein by reference in its entirety. In general, SBH uses a set of short nucleic acid probes of defined sequence to probe for complementary sequences on a longer target strand of DNA. The defined sequences which hybridize to the target can then be aligned using computer algorithms to construct the sequence of the target nucleic acid.

B. Methodology

The strategy of SBH can be illustrated by the following example, A 12-mer target DNA sequence, AGCCTAGCT-GAA (SEQ ID NO: 10), is mixed with a complete set of octanucleotide probes. If only perfect complementarity is considered, five of the 65,536 octamer probes-TCGGATCG (SEQ ID NO: 11), CGGATCGA (SEQ ID NO: 12), GGATC-GAC (SEQ ID NO: 13), GATCGACT (SEQ ID NO: 14), and ATCGACTT (SEQ ID NO: 15) will hybridize to the target. Alignment of the overlapping sequences from the hybridiing probes reconstructs the complement of the original 12-mer target:

| TCGGATCG | (SEQ ID NO: 11) |
| CGGATCGA | (SEQ ID NO: 12) |
| GGATCGAC | (SEQ ID NO: 13) |
| GATCGACT | (SEQ ID NO: 14) |
| ATCGACTT | (SEQ ID NO: 15) |
| TCGGATCGACTT | (SEQ ID NO: 16) |

SBH can be performed in two formats. Hybridization methodology can be carried out by attaching target DNA to a surface. The target is then interrogated with a set of oligonucleotide probes, one at a time (see Strezoska et al., Proc. Natl. Acad. Sci. USA 88:10089–10093 (1991); and Drmanac et al., Science 260:1649–1652, (1993), each of which is incorporated herein by reference). Although this approach can be implemented with well established methods of immobilization and hybridization detection, it involves a large number of manipulations. For example, to probe a sequence utilizing a full set of octanucleotides, tens of thousands of hybridization reactions must be performed.

In the second format, SBH is carried out by attaching probes to a surface in an array format where the identity of the probes at each site is known. The target DNA is then added to the array of probes. The hybridization pattern determined in a single experiment directly reveals the identity of all complementary probes.

The detection methodology of the present invention can be used with both formats. However, preferably the analysis is conducted with arrays. Each element of the array would include a probe of known sequence. Hybridization at each of the various elements can be detected by modulation of the signal transmitted to the particular element. Other SBH methods require some type of labeling to visualize the hybridization pattern and identify which probes in the array have hybridized with target. Labeling with the methods of the present invention is not required since hybridization can be monitored directly.

Variations of the SBH procedure have been developed, primarily to address a major problem with SBH, namely the problem of mismatches creating errors in the sequence determination. One such method termed "positional SBH" (PSBH) utilizes duplex probes having 3' single-stranded overhangs to capture the target, and is followed by enzymatic ligation of the target to the duplex probe. This approach is designed to reduce mismatches (see for example, Broude, et al., Proc. Natl. Acad. Sci. USA 91:3072–3076 (1994), which is incorporated herein by reference in its entirety). PSBH itself has been further modified so that following the ligation reaction, DNA polymerase is added to extend the immobilized probe as a way of further reducing mismatches during capture of the target (see for example, Kuppuswamy, et al., Proc. Natl. Acad. Sci. USA 86:1143–1147 (1991), which is incorporated herein by reference in its entirety).

The detection system of the present invention is amenable to these variations on the standard SBH methodology, and essentially the approach is the same as described with the traditional SBH approach with the addition of the ligation and/or extension steps. However, because the present detection system can distinguish between mismatch and perfectly complementary binding, these additional steps are believed to be unnecessary. The ability to distinguish between the types of binding is also anticipated to allow greater flexibility in stringency washings.

C. Array Design

In general, a large number of elements are preferred in sequencing methods. The number of elements in sequencing methods often is at least 1000 and can extend to 100,000. In various embodiments, the number of elements may be $10^3$, $10^4$, $10^5$ or any range therebetween. There may be certain instances, however, when the number of preferred elements is outside these ranges.

Probe density factors parallel those set forth for expression analysis. The length of the probes can vary widely. Arrays using synthetic probes, for example, may have probes that are typically 5–25 bases long. Probe length in other embodiments may be 10 to 25, 25 to 50, 50 to 100, 100-250, 250 to 500 or 500 to 1,000 bases long.

The following examples are provided to illustrate certain aspects of the invention but are not to be construed so as to limit the scope of the invention.

EXAMPLE I

Nucleic Acid Hybridization:
Poly G and Poly C Sequences

This example was performed to demonstrate the ability of the system to detect hybridization between complementary sequences and discriminate against sequences lacking complementarity. The experiment was conducted using a bio-assay device as shown in FIG. 2C and described in the accompanying text.

An oligonucleotide (HPLC purified) composed of a 51-mer of guanine (oligo G), thiolated at the 5' end was obtained from Operon Technologies, Inc. (Alameda, Calif.).

This oligonucleotide was resuspended to 1 mL in 1×SSC (Sigma, St. Louis, Mo.), an aliquot removed and reduced by adding an equal volume of 0.08M DTT in 1×SSC. The mixture was incubated for approximately 16 hr at 37 ° C. then passed through a NAP 10 Column (Sephadex G-25, Pharmacia, Uppsala, Sweeden). Unused aliquots of the reduced material were stored under nitrogen gas at −20° C. For experiments, 200 pmols/mL of reduced oligo-G was allowed to bind to the gold substrate for 60 min. and the S-parameters were measured and stored.

A 50-mer composed entirely of A, T, and G nucleotides in 1×SSC at 100 pM concentration was used as a control, since these combinations of bases should not hybridize with a nucleic acid comprising solely G residues. The response in the S-parameters was measured at several time intervals (over several hours); no change was noted during this time period.

Figure 9:
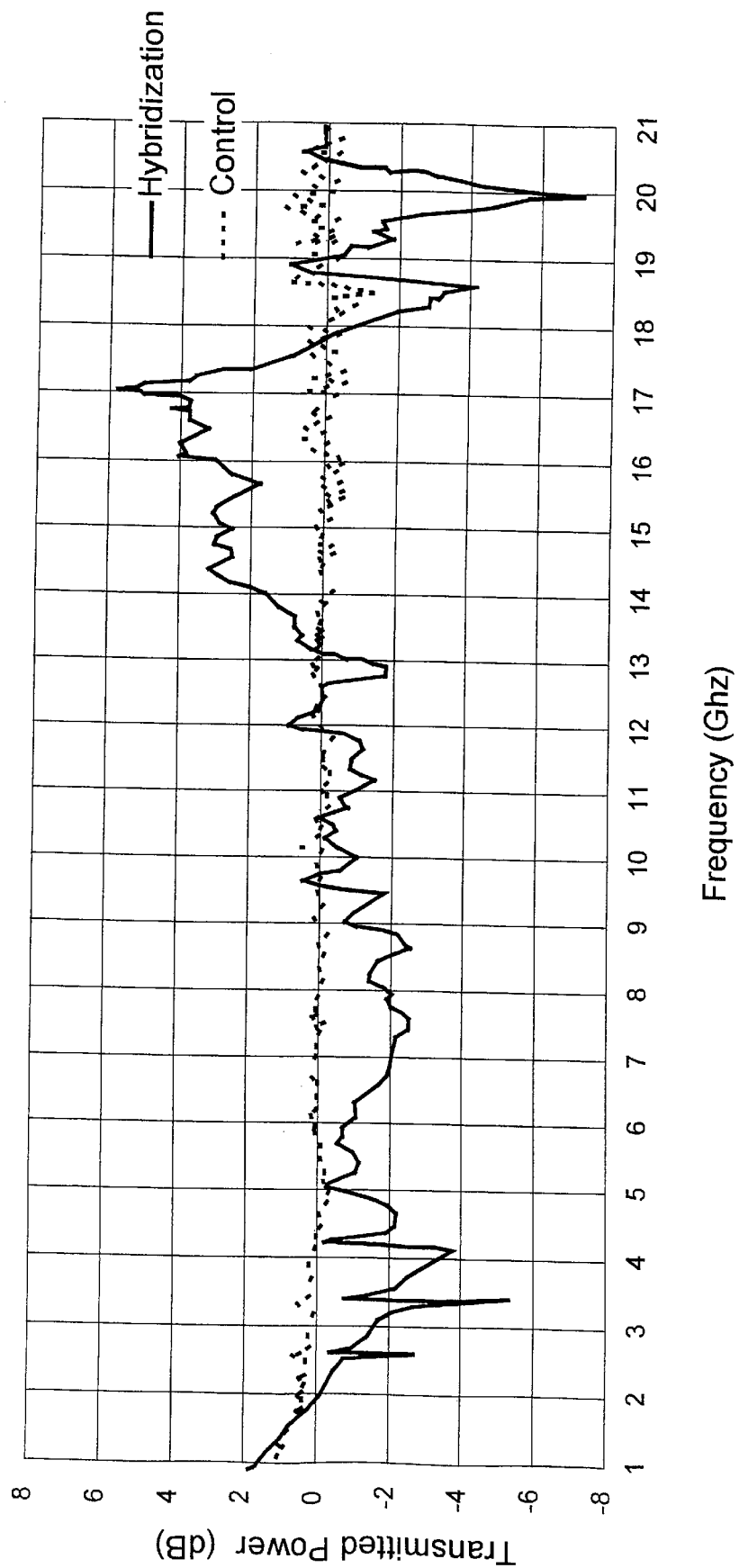
FIG. 9 illustrates the change in signal resulting from hybridization of a poly G and poly C sequence.

Subsequently, a 50-mer target nucleic acid (1 pM) composed entirely of cytosine ("C") in an identical buffer was contacted with the probe. In this instance, the target was expected to strongly hybridize with the bound nucleic acid probe. The S-parameters were again measured at several time intervals. In this instance, however, a considerable change was observed. FIG. 9 shows the effects on the transmitted power of both the control (dashed line with little signal variation) and the hybridization experiments (solid line) after one hour and shows a strong, direct response to hybridization of the C-based 50-mer to the G-based probe attached to the transmission line; the signal for the target control in contrast, was little changed. This experiment demonstrates the capability of the present method to detect the formation of hybridization complexes, even in the presence of non-complementary sequences at concentrations 100 times that of the complementary sequence.

EXAMPLE II
Discrimination between Complementary, Mismatched and Non-complementary Sequences Another set of experiments was conducted to determine if the system of the present invention could differentiate between various hybridization complexes involving different single base pair mismatches, complementary sequences and non-complementary sequences. The bio-assay device, general experimental conditions and signal acquisition were as described in Example I.

Three nucleic acids (10-mers) incorporating mismatches relative to a test sequence were obtained. The nucleic acid probe sequence was 5'-CATATCATTC-3' (SEQ ID NO: 1) and was thiolated at the 5' end; the thiol group was used to bind the probe to the gold surface. The probe was exposed to the gold spice for 60 minutes then washed with 1×SSC (saline sodium citrate). Nucleic acids incorporating a mismatch were prepared so as to have a mismatch at the beginning, middle or end of the sequence (5'-GAATGATATC-3' (SEQ ID NO: 2); 5'-GAATCATATG-3' (SEQ ID NO: 3); 5'-CAATGATATG-3' (SEQ ID NO: 4), respectively). Controls consisting of a complementary strand (5'-GAATGATATG-3' (SEQ ID NO: 5)) and a non-complementary cytosine 10-mer stand of "C's" were also tested. Each of the control probes was allowed to contact the target sequence on the gold surface for 30 minutes and then washed with 1×SSC. A specti for each nucleic acid in the presence of the probe was acquired by measuring S-parameters over several time intervals.

Figure 10A:
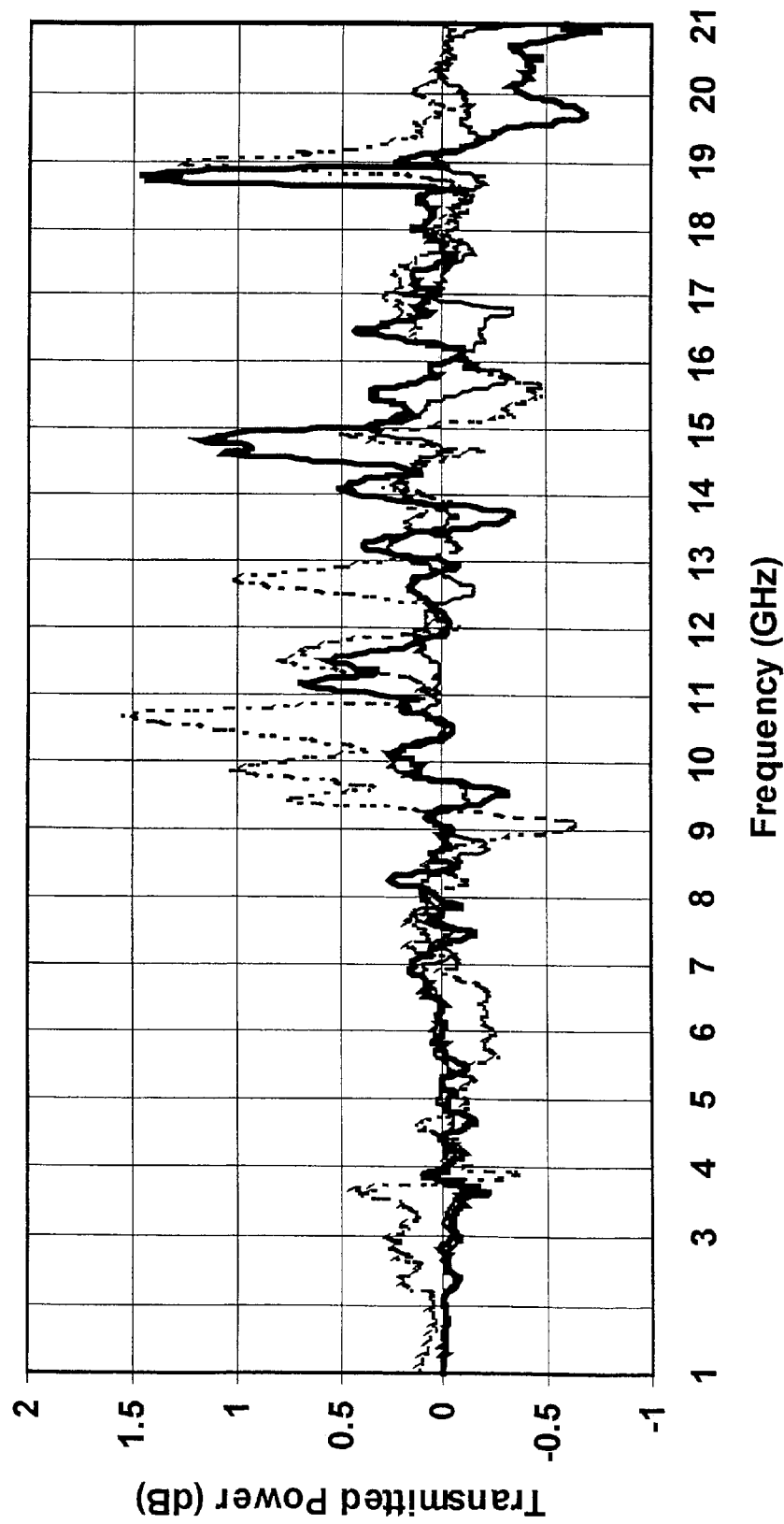
FIG. 10A shows a complete scan (1–21 GHz) showing signals for complementary and mismatched targets to a nucleic acid probe having the sequence 5'-CATATCATTC-3' (SEQ ID NO: 1).
Figure 10B:
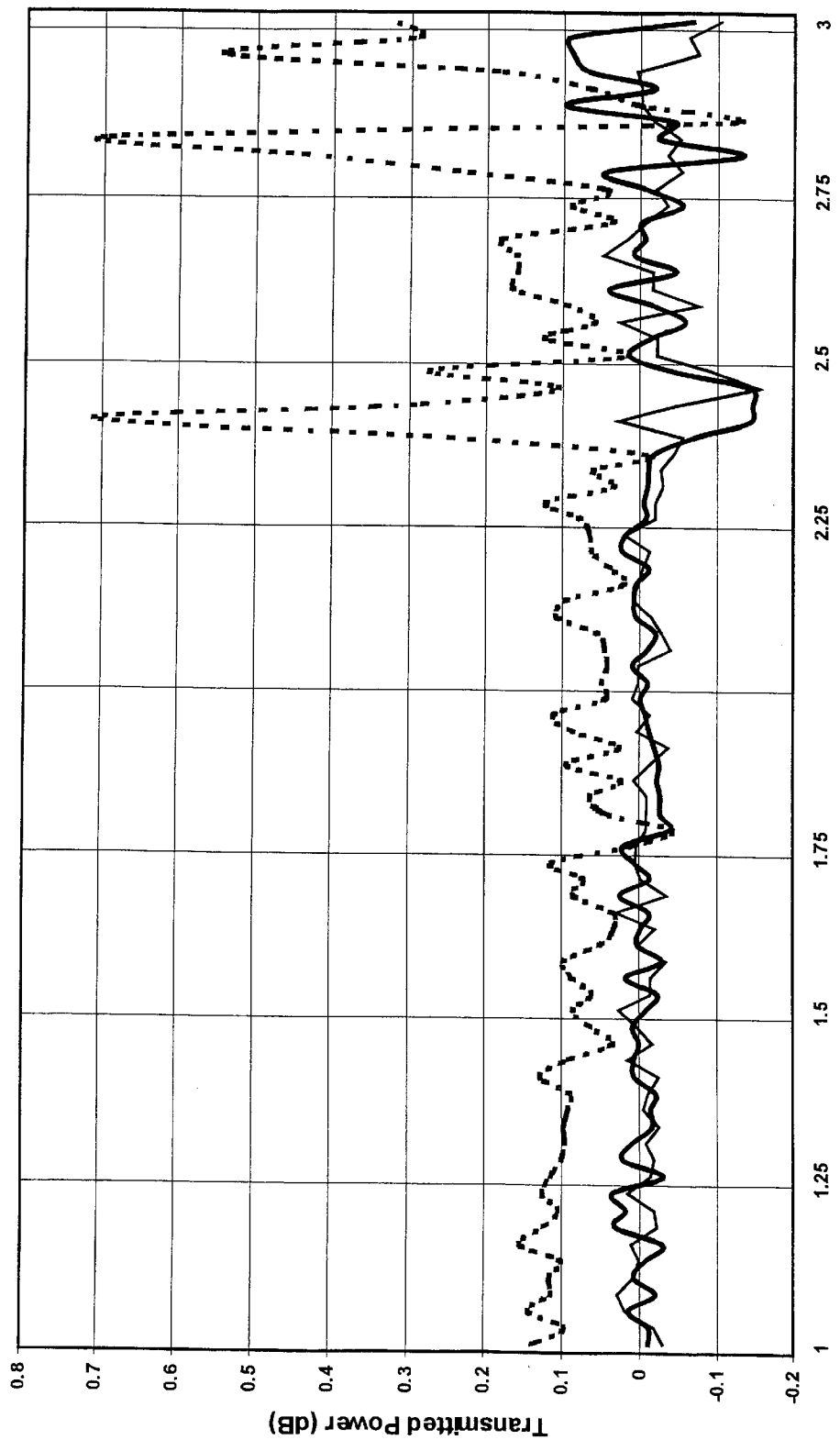
FIG. 10B is an expansion of the spectrum shown in FIG. 10A.

Results are shown in FIGS. 10A and 10B in which frequency (in GHz) is plotted against transmitted power (dB). FIG. 10A is a full scan from 1–21 GHz and in general illustrates that each hybridization complex gave a different spectrum. The spectrum for the complementary hybridization complex (dashed line) is significantly different than that for the non-complementary hybridization complexes (solid lines). This difference is shown even more clearly in FIG. 10B which depicts an expansion of the spectrum from 1–3 GHz.

These results illustrate the ability of the methods of the present invention to differentiate between subtle differences in sequences, including sequences which vary only at a single base. Such discriminatory power is of particular utility in SNP analyses, for example. This experiment also demonstrates how it is possible using the methods described herein to obtain a signature for different hybridization complexes and how it is possible to use such a signature, in particular signals which are characteristic for a certain complex, to determine whether such a complex exists in a test solution and/or whether a complex comprised of related nucleic acids is present.

While the above is a complete description of possible embodiments of the invention, Various alternatives, modifications, and equivalents may be used. For instance a person skilled in the art will appreciate that the signal path of foregoing bio-assay device is not limited to a transmission line. Other transmission mediums, such as conductive or dielectric waveguides may alternatively be used. The above description should be view as only exemplary embodiments of the invention, the boundaries of which are appropriately defined by the metes and bounds of the following claims.

Further, all publications, patent documents and other reference cited in this application are incorporated by reference in their entirety for all purposes to the same extent as if each individual publication, patent document or reference was so individually denoted.

What is claimed is:

1. A method for detecting nucleic acid hybridization complexes, comprising:
   (1) acquiring a spectrum for a hybridization complex formed between (a) a nucleic acid probe that is electromagnetically coupled to a portion of a signal path wherein one or more said signal path and one or more said probe are present in an apparatus in which said method is carried out, each signal path having a corresponding nucleic acid probe, and wherein a plurality of probes and signal paths, if plurality is present, are optionally arranged as elements of an array, and (2) a nucleic acid target in a sample, by propagating a test signal along said signal path and detecting a response signal for the hybridization complex formed between the probe and target, wherein said propagating step comprises varying said test signal with time; and
   (b) examining said spectrum for the presence of a signal which is characteristic for a hybridization complex between said probe and a particular target, wherein said acquiring takes place without washing unbound nucleic acids from said probe before acquiring said spectrum.

2. The method of claim 1, wherein said method is being carried out to distinguish complementary from mismatch hybridization.

3. The method of claim 2, wherein:
   (a) the target includes a known polymorphic site, which can include a first or a second base, and wherein the target forms a complementary hybridization complex with said probe if said target includes said first base and forms a mismatch hybridization complex if said target includes said second base; and
   (b) examining comprises examining for the presence of a complementary signal and a mismatch signal, the presence of the complementary signal being indicative of said target including the first base at the polymorphic site and the presence of the mismatch signal being indicative of said target including said second base at said polymorphic site.

4. The method of claim 1, wherein said probe and said target are unlabeled.

5. The method of claim 1, wherein said varying comprises varying the frequency of the test signal that is propagated along the signal path.

6. The method of claim 5, wherein said test signal is a microwave signal.

7. The method of claim 1, wherein said signal path comprises a transmission line.

8. The method of claim 7, wherein said probe is directly attached to said transmission line.

9. The method of claim 1, wherein:
   (a) said sample potentially comprises a target of known sequence;
   (b) said probe has a sequence which is complementary to said target of known sequence; and
   (c) said response signal is indicative of said sample containing said target of known sequence.

10. The method of claim 1, wherein said target is present in a sample containing nucleic acids amplified from genes expressed in a particular cell.

11. The method of claim 1, wherein said examining comprises measuring changes in signal amplitude or frequency at a plurality of different time points to obtain a plurality of measured values.

12. The method of claim 11, wherein said measured values are used to evaluate the kinetics of hybridization between said probe and target.

13. The method of claim 1, wherein a plurality of probes of the same sequence are electromagnetically coupled to the transmission line and wherein said examining is used to quantitate the number of hybridization complexes formed.

14. The method of claim 1, wherein said test signal has a frequency or range of frequencies in a range from 10 MHz to 1000 GHz.

15. The method of claim 1, wherein said test signal frequency is a resonant frequency $f_{res}$ and said complementary signal and said mismatch signal have different $f_{res}$ values from each other.

16. The method of claim 1, wherein a plurality of said signal paths and corresponding probes are arranged as elements in an array.

17. The method of claim 16, wherein:
   (a) said sample potentially comprises a first target of known sequence and a second target of a different known sequence;
   (b) said plurality of probes comprises a first probe complementary to said first target and a second probe complementary to said second target, said first and second probe being located at a first and second element of said array, respectively; and
   (c) said detecting comprises monitoring said first and second element for a first and second response signal, respectively, wherein said first response signal indicates the presence of said first target in said sample and wherein said second response signal indicates the presence of said second target in said sample.

18. The method of claim 17, wherein said test signal has a frequency or range of frequencies in a range from 10 MHz to 1000 GHz.

* * * * *

SEQUENCE LISTING

<160> NUMBER OF SEQ ID NOS: 16

<210> SEQ ID NO 1
<211> LENGTH: 10
<212> TYPE: DNA
<213> ORGANISM: Artificial Sequence
<220> FEATURE:
<223> OTHER INFORMATION: This artificial sequence demonstrates the
      principle of distinguishing complementary and mismatch signals
      and has no relationship to any known sequence.  It was synthesized
      using an automated polynucleotide sequencer and used as described
      in the text

<400> SEQUENCE: 1

```
catatcattc                                                               10

<210> SEQ ID NO 2
<211> LENGTH: 10
<212> TYPE: DNA
<213> ORGANISM: Artificial Sequence
<220> FEATURE:
<223> OTHER INFORMATION: This artificial sequence demonstrates the
      principle of distinguishing complementary and mismatch signals
      and has no relationship to any known sequence.  It was synthesized
      using an automated polynucleotide sequencer and used as described
      in the text

<400> SEQUENCE: 2
gaatgatatc                                                               10

<210> SEQ ID NO 3
<211> LENGTH: 10
<212> TYPE: DNA
<213> ORGANISM: Artificial Sequence
<220> FEATURE:
<223> OTHER INFORMATION: This artificial sequence demonstrates the
      principle of distinguishing complementary and mismatch signals
      and has no relationship to any known sequence.  It was synthesized
      using an automated polynucleotide sequencer and used as described
      in the text

<400> SEQUENCE: 3
gaatcatatg                                                               10

<210> SEQ ID NO 4
<211> LENGTH: 10
<212> TYPE: DNA
<213> ORGANISM: Artificial Sequence
<220> FEATURE:
<223> OTHER INFORMATION: This artificial sequence demonstrates the
      principle of distinguishing complementary and mismatch signals
      and has no relationship to any known sequence.  It was synthesized
      using an automated polynucleotide sequencer and used as described
      in the text

<400> SEQUENCE: 4
caatgatatg                                                               10

<210> SEQ ID NO 5
<211> LENGTH: 10
<212> TYPE: DNA
<213> ORGANISM: Artificial Sequence
<220> FEATURE:
<223> OTHER INFORMATION: This artificial sequence demonstrates the
      principle of distinguishing complementary and mismatch signals
      and has no relationship to any known sequence.  It was synthesized
      using an automated polynucleotide sequencer and used as described
      in the text

<400> SEQUENCE: 5
gaatgatatg                                                               10

<210> SEQ ID NO 6
<211> LENGTH: 20
<212> TYPE: DNA
<213> ORGANISM: Artificial Sequence
<220> FEATURE:
<223> OTHER INFORMATION: This sequence is completely hypothetical and
      was designed to illustrate the principle of distinguishing
      complementary and mismatch signals.  It was not designed to have
      any relationship to any known sequence and was never synthesized
```

```
<400> SEQUENCE: 6
gcgccgagac agccaggtcg                                              20

<210> SEQ ID NO 7
<211> LENGTH: 20
<212> TYPE: DNA
<213> ORGANISM: Artificial Sequence
<220> FEATURE:
<223> OTHER INFORMATION: This sequence is completely hypothetical and
      was designed to illustrate the principle of distinguishing
      complementary and mismatch signals.  It was not designed to have
      any relationship to any known sequence and was never synthesized

<400> SEQUENCE: 7
gcgccgagac tgccaggtcg                                              20

<210> SEQ ID NO 8
<211> LENGTH: 20
<212> TYPE: DNA
<213> ORGANISM: Artificial Sequence
<220> FEATURE:
<223> OTHER INFORMATION: This sequence is completely hypothetical and
      was designed to illustrate the principle of distinguishing
      complementary and mismatch signals.  It was not designed to have
      any relationship to any known sequence and was never synthesized

<400> SEQUENCE: 8
cgacctggct gtctcggcgc                                              20

<210> SEQ ID NO 9
<211> LENGTH: 20
<212> TYPE: DNA
<213> ORGANISM: Artificial Sequence
<220> FEATURE:
<223> OTHER INFORMATION: This sequence is completely hypothetical and
      was designed to illustrate the principle of distinguishing
      complementary and mismatch signals.  It was not designed to have
      any relationship to any known sequence and was never synthesized

<400> SEQUENCE: 9
cgacctggca gtctcggcgc                                              20

<210> SEQ ID NO 10
<211> LENGTH: 12
<212> TYPE: DNA
<213> ORGANISM: Artificial Sequence
<220> FEATURE:
<223> OTHER INFORMATION: This sequence is completely hypothetical and
      illustrates the principle of determining a full sequence from
      overlapping complementary signals.  It was not designed to have
      any relationship to any known sequence and was never synthesized

<400> SEQUENCE: 10
agcctagctg aa                                                      12

<210> SEQ ID NO 11
<211> LENGTH: 8
<212> TYPE: DNA
<213> ORGANISM: Artificial Sequence
<220> FEATURE:
<223> OTHER INFORMATION: This sequence is completely hypothetical and
      illustrates the principle of determining a full sequence from
      overlapping complementary signals.  It was not designed to have
      any relationship to any known sequence and was never synthesized

<400> SEQUENCE: 11
```

```
gctaggct                                                          8

<210> SEQ ID NO 12
<211> LENGTH: 8
<212> TYPE: DNA
<213> ORGANISM: Artificial Sequence
<220> FEATURE:
<223> OTHER INFORMATION: This sequence is completely hypothetical and
      illustrates the principle of determining a full sequence from
      overlapping complementary signals.  It was not designed to have
      any relationship to any known sequence and was never synthesized

<400> SEQUENCE: 12 agctaggc                                                          8

<210> SEQ ID NO 13
<211> LENGTH: 8
<212> TYPE: DNA
<213> ORGANISM: Artificial Sequence
<220> FEATURE:
<223> OTHER INFORMATION: This sequence is completely hypothetical and
      illustrates the principle of determining a full sequence from
      overlapping complementary signals.  It was not designed to have
      any relationship to any known sequence and was never synthesized

<400> SEQUENCE: 13 cagctagg                                                          8

<210> SEQ ID NO 14
<211> LENGTH: 8
<212> TYPE: DNA
<213> ORGANISM: Artificial Sequence
<220> FEATURE:
<223> OTHER INFORMATION: This sequence is completely hypothetical and
      illustrates the principle of determining a full sequence from
      overlapping complementary signals.  It was not designed to have
      any relationship to any known sequence and was never synthesized

<400> SEQUENCE: 14 tcagctag                                                          8

<210> SEQ ID NO 15
<211> LENGTH: 8
<212> TYPE: DNA
<213> ORGANISM: Artificial Sequence
<220> FEATURE:
<223> OTHER INFORMATION: This sequence is completely hypothetical and
      illustrates the principle of determining a full sequence from
      overlapping complementary signals.  It was not designed to have
      any relationship to any known sequence and was never synthesized

<400> SEQUENCE: 15 ttcagcta                                                          8

<210> SEQ ID NO 16
<211> LENGTH: 12
<212> TYPE: DNA
<213> ORGANISM: Artificial Sequence
<220> FEATURE:
<223> OTHER INFORMATION: This sequence is completely hypothetical and
      illustrates the principle of determining a full sequence from
      overlapping complementary signals.  It was not designed to have
      any relationship to any known sequence and was never synthesized

<400> SEQUENCE: 16
ttcagctagg ct                                                    12
```